US009611314B2

(12) United States Patent
Tombran-Tink et al.

(10) Patent No.: US 9,611,314 B2

(45) Date of Patent: Apr. 4, 2017

(54) FUNCTIONAL PEPTIDE ANALOGS OF PEDF

(71) Applicant: The Penn State Research Foundation, University Park, PA (US)

(72) Inventors: Joyce Tombran-Tink, Parkville, MO (US); Colin J. Barnstable, Harrisburg, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/484,689

(22) Filed: Sep. 12, 2014

(65) Prior Publication Data

US 2015/0079094 A1 Mar. 19, 2015

Related U.S. Application Data

(60) Provisional application No. 61/877,335, filed on Sep. 13, 2013, provisional application No. 61/951,854, filed on Mar. 12, 2014.

(51) Int. Cl.

| | |
|---|---|
| ***A61K 38/04*** | (2006.01) |
| ***C07K 14/81*** | (2006.01) |
| ***A61K 9/00*** | (2006.01) |
| ***C07K 7/08*** | (2006.01) |
| ***C07K 16/38*** | (2006.01) |
| ***G01N 33/50*** | (2006.01) |
| ***A61K 38/55*** | (2006.01) |
| *A61K 38/00* | (2006.01) |

(52) U.S. Cl.

CPC ........ *C07K 14/8121* (2013.01); *A61K 9/0048* (2013.01); *A61K 38/55* (2013.01); *C07K 7/08* (2013.01); *C07K 16/38* (2013.01); *G01N 33/5008* (2013.01); *G01N 33/5023* (2013.01); *A61K 38/00* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 6,288,024 | B1 | 9/2001 | Bouck et al. |
| 6,391,850 | B2 | 5/2002 | Bouck et al. |
| 6,451,763 | B1 | 9/2002 | Tombran-Tink et al. |
| 6,670,333 | B2 | 12/2003 | Bouck et al. |
| 6,797,691 | B1 | 9/2004 | Bouck et al. |
| 6,919,309 | B2 | 7/2005 | Bouck et al. |
| 2006/0002978 | A1 | 1/2006 | Shea et al. |
| 2006/0008900 | A1 | 1/2006 | Chader et al. |
| 2006/0189519 | A1 | 8/2006 | Volz et al. |
| 2008/0293626 | A1 | 11/2008 | Tong et al. |
| 2009/0069241 | A1 | 3/2009 | Barnstable et al. |
| 2009/0214470 | A1 | 8/2009 | Eisenbach-Schwartz et al. |

OTHER PUBLICATIONS

Liu et al., 2012, "Pigment Epithelium-Derived Factor (PEDF) Peptide Eye Drops Reduce Inflammation, Cell Death and Vascular Leakage in Diabetic Retinopathy in Ins2$^{Akita}$ Mice ," Mol Med, 18:1387-1401.

Tombran-Tink et al., 1995, "Expression, secretion, and age-related downregulation of pigment epithelium-derived factor, a serpin with neurotrophic activity," J Neurosci. 15(7 Pt 1):4992-5003.

Tombran-Tink and Barnstable, 2003, "PEDF: a multifaceted neurotrophic factor," Nat Rev Neurosci. 4:628-636.

Cayouette et al., 1999, "Pigment epithelium-derived factor delays the death of photoreceptors in mouse models of inherited retinal degenerations," Neurobiol Dis. 6(6):523-532.

Cao et al., 2001, "In vivo protection of photoreceptors from light damage by pigment epithelium-derived factor," Invest Opthalmol Vis Sci. 42(7):1646-1652.

Mori et al., 2002, "Regression of ocular neovascularization in response to increased expression of pigment epithelium-derived factor," Invest Opthalmol V is Sci. 43:2428-34.

Wang et al., 2003, "Suppression of angiogenesis and tumor growth by adenoviral-mediated gene transfer of pigment epithelium-derived factor," Mol Ther. 2003; 8:72-79.

Abe et al., 2004, "Overexpression of pigment epithelium-derived factor decreases angiogenesis and inhibits the growth of human malignant melanoma cells in vivo," Am J Pathol. 164:1225-1232.

Bilak et al., 2002, "Identification of the Neuroprotective Molecular Region of Pigment Epithelium-Derived Factor and Its Binding Sites on Motor Neurons," J Neurosci. 22:9378-9386.

Filleur et al., 2005, "Two Functional Epitopes of Pigment Epithelial-Derived Factor Block Angiogenesis and Induce Differentiation in Prostate Cancer," Cancer Res. 65:5144-5251.

Gvritishvili et al., 2010, "Codon Preference Optimization Increases Heterologous PEDF Expression," PLoS One. 5:e15056.

Mirochnik et al., 2009, "Short PEDF-Derived Peptide Inhibits Angiogenesis and Tumor Growth," Clin. Cancer Res. 15:1655-63.

Duh et al., 2002, "Pigment Epithelium-Derived Factor Suppresses Ischemia-Induced Retinal Neovascularization and VEGF-Induced Migration and Growth," IOVS, vol. 43:821-829.

Awad et al., 2013, "Protective role of small pigment epithelium-derived factor (PEDF) peptide in diabetic renal injury," Am J Physiol Renal Physiol 305: F891-F900.

Liu et al., 2004, "Identification of the antivasopermeability effect of pigment epithelium-derived factor and its active site," PNAS, 101(17):6605-6610.

Cao et al., 1999, "Pigment epithelium-derived factor protects cultured retinal neurons against hydrogen peroxide-induced cell death," J Neurosci Res. 57(6):789-800.

Jablonski et al., 2001, "Pigment epithelium-derived factor supports normal Müller cell development and glutamine synthetase expression after removal of the retinal pigment epithelium," Glia 35(1):14-25.

Holekamp et al., 2002, "Pigment epithelium-derived factor is deficient in the vitreous of patients with choroidal neovascularization due to age-related macular degeneration," Am J Opthalmol. 134:220-227.

Becerra, 1997, "Structure-function studies on PEDF. A noninhibitory serpin with neurotrophic activity," Adv Exp Med Biol. 425:223-37.

(Continued)

*Primary Examiner* — Christine J Saoud

(74) *Attorney, Agent, or Firm* — Riverside Law LLP

(57) ABSTRACT

The invention provides compositions and methods relating to bioactive peptide analogs of PEDF.

15 Claims, 28 Drawing Sheets

(56) References Cited

OTHER PUBLICATIONS

Tombran-Tink et al., 2005, "PEDF and the serpins: phylogeny, sequence conservation, and functional domains," J Struc Biol. 151:130-150.
Li et al., 2006, "A PEDF N-terminal peptide protects the retina from ischemic injury when delivered in PLGA nanospheres," Exp. Eye. Res. 83:824-33.
GenBank Accession P36955, RecName: Full=Pigment epithelium-derived factor; Short=PEDF, Jul. 24, 2013.

Increase in the tight junction
proteins ZO1 and Occludin qPCR of cell based assay. Cultures were exposed to 25nM peptides for 48 hrs, cells harvested, mRNA isolated, and expression of ZO1 analysed; n=4; *p≤0.05; p≤0.01; *p≤0.001

10 ng of each peptide were added to 10 ul vitreous samples from mouse eyes and incubated at 37 degrees for 0-8 hrs. At each time point 1 ul sample were taken for MALDI TOF analysis Vascular Leakage after peptide treatment – 15 weeks: Albumin Immunolabeling Retinal Ganglion Cell Survival

SEQUENCE LISTING

```
<160> NUMBER OF SEQ ID NOS: 46

<210> SEQ ID NO 1
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 1

Ser Ala Leu Ser Leu Gly Ala Asp Glu Arg Thr Glu Ser Ile Ile His
1               5                   10                  15

Arg


<210> SEQ ID NO 2
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 2

Ser Ala Ile Ser Ile Gly Ala Asp Glu Arg Thr Glu Ser Ile Ile His
1               5                   10                  15

Arg


<210> SEQ ID NO 3
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 3

Ser Ala Ile Ser Ile Gly Ala Asp Ala Arg Thr Ala Ser Ile Ile His
1               5                   10                  15

Arg


<210> SEQ ID NO 4
<211> LENGTH: 29
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Butyric acid at N-terminus
<220> FEATURE:
<221> NAME/KEY: MISC_FEATURE
<222> LOCATION: (29)..(29)
<223> OTHER INFORMATION: Pegylation at C-terminus

<400> SEQUENCE: 4

Val Leu Leu Ser Pro Leu Ser Val Ala Thr Ala Leu Ser Ala Ile Ser
1               5                   10                  15

Ile Gly Ala Asp Ala Arg Thr Ala Ser Ile Ile His Arg
            20                  25
```

<210> SEQ ID NO 5
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: Butyric acid at N-terminus
<220> FEATURE:
<221> NAME/KEY: MISC_FEATURE
<222> LOCATION: (17)..(17)
<223> OTHER INFORMATION: Pegylation at C-terminus

<400> SEQUENCE: 5

Ser Ala Ile Ser Ile Gly Ala Asp Ala Arg Thr Ala Ser Ile Ile His
1 5 10 15

Arg

<210> SEQ ID NO 6
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 6

Ala Leu Tyr Tyr Asp Leu Ile Ser Ser Pro Asp Ile His Gly Thr
1 5 10 15

<210> SEQ ID NO 7
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 7

Val Leu Leu Ser Pro Leu Ser Val Ala Thr Ala Leu
1 5 10

<210> SEQ ID NO 8
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 8

Ser Ala Leu Ser Leu Gly Ala Asp Glu Arg Thr Glu Ser
1 5 10

<210> SEQ ID NO 9
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 9

Ser Ala Ile Ser Ile Gly Ala Asp Ala Arg Thr Ala Ser
1 5 10

<210> SEQ ID NO 10
<211> LENGTH: 29
<212> TYPE: PRT
<213> ORGANISM: Artificial Sequence
<220> FEATURE:
<223> OTHER INFORMATION: Chemically Synthesized

<400> SEQUENCE: 10

```
Val Leu Leu Ser Pro Leu Ser Val Ala Thr Ala Leu Ser Ala Ile Ser
1               5                   10                  15

Ile Gly Ala Asp Ala Arg Thr Ala Ser Ile Ile His Arg
            20                  25
```

<210> SEQ ID NO 11
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: Butyric acid at N-terminus
<220> FEATURE:
<221> NAME/KEY: misc_feature
<222> LOCATION: (17)..(17)
<223> OTHER INFORMATION: Pegylation at C-terminus

<400> SEQUENCE: 11

```
Ser Ala Ile Ser Ile Gly Ala Asp Glu Arg Thr Glu Ser Ile Ile His
1               5                   10                  15

Arg
```

<210> SEQ ID NO 12
<211> LENGTH: 35
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: Butyric acid at N-terminus
<220> FEATURE:
<221> NAME/KEY: misc_feature
<222> LOCATION: (35)..(35)
<223> OTHER INFORMATION: Pegylation at C-terminus

<400> SEQUENCE: 12

```
Asn Phe Gly Tyr Asp Leu Tyr Arg Val Arg Ser Ser Met Ser Pro Thr
1               5                   10                  15

Thr Asn Ser Ala Leu Ser Leu Gly Ala Asp Glu Arg Thr Glu Ser Ile
            20                  25                  30

Ile His Arg
        35
```

<210> SEQ ID NO 13
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 13

```
Ser Ala Leu Ser Leu Gly Ala Ala Glu Arg Thr Glu Ser Ile Ile His
1               5                   10                  15

Arg
```

<210> SEQ ID NO 14
<211> LENGTH: 17

-continued

<212> TYPE: PRT
<213> ORGANISM: Artificial Sequence
<220> FEATURE:
<223> OTHER INFORMATION: Chemically Synthesized

<400> SEQUENCE: 14

Ser Ala Leu Ser Leu Gly Ala Asn Glu Arg Thr Glu Ser Ile Ile His
1               5                   10                  15

Arg

<210> SEQ ID NO 15
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 15

Ser Ala Leu Ser Leu Gly Ala Asp Glu Ala Thr Glu Ser Ile Ile His
1               5                   10                  15

Arg

<210> SEQ ID NO 16
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 16

Ser Ala Asp Glu Arg Thr Glu Ser Ile Ile His Arg
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 17

Ser Ala Leu Ser Leu Phe Ala Asp Glu Arg Thr Glu Ser Ile Ile His
1               5                   10                  15

Arg

<210> SEQ ID NO 18
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (6)..(6)
<223> OTHER INFORMATION: X = L-1-NAL (L-1-naphthalene)

<400> SEQUENCE: 18

Ser Ala Leu Ser Leu Xaa Ala Asp Glu Arg Thr Glu Ser Ile Ile His
1               5                   10                  15

Arg

<210> SEQ ID NO 19
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 19

Phe Gly Ala Asp Glu Arg Thr Glu Ser Ile Ile His Arg
1 5 10

<210> SEQ ID NO 20
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: X = L-1-naphthalene

<400> SEQUENCE: 20

Xaa Gly Ala Asp Glu Arg Thr Glu Ser Ile Ile His Arg
1 5 10

<210> SEQ ID NO 21
<211> LENGTH: 51
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 21
wsngcnytnw snytnggngc ngaygarmgn acngarwsna thathcaymg n 51

<210> SEQ ID NO 22
<211> LENGTH: 53
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 22
wsngcnathw snathggngc ngaygarmgn acngarwsna thathcaymg nth 53

<210> SEQ ID NO 23
<211> LENGTH: 52
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(52)
<223> OTHER INFORMATION: n is a, c, g, t or u

<400> SEQUENCE: 23
wsngcnathw snathggngc ngaygcnmgn acngcnwsna thathcaymg nn 52

<210> SEQ ID NO 24
<211> LENGTH: 87
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:

<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u
<220> FEATURE:
<221> NAME/KEY: misc_feature
<222> LOCATION: (57)..(57)
<223> OTHER INFORMATION: n is a, c, g, t or u
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (75)..(75)
<223> OTHER INFORMATION: n is a, c, g, t or u
<220> FEATURE:
<221> NAME/KEY: misc_feature
<222> LOCATION: (87)..(87)
<223> OTHER INFORMATION: n is a, c, g, t or u

<400> SEQUENCE: 24
gtnytnytnw snccnytnws ngtngcnacn gcnytnwsng cnathwsnat hggngcngay 60
gcnmgnacng cnwsnathat hcaymgn 87

<210> SEQ ID NO 25
<211> LENGTH: 51
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 25
wsngcnathw snathggngc ngaygcnmgn acngcnwsna thathcaymg n 51

<210> SEQ ID NO 26
<211> LENGTH: 45
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (45)..(45)
<223> OTHER INFORMATION: n is a, c, g, t or u

<400> SEQUENCE: 26
gcnytntayt aygayytnat hwsnwsnccn gayathcayg gnacn 45

<210> SEQ ID NO 27
<211> LENGTH: 36
<212> TYPE: DNA

<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u

<400> SEQUENCE: 27
gtnytnytnw snccnytnws ngtngcnacn gcnytn 36

<210> SEQ ID NO 28
<211> LENGTH: 39
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u

<400> SEQUENCE: 28
wsngcnytnw snytnggngc ngaygarmgn acngarwsn 39

<210> SEQ ID NO 29
<211> LENGTH: 39
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u

<400> SEQUENCE: 29
wsngcnathw snathggngc ngaygcnmgn acngcnwsn 39

<210> SEQ ID NO 30
<211> LENGTH: 87
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u
<220> FEATURE:
<221> NAME/KEY: misc_feature
<222> LOCATION: (57)..(57)
<223> OTHER INFORMATION: n is a, c, g, t or u
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (75)..(75)
<223> OTHER INFORMATION: n is a, c, g, t or u
<220> FEATURE:
<221> NAME/KEY: misc_feature
<222> LOCATION: (87)..(87)
<223> OTHER INFORMATION: n is a, c, g, t or u

<400> SEQUENCE: 30
gtnytnytnw snccnytnws ngtngcnacn gcnytnwsng cnathwsnat hggngcngay 60
gcnmgnacng cnwsnathat hcaymgn 87

<210> SEQ ID NO 31
<211> LENGTH: 51
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 31
wsngcnathw snathggngc ngaygarmgn acngarwsna thathcaymg n 51

<210> SEQ ID NO 32

<211> LENGTH: 105
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (45)..(45)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u
<220> FEATURE:
<221> NAME/KEY: misc_feature
<222> LOCATION: (57)..(57)
<223> OTHER INFORMATION: n is a, c, g, t or u
<220> FEATURE:
<221> NAME/KEY: misc_feature
<222> LOCATION: (60)..(60)
<223> OTHER INFORMATION: n is a, c, g, t or u
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (75)..(75)
<223> OTHER INFORMATION: n is a, c, g, t or u
<220> FEATURE:
<221> NAME/KEY: misc_feature
<222> LOCATION: (84)..(84)
<223> OTHER INFORMATION: n is a, c, g, t or u
<220> FEATURE:
<221> NAME/KEY: misc_feature
<222> LOCATION: (87)..(87)
<223> OTHER INFORMATION: n is a, c, g, t or u
<220> FEATURE:
<221> NAME/KEY: misc_feature
<222> LOCATION: (93)..(93)
<223> OTHER INFORMATION: n is a, c, g, t or u
<220> FEATURE:
<221> NAME/KEY: misc_feature
<222> LOCATION: (105)..(105)
<223> OTHER INFORMATION: n is a, c, g, t or u

<400> SEQUENCE: 32
aayttyggnt aygayytnta ymgngtnmgn wsnwsnatgw snccnacnac naaywsngcn 60
ytnwsnytng gngcngayga rmgnacngar wsnathathc aymgn 105

<210> SEQ ID NO 33
<211> LENGTH: 51
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 33
wsngcnytnw snytnggngc ngcngarmgn acngarwsna thathcaymg n 51

<210> SEQ ID NO 34
<211> LENGTH: 51
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 34
wsngcnytnw snytnggngc naaygarmgn acngarwsna thathcaymg n 51

<210> SEQ ID NO 35
<211> LENGTH: 51
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 35
wsngcnytnw snytnggngc ngaygargcn acngarwsna thathcaymg n 51

<210> SEQ ID NO 36
<211> LENGTH: 36
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u

<400> SEQUENCE: 36
wsngcngayg armgnacnga rwsnathath caymgn 36

<210> SEQ ID NO 37
<211> LENGTH: 51
<212> TYPE: DNA
<213> ORGANISM: Artificial Sequence
<220> FEATURE:
<223> OTHER INFORMATION: Chemically synthesized
<220> FEATURE:

<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 37
wsngcnytnw snytnttygc ngaygarmgn acngarwsna thathcaymg n 51

<210> SEQ ID NO 38
<211> LENGTH: 15
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u

<400> SEQUENCE: 38
wsngcnytnw snytn 15

<210> SEQ ID NO 39
<211> LENGTH: 33

<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u

<400> SEQUENCE: 39
gcngaygarm gnacngarws nathathcay mgn 33

<210> SEQ ID NO 40
<211> LENGTH: 39
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u

<400> SEQUENCE: 40
ttyggngcng aygarmgnac ngarwsnath athcaymgn 39

<210> SEQ ID NO 41
<211> LENGTH: 42
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)

<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u

<400> SEQUENCE: 41
gcnytnggng cngaygarmg nacngarwsn athathcaym gn 42

<210> SEQ ID NO 42
<211> LENGTH: 44
<212> TYPE: PRT
<213> ORGANISM: Artificial Sequence
<220> FEATURE:
<223> OTHER INFORMATION: Chemically synthesized

<400> SEQUENCE: 42

```
Val Leu Leu Ser Pro Leu Ser Val Ala Thr Ala Leu Ser Ala Leu Ser
1               5                   10                  15

Leu Gly Ala Asp Glu Arg Thr Glu Ser Ile Ile His Arg Ala Leu Tyr
            20                  25                  30

Tyr Asp Leu Ile Ser Ser Pro Asp Ile His Gly Thr
        35                  40
```

<210> SEQ ID NO 43
<211> LENGTH: 132
<212> TYPE: DNA
<213> ORGANISM: Artificial Sequence
<220> FEATURE:
<223> OTHER INFORMATION: Chemically synthesized

<400> SEQUENCE: 43
gtgctgctga gcccgctgtc ggtggcaacc gcgctgagcg ctctgtcact gggcgcagat 60
gaacgtactg aatccattat tcatcgcgcg ctgtattatg acctgattag ctctccagac 120
attcatggca cc 132

<210> SEQ ID NO 44
<211> LENGTH: 29
<212> TYPE: PRT
<213> ORGANISM: Artificial Sequence
<220> FEATURE:
<223> OTHER INFORMATION: Chemically synthesized

<400> SEQUENCE: 44

```
Val Leu Leu Ser Pro Leu Ser Val Ala Thr Ala Leu Ser Ala Leu Ser
1               5                   10                  15

Leu Gly Ala Asp Glu Arg Thr Glu Ser Ile Ile His Arg
```

-continued 20 25

<210> SEQ ID NO 45
<211> LENGTH: 87
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: n is a, c, g, t or u
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (15)..(15)
<223> OTHER INFORMATION: n is a, c, g, t or u
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (24)..(24)
<223> OTHER INFORMATION: n is a, c, g, t or u
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (45)..(45)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u
<220> FEATURE:
<221> NAME/KEY: misc_feature -continued

```
<222> LOCATION: (54)..(54)
<223> OTHER INFORMATION: n is a, c, g, t or u
<220> FEATURE:
<221> NAME/KEY: misc_feature
<222> LOCATION: (57)..(57)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (75)..(75)
<223> OTHER INFORMATION: n is a, c, g, t or u
<220> FEATURE:
<221> NAME/KEY: misc_feature
<222> LOCATION: (87)..(87)
<223> OTHER INFORMATION: n is a, c, g, t or u

<400> SEQUENCE: 45

gtnytnytnw snccnytnws ngtngcnacn gcnytnwsng cnytnwsnyt nggngcngay     60

garmgnacng arwsnathat hcaymgn                                         87


<210> SEQ ID NO 46
<211> LENGTH: 35
<212> TYPE: PRT
<213> ORGANISM: Artificial Sequence
<220> FEATURE:
<223> OTHER INFORMATION: Chemically synthesized

<400> SEQUENCE: 46

Asn Phe Gly Tyr Asp Leu Tyr Arg Val Arg Ser Ser Met Ser Pro Thr
1               5                   10                  15

Thr Asn Ser Ala Leu Ser Leu Gly Ala Asp Glu Arg Thr Glu Ser Ile
            20                  25                  30

Ile His Arg
        35
```

FUNCTIONAL PEPTIDE ANALOGS OF PEDF

CROSS-REFERENCE TO RELATED APPLICATIONS

This application claims priority to U.S. Provisional Patent Application No. 61/877,335 filed Sep. 13, 2013 and U.S. Provisional Patent Application No. 61/951,854 filed Mar. 12, 2014, the contents of which are incorporated by reference herein in their entirety.

BACKGROUND OF THE INVENTION

Pigment epithelium derived factor (PEDF) is a protein that is expressed in virtually all tissues of the human body, including nerve tissues (Tombran-Tink et al., 1995, J. Neurosci. 15(7 Pt 1):4992-5003). PEDF is an angiogenesis inhibitor with neurotrophic properties and is a member of the second group of the serpin family. (Tombran-Tink and Barnstable, 2003, Nat Rev Neurosci. 4:628-636). PEDF has been shown to have protective effects which extend to neurons of the retina in particular, PEDF prevents damage to rat rod photoreceptors exposed to $H_2O_2$ or constant bright light, to rods of the retinal degeneration (rd) and retinal degeneration slow (rds) mutant mice, and to *Xenopus* rods after RPE detachment. (Cao et al., 1999, J Neurosci Res. 57(6):789-800; Cayouette et al., 1999, Neurobiol Dis. 6(6): 523-532; Cao et al., 2001, Invest Opthalmol V is Sci. 42(7):1646-1652; Jablonski et al., 2001, Glia 35(1):14-25). Furthermore, reduced expression of PEDF plays a role in eye pathologies, including retinopathy and macular degeneration (Holekamp et al., 2002, Am J. Opthalmol. 134:220-227). Increased expression of PEDF can induce regression of optical neovascularization (Mori et al., 2002, Invest Opthalmol V is Sci. 43:2428-34). PEDF expression has also been shown to control tumor growth (Wang et al., 2003, Mol. Ther. 2003; 8:72-79; Abe et al., 2004, Am J. Pathol. 164:1225-1232). Thus, PEDF has many therapeutic applications in a variety of pathologies involving angiogenesis and/or neuronal degeneration.

Human PEDF is a 46,312 Da protein, which limits the effectiveness of some forms of delivery for therapeutic applications. The options for alternative delivery systems are limited for large polypeptides such as PEDF. One way in which this problem might be overcome is to identify fragments of PEDF that maintain bioactivity. Identification of functional fragments of PEDF is therefore desirable and structure-function analysis on PEDF has been pursued (Becerra, 1997, Adv Exp Med. Biol. 425:223-37; Bilak et al., 2002, J. Neurosci. 22:9378-9386; Filleur et al., 2005, Cancer Res. 65:5144-5251; Tombran-Tink et al., 2005, J Struc Biol. 151:130-150).

The neuroprotective and antiangiogenic activities of PEDF have been localized to two short adjacent n-terminal fragments of the gene (Li et al., 2006, Exp. Eye. Res. 83:824-33; Gvritishvili et al., 2010, PLoS One. 5:e15056; Bilak et al., 2002, J. Neurosci. 22:9378-86; Mirochnik et al., 2009, Clin. Cancer Res. 15:1655-63).

Given the various potential therapeutic uses of PEDF there is a need in the art for molecules retaining the therapeutic activities of full-length PEDF but which are smaller in size and are easily administrable. The present invention addresses this need.

SUMMARY OF THE INVENTION

In one aspect, the present invention provides a composition comprising at least one peptide analog of pigment epithelium derived factor (PEDF). In one embodiment, the at least one peptide analog comprises at least one selected from the group consisting of SpxA1 (SEQ ID NO: 44), 81-1 (SEQ ID NO: 1), 81-2 (SEQ ID NO: 2), 81-3 (SEQ ID NO: 3), 81-4 (SEQ ID NO: 4), 81-5 (SEQ ID NO: 5), 81-6 (SEQ ID NO: 6), 81-7 (SEQ ID NO: 7), 81-8 (SEQ ID NO: 8), 81-9 (SEQ ID NO: 9), 81-10 (SEQ ID NO: 10), 81-11 (SEQ ID NO: 11), 81-12 (SEQ ID NO: 12), 81-13 (SEQ ID NO: 12), 81-14 (SEQ ID NO: 14), 81-15 (SEQ ID NO: 15), 81-16 (SEQ ID NO: 16), 81-17 (SEQ ID NO: 17), 81-18 (SEQ ID NO: 18), 81-19 (SEQ ID NO: 19), and 81-20 (SEQ ID NO: 20).

In one embodiment, the composition further comprises a pharmaceutical carrier. In one embodiment, the composition reduces at least one of inflammation, the level of pro-inflammatory cytokines, cell death, vascular leakage, and macular edema.

In one embodiment, the at least one peptide analog comprises at least one peptide analog selected from the group consisting of SpxA1 (SEQ ID NO: 44), 81-2 (SEQ ID NO: 2), 81-5 (SEQ ID NO: 5), 81-12 (SEQ ID NO: 12), 81-13 (SEQ ID NO: 13), and 81-20 (SEQ ID NO: 20).

In one embodiment, the composition is selected from the group consisting of an eye drop, a gel, a foam, an injectate, and a cell. In one embodiment, the composition is configured for delivery to the eye of a subject.

In one aspect the present invention provides a composition comprising at least one isolated nucleic acid encoding at least one peptide analog of PEDF or portion thereof. In one embodiment, the at least one peptide analog comprises at least one selected from the group consisting of SpxA1 (SEQ ID NO: 44), 81-1 (SEQ ID NO: 1), 81-2 (SEQ ID NO: 2), 81-3 (SEQ ID NO: 3), 81-4 (SEQ ID NO: 4), 81-5 (SEQ ID NO: 5), 81-6 (SEQ ID NO: 6), 81-7 (SEQ ID NO: 7), 81-8 (SEQ ID NO: 8), 81-9 (SEQ ID NO: 9), 81-10 (SEQ ID NO: 10), 81-11 (SEQ ID NO: 11), 81-12 (SEQ ID NO: 12), 81-13 (SEQ ID NO: 12), 81-14 (SEQ ID NO: 14), 81-15 (SEQ ID NO: 15), 81-16 (SEQ ID NO: 16), 81-17 (SEQ ID NO: 17), 81-18 (SEQ ID NO: 18), 81-19 (SEQ ID NO: 19), and 81-20 (SEQ ID NO: 20).

In one embodiment, the at least one isolated nucleic acid comprises at least one nucleotide sequence selected from the group consisting of SEQ ID NO: 45, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In one embodiment, the composition further comprises a pharmaceutical carrier. In one embodiment, the composition reduces at least one of inflammation, the level of pro-inflammatory cytokines, cell death, vascular leakage, and macular edema.

In one embodiment, the at least one peptide analog comprises at least one peptide analog selected from the group consisting of SpxA1 (SEQ ID NO: 44), 81-2 (SEQ ID NO: 2), 81-5 (SEQ ID NO: 5), 81-12 (SEQ ID NO: 12), 81-13 (SEQ ID NO: 13), and 81-20 (SEQ ID NO: 20). In one embodiment, the at least one isolated nucleic acid comprises at least one nucleotide sequence selected from the group consisting of SEQ ID NO: 45, SEQ ID NO: 22, SEQ ID NO: 25, SEQ ID NO: 32, SEQ ID NO: 33, and SEQ ID NO: 41.

In one embodiment, the composition is selected from the group consisting of an eye drop, a gel, a foam, a virus, an expression vector, an injectate, and a cell. In one embodiment, the composition is configured for delivery to the eye of a subject.

In one aspect, the present invention provides a method for treating a disease or disorder in a subject, the method comprising administering to a subject a therapeutically effective amount of a composition comprising at least one peptide analog of PEDF or isolated nucleic acid encoding the same. In one embodiment, the at least one peptide analog comprises at least one selected from the group consisting of SpxA1 (SEQ ID NO: 44), 81-2 (SEQ ID NO: 2), 81-5 (SEQ ID NO: 5), 81-12 (SEQ ID NO: 12), 81-13 (SEQ ID NO: 13) and 81-20 (SEQ ID NO: 20).

In one embodiment, the method reduces at least one of inflammation, the level of pro-inflammatory cytokines, cell death, vascular leakage, and macular edema, in the subject.

In one embodiment, the composition is administered by a method selected from the group consisting of administration as an eye drop, administration by intraocular injection, administration as a gel to the eye, administration as an implant in the eye that releases the peptide over time, administration as a virus that expresses the peptide, and administration using a cell-based expression system.

In one embodiment, the disease or disorder is associated with angiogenesis. In one embodiment, the disease or disorder is selected from the group consisting of diabetic retinopathy, retinopathy of prematurity, age-related macular degeneration, retinitis pigmentosis, glaucoma, uveitis, corneal inflammation, diabetes, a neurodegenerative disease, nerve injury, sepsis, acute respiratory distress syndrome, nephrotic syndrome, diabetic neuropathy, preproliferative diabetic retinopathy, proliferative diabetic retinopathy, cancer, and cystic fibrosis.

In one embodiment, the subject is a mammal. In one embodiment, the mammal is a human.

In one aspect the present invention provides a method of reducing the level of VEGF in a subject, comprising administering to a subject a composition comprising at least one peptide analog of PEDF or isolated nucleic acid encoding the same. In one embodiment, the at least one peptide analog comprises at least one selected from the group consisting of 81-2 (SEQ ID NO: 2), 81-5 (SEQ ID NO: 5), 81-10 (SEQ ID NO: 10), 81-12 (SEQ ID NO: 12), 81-13 (SEQ ID NO: 13), 81-19 (SEQ ID NO: 19) and 81-20 (SEQ ID NO: 20).

In one aspect, the present invention provides a biological assay comprising contacting a cell with a composition comprising at least one peptide analog of PEDF, wherein the at least one peptide analog comprises at least one selected from the group consisting of SpxA1 (SEQ ID NO: 44), 81-1 (SEQ ID NO: 1), 81-2 (SEQ ID NO: 2), 81-3 (SEQ ID NO: 3), 81-4 (SEQ ID NO: 4), 81-5 (SEQ ID NO: 5), 81-6 (SEQ ID NO: 6), 81-7 (SEQ ID NO: 7), 81-8 (SEQ ID NO: 8), 81-9 (SEQ ID NO: 9), 81-10 (SEQ ID NO: 10), 81-11 (SEQ ID NO: 11), 81-12 (SEQ ID NO: 12), 81-13 (SEQ ID NO: 12), 81-14 (SEQ ID NO: 14), 81-15 (SEQ ID NO: 15), 81-16 (SEQ ID NO: 16), 81-17 (SEQ ID NO: 17), 81-18 (SEQ ID NO: 18), 81-19 (SEQ ID NO: 19), and 81-20 (SEQ ID NO: 20).

In one embodiment, the assay comprises contacting the cell with a liquid medium comprising the at least one peptide analog. In one embodiment the assay comprises contacting a cell with an isolated nucleic acid encoding the at least one peptide analog and wherein the cell secretes the at least one peptide analog.

In one embodiment, the assay comprises detecting the effect of the composition on at least one selected from the group consisting of inflammation, cell death, vascular leakage, tumor growth, apoptosis, cytoskeletal function, mitochondrial function, oxidative stress, angiogenesis, neurogenesis, cell growth, immune function, cell differentiation, adipogenesis, bone deposition, and gene expression. In one embodiment, the assay further comprises contacting the cell with a test compound.

In one aspect, the present invention provides a method of generating an antibody, comprising immunizing a subject with a composition comprising at least one immunogenic peptide analog of PEDF or isolated nucleic acid encoding the same under conditions suitable for eliciting an immune response, and recovering an antibody from the subject, wherein the at least one immunogenic peptide analog comprises at least one selected from the group consisting of SpxA1 (SEQ ID NO: 44), 81-1 (SEQ ID NO: 1), 81-2 (SEQ ID NO: 2), 81-3 (SEQ ID NO: 3), 81-4 (SEQ ID NO: 4), 81-5 (SEQ ID NO: 5), 81-6 (SEQ ID NO: 6), 81-7 (SEQ ID NO: 7), 81-8 (SEQ ID NO: 8), 81-9 (SEQ ID NO: 9), 81-10 (SEQ ID NO: 10), 81-11 (SEQ ID NO: 11), 81-12 (SEQ ID NO: 12), 81-13 (SEQ ID NO: 12), 81-14 (SEQ ID NO: 14), 81-15 (SEQ ID NO: 15), 81-16 (SEQ ID NO: 16), 81-17 (SEQ ID NO: 17), 81-18 (SEQ ID NO: 18), 81-19 (SEQ ID NO: 19), and 81-20 (SEQ ID NO: 20). In one embodiment, the antibody binds to PEDF or a fragment thereof.

In one embodiment, the present invention provides an antibody that specifically binds to a peptide, wherein the peptide comprises at least one of the group consisting of PEDF, a fragment of PEDF, and an analog of PEDF. In one embodiment, the peptide is a peptide analog selected from the group consisting of SpxA1 (SEQ ID NO: 44), 81-1 (SEQ ID NO: 1), 81-2 (SEQ ID NO: 2), 81-3 (SEQ ID NO: 3), 81-4 (SEQ ID NO: 4), 81-5 (SEQ ID NO: 5), 81-6 (SEQ ID NO: 6), 81-7 (SEQ ID NO: 7), 81-8 (SEQ ID NO: 8), 81-9 (SEQ ID NO: 9), 81-10 (SEQ ID NO: 10), 81-11 (SEQ ID NO: 11), 81-12 (SEQ ID NO: 12), 81-13 (SEQ ID NO: 12), 81-14 (SEQ ID NO: 14), 81-15 (SEQ ID NO: 15), 81-16 (SEQ ID NO: 16), 81-17 (SEQ ID NO: 17), 81-18 (SEQ ID NO: 18), 81-19 (SEQ ID NO: 19), and 81-20 (SEQ ID NO: 20).

In one embodiment, the present invention provides a method of culturing a stem cell comprising contacting the stem cell with at least one peptide analog of PEDF. In one embodiment, the at least peptide analog comprises at least one selected from the group consisting of SpxA1 (SEQ ID NO: 44), 81-1 (SEQ ID NO: 1), 81-2 (SEQ ID NO: 2), 81-3 (SEQ ID NO: 3), 81-4 (SEQ ID NO: 4), 81-5 (SEQ ID NO: 5), 81-6 (SEQ ID NO: 6), 81-7 (SEQ ID NO: 7), 81-8 (SEQ ID NO: 8), 81-9 (SEQ ID NO: 9), 81-10 (SEQ ID NO: 10), 81-11 (SEQ ID NO: 11), 81-12 (SEQ ID NO: 12), 81-13 (SEQ ID NO: 12), 81-14 (SEQ ID NO: 14), 81-15 (SEQ ID NO: 15), 81-16 (SEQ ID NO: 16), 81-17 (SEQ ID NO: 17), 81-18 (SEQ ID NO: 18), 81-19 (SEQ ID NO: 19), and 81-20 (SEQ ID NO: 20).

In one embodiment, the method comprises contacting the cell with a liquid medium comprising the at least one peptide analog. In one embodiment, the method comprises contacting a cell with an isolated nucleic acid encoding the at least one peptide analog and wherein the cell secretes the at least one peptide analog.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising (FIG. 2A) serum starvation; (FIG. 2B) oxidative stress caused by hydrogen peroxide toxicity (300 μM).

FIG. 3, comprising

FIG. 4, comprising

FIG. 12A through FIG. 12F, is a set of images of retinal sections of diabetic mice labeled for albumin. FIG. 12A (40×) depicts increased albumin levels in the photoreceptor inner and outer segment areas and vascular leakage into the retinal parenchyma in the outer plexiform layers. FIG. 12B (40×), FIG. 12C (40×), FIG. 12E (80×) and FIG. 12F (80×) depict vascular leakage in the retinal ganglion layer. FIG. 12D (40×) depicts albumin in a large blood vessel in the retinal ganglion layer.

FIG. 16, comprising

FIG. 18, comprising

DETAILED DESCRIPTION OF THE INVENTION

Figure 1:
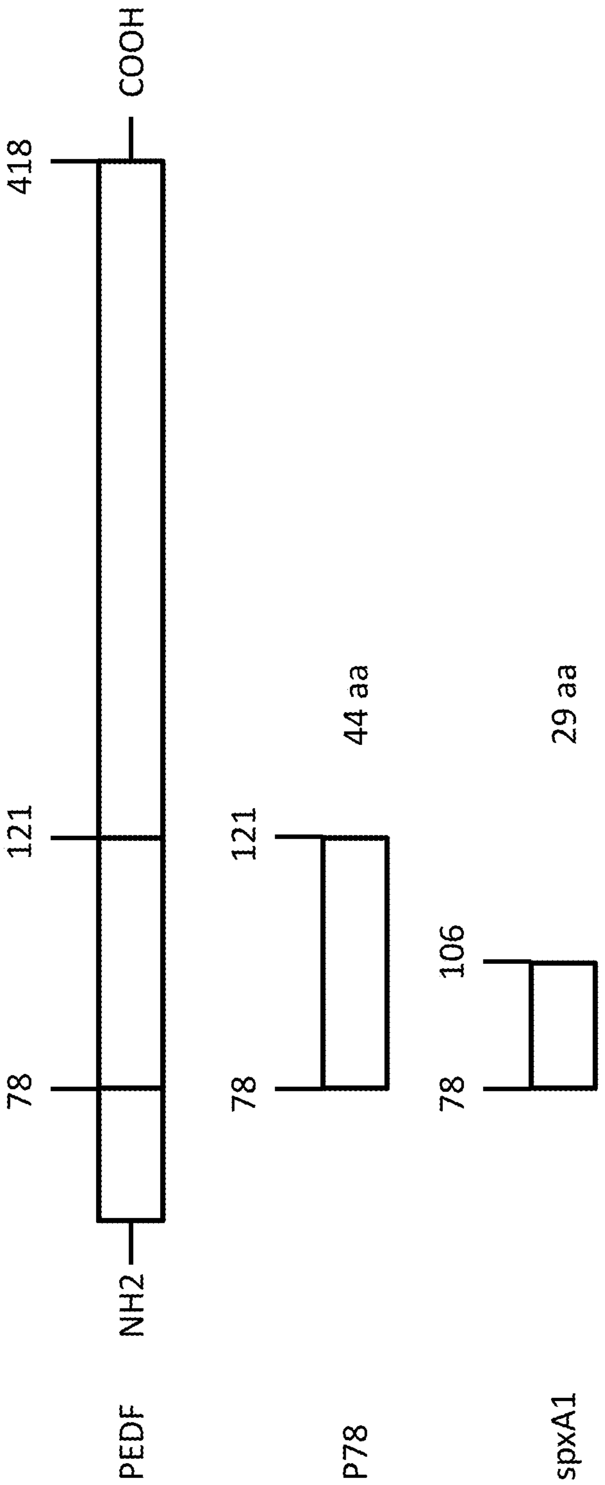
FIG. 1 is a schematic of PEDF, P78 and spxA1.

The present invention provides peptide analogs of PEDF and uses thereof. The invention is based in part on the discovery that peptides and peptide analogs based on p78, a 44 residue peptide from PEDF (residues 78 to 121 see FIG. 1) retain various desirable therapeutic properties and modifications and/or changes to the natural sequence provides peptides with enhanced therapeutic benefits. Accordingly, the invention provides compositions comprising small functional peptide analogs of PEDF and uses thereof.

In particular, the present invention is based on the discovery that peptide analogs based on the active p78 fragment of PEDF, including certain peptides having internal amino acids substitutions, hydrophobic caps and modifications to support helix stabilization have desired activities of PEDF and in some cases have enhanced activity. In one embodiment, peptides of the present invention are provided in Table 1 and are referred to herein as SpxA1 and 81-1 to 81-20.

The invention provides compositions comprising peptide analogs and/or isolated nucleic acids encoding peptide analogs useful for a wide variety of applications. The invention also provides methods of using the compositions as well as kits containing the compositions. The small peptides of the invention allow relative ease in crossing tissue barriers, can be synthesized in reproducibly pure large-scale quantities, and result in fewer side effects compared to full length PEDF. In certain embodiments the compositions of the invention can be prepared and administered as eye drops which provide major advantages over prior art treatment methods.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2005, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof, are used for chemical syntheses and chemical analyses.

As used herein, amino acids are represented by the full name thereof, by the three-letter code as well as the one-letter code corresponding thereto:

| Full Name | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, a disease or disorder is "alleviated" if the severity of a symptom of the disease or disorder, the frequency with which such a symptom is experienced by a patient, or both, are reduced.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the terms "conservative variation" or "conservative substitution" as used herein refers to the replacement of an amino acid residue by another, biologically similar residue. Conservative variations or substitutions are not likely to substantially change the shape and/or activity of the peptide chain. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Instructional material," as that term is used herein, includes a publication, a recording, a diagram, or any other medium of expression which can be used to communicate the usefulness of the nucleic acid, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

By the term "modulating," as used herein, is meant mediating a detectable increase or decrease in the level of a mRNA, polypeptide, or a response in a subject compared with the level of a mRNA, polypeptide or a response in the subject in the absence of a treatment or compound, and/or compared with the level of a mRNA, polypeptide, or a response in an otherwise identical but untreated subject. The term encompasses perturbing and/or affecting a native signal or response thereby mediating a beneficial therapeutic response in a subject, preferably, a human.

"Neurotrophic activity" as used herein is the ability to enhance survival and/or growth of neuronal cell populations. Neuroprotective activity, such as delaying or reducing neuronal apoptosis, is encompassed by the term neurotrophic activity.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

By describing two peptides or polypeptides as "operably fused" is meant that the structure and/or biological activity of each individual peptide is also present in the fusion.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, a "peptidomimetic" is a compound containing non-peptidic structural elements that is capable of mimicking the biological action of a parent peptide. A peptidomimetic may or may not comprise peptide bonds.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

A "prophylactic" treatment is a treatment administered to a subject who does not exhibit signs of a disease or exhibits only early signs of the disease for the purpose of decreasing the risk of developing pathology associated with the disease.

By the term "retinopathy" as used herein, is meant the abnormal development of blood vessels within or around the retina that may or may not enter the vitreous. Injury, disease, ischemic events, laser or other iatrogenic treatments may induce retinopathy.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal peptide is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

The term "substantially pure" describes a compound, e.g., a protein or polypeptide, which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides, by column chromatography, gel electrophoresis or HPLC analysis. A compound, e.g., a protein, is also substantially purified when it is essentially free of naturally associated components or when it is separated from the native contaminants which accompany it in its natural state.

As used herein, the term "substantially the same" amino acid sequence is defined as a sequence with at least 70%, preferably at least about 80%, more preferably at least about 85%, more preferably at least about 90%, even more preferably at least about 95%, and most preferably at least 99% homology with another amino acid sequence, as determined by the FASTA search method in accordance with Pearson & Lipman, 1988, Proc. Natl. Inst. Acad. Sci. USA 85:2444-48.

By the term "specifically bind" or "specifically binds," as used herein, is meant that a first molecule preferentially binds to a second molecule, but does not necessarily bind only to that second molecule.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to peptide analogs of PEDF and uses thereof. For example, in certain instances the invention provides peptides and peptide analogs based on smaller active fragments of P78, a 44 residue peptide from PEDF (residues 78 to 121), wherein the peptides, including peptides and analogs, fragments, and derivatives thereof, of the invention exhibit desirable therapeutic properties. In one embodiment, the invention provides compositions comprising peptides and analogs, fragments, and derivatives thereof that exhibit one or more of improved efficacy, half-life, bioavailability, and the like compared to full length PEDF. In one embodiment, the composition comprises a peptide comprising butyric acid at the N-terminus. In one embodiment the composition comprises a peptide being Pegylated at the C-terminus. For example, in one embodiment, the peptide comprises Fmoc-NH-$PEG_2$-$CH_2COOH$ at the C-terminus. In one embodiment, the invention provides isolated nucleic acids encoding the peptides disclosed herein.

The invention provides peptide analogs of PEDF useful for a wide variety of applications. The invention also provides methods of using the peptides as well as kits containing the peptides. The small peptides of the invention advantageously allow the relative ease of crossing tissue barriers, of providing active doses, of ease of synthesis in reproducibly pure large-scale quantities, and fewer side effects, compared to full length PEDF.

In another embodiment, the invention provides methods of using the compositions of the invention in any therapeutic or prophylactic treatment known in the art, or subsequently discovered, that have been used with full-length PEDF protein. Such therapeutic applications are disclosed in detail in, for instance, U.S. Pat. Nos. 6,451,763; 6,288,024; 6,391,850; 6,670,333; 6,797,691; 6,919,309 and U.S. Patent Publication 20060008900, each of which is enclosed herein in its entirety.

Compositions

The invention provides isolated peptides and nucleic acids encoding such peptides. Also provided are vectors and cells comprising an isolated nucleic acid of the invention. The peptides, including peptides and analogs, fragments, and derivatives thereof are based on smaller active fragments of P78, a 44 residue peptide from PEDF (residues 78 to 121). In certain embodiments, the peptides of the invention are human.

Exemplary peptides of the present invention are illustrated in Table 1 and are identified as SpxA1 and 81-1 to 81-20. SpxA1, also referred to herein as "Spx," comprises amino acid residues 78 to 106 of PEDF. In one embodiment, the amino acid sequence of SpxA is provided by SEQ ID NO: 44. The amino acid sequences for peptides 81-1 through 81-20 are provided by SEQ ID NOs: 1 through 20, respectively. In one embodiment, the composition comprises an isolated nucleic acid encoding a peptide of the invention. For example, in one embodiment, the composition comprises an isolated nucleic acid encoding a peptide having an amino acid sequence of one of SEQ ID NOs 1 through 20 or SEQ ID NO: 44.

In one embodiment, the invention includes variants of the peptides of the invention. In one embodiment, variants differ from naturally-occurring peptides by conservative amino acid sequence differences or by modifications which do not affect sequence, or by both. For example, conservative amino acid changes may be made, which although they alter the primary sequence of the peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

In one embodiment, the peptide of the invention comprises a peptide having at least 75% homology with a peptide listed in Table 1 (i.e. peptides 81-1 to 81-20). In one embodiment, the peptide of the invention comprises a peptide having at least 80% homology with a peptide listed in Table 1. In one embodiment, the peptide of the invention comprises a peptide having at least 85% homology with a peptide listed in Table 1. In one embodiment, the peptide of the invention comprises a peptide having at least 90% homology with a peptide listed in Table 1. In one embodiment, the peptide of the invention comprises a peptide having at least 95% homology with a peptide listed in Table 1. In one embodiment, the peptide of the invention comprises a peptide having at least 99% homology with a peptide listed in Table 1.

In a further embodiment, the peptide of the invention comprise D-, L-, and unnatural isomers of amino acids. In one embodiment, the composition comprises a peptide comprising one or more unnatural or non-natural amino acids. Non-natural amino acids include, but are not limited to, the D-amino acids, 2,4-diaminobutyric acid, α-amino isobutyric acid, 2-aminoisobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, naphthalene, L-1-naphthalene, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general.

As known in the art the "similarity" between two peptides is determined by comparing the amino acid sequence and its conserved amino acid substitutes of one polypeptide to a sequence of a second peptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

In certain embodiments, the peptides of the invention comprise an N-terminal and/or C-terminal modifications that in certain instances improve activity. For example, in one embodiment, the peptide of the invention comprises a butyric acid at the N-terminus of the peptide. In one embodiment, the peptide is PEGylated at the C-terminus of the peptide. The present invention encompasses variants of the peptide analogs, including those with terminal modifications, without terminal modifications, or having different terminal modifications.

For example, in one embodiment, the composition of the invention comprises 81-12 ({BA*}NFGYDLYRVRSSMSPTTNSALSLGADERTESII HR {PEG*}; SEQ ID NO:12), a peptide having a butyric acid at the N-terminus and PEGylated at the C-terminus. However, the present invention also encompasses analogs and derivatives of 81-12, including peptides having different terminal modifications or no terminal modifications. That is, the present invention encompasses a composition comprising a peptide comprising the amino acid sequence of NFGYDLYRVRSSMSPTTNSALSLGADERTESIIHR (SEQ ID NO: 46), or an isolated nucleic acid encoding SEQ ID NO: 46. Similarly, the present invention encompasses variants of Spx, and 81-1 to 81-20, including variants with alternative N-terminal and/or C-terminal modifications.

Variants of suitable peptides of the invention can also be expressed. Variants may be made by, for example, the deletion, addition, or alteration of amino acids that have either (i) minimal influence on certain properties, secondary structure, and hydropathic nature of the polypeptide or (ii) substantial effect on one or more properties of the peptide mimetics of the invention.

Variants may also include, for example, a peptide conjugated to a linker or other sequence for ease of synthesis, purification, identification, or therapeutic use (i.e., delivery) of the peptide.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA ($tRNA_{LYS}$), could be modified with an amine specific photoaffinity label.

The peptides of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide of the invention.

Cyclic derivatives of the peptides the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Peptides of the invention may also have modifications. Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties or to render them more suitable as a therapeutic agent. Such variants include those containing residues other than naturally-occurring L-amino acids, e.g., D-amino acids or non-naturally-occurring synthetic amino acids. The peptides of the invention may further be conjugated to non-amino acid moieties that are useful in their therapeutic application. In particular, moieties that improve the stability, biological half-life, water solubility, and/or immunologic characteristics of the peptide are useful. A non-limiting example of such a moiety is polyethylene glycol (PEG).

Covalent attachment of biologically active compounds to water-soluble polymers is one method for alteration and control of biodistribution, pharmacokinetics, and often, toxicity for these compounds (Duncan et al., 1984, Adv. Polym. Sci. 57:53-101). Many water-soluble polymers have been used to achieve these effects, such as poly(sialic acid), dextran, poly(N-(2-hydroxypropyl)methacrylamide) (PHPMA), poly(N-vinylpyrrolidone) (PVP), poly(vinyl alcohol) (PVA), poly(ethylene glycol-co-propylene glycol), poly(N-acryloyl morpholine (PAcM), and poly(ethylene glycol) (PEG) (Powell, 1980, Polyethylene glycol. In R. L. Davidson (Ed.) Handbook of Water Soluble Gums and Resins. McGraw-Hill, New York, chapter 18). PEG possess an ideal set of properties: very low toxicity (Pang, 1993, J. Am. Coll. Toxicol. 12: 429-456) excellent solubility in aqueous solution (Powell, supra), low immunogenicity and antigenicity (Dreborg et al., 1990, Crit. Rev. Ther. Drug Carrier Syst. 6: 315-365). PEG-conjugated or "PEGylated" protein therapeutics, containing single or multiple chains of polyethylene glycol on the protein, have been described in the scientific literature (Clark et al., 1996, J. Biol. Chem. 271: 21969-21977; Hershfield, 1997, Biochemistry and immunology of poly(ethylene glycol)-modified adenosine deaminase (PEG-ADA). In J. M. Harris and S. Zalipsky (Eds) Poly(ethylene glycol): Chemistry and Biological Applications. American Chemical Society, Washington, D.C., p 145-154; Olson et al., 1997, Preparation and characterization of poly(ethylene glycol)ylated human growth hormone antagonist. In J. M. Harris and S. Zalipsky (Eds) Poly(ethylene glycol): Chemistry and Biological Applications. American Chemical Society, Washington, D.C., p 170-181).

A peptide of the invention may be synthesized by conventional techniques. For example, the peptides of the invention may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.)

The peptides may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purities, i.e., purities sufficient for research, diagnostic or therapeutic purposes.

Solid phase peptide synthesis is described by Stewart et al. in Solid Phase Peptide Synthesis, 2nd Edition, 1984, Pierce Chemical Company, Rockford, Ill.; and Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group, such as formation into a carbodiimide, a symmetric acid anhydride, or an "active ester" group, such as hydroxybenzotriazole or pentafluorophenyl esters.

Examples of solid phase peptide synthesis methods include the BOC method which utilized tert-butyloxcarbonyl as the alpha-amino protecting group, and the FMOC method which utilizes 9-fluorenylmethyloxcarbonyl to protect the alpha-amino of the amino acid residues, both which methods are well-known by those of skill in the art.

Incorporation of N- and/or C-blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function, e.g. with DCC, can then proceed by addition of the desired alcohol, followed by deprotection and isolation of the esterified peptide product.

In one embodiment, the peptides of the invention are manufactured by solid phase peptide synthesis using Fmoc chemistry. In certain embodiments, after synthesis the Fmoc group is deprotected at the N-terminus, the side chain protection group is deprotected, and the peptide is cleaved from the resin. In one embodiment, the resin is a Cl-resin. In one embodiment, the condensation reaction reagent is DIC+HOBT. In one embodiment deprotection is done using Pip. In certain embodiments, the synthesized peptides are purified by RP-HPLC using a solvent of acetonitrile+deionized with TFA as the buffer. In one embodiment, the peptides are purified by gradient elution.

The peptides of the invention may be prepared by standard chemical or biological means of peptide synthesis. Biological methods include, without limitation, expression of a nucleic acid encoding a peptide in a host cell or in an in vitro translation system.

Included in the invention are nucleic acid sequences that encode the peptide of the invention. In one embodiment, the invention includes nucleic acid sequences corresponding to the amino acid sequences of any one of the peptides listed in Table 1. Accordingly, subclones of a nucleic acid sequence encoding a peptide of the invention can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (2012), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity.

Biological preparation of a peptide of the invention involves expression of a nucleic acid encoding a desired peptide. An expression cassette comprising such a coding sequence may be used to produce a desired peptide for use in the method of the invention.

In the context of an expression vector, the vector can be readily introduced into a host cell, e.g., mammalian, bacterial, yeast or insect cell by any method in the art. Coding sequences for a desired peptide of the invention may be codon optimized based on the codon usage of the intended host cell in order to improve expression efficiency as demonstrated herein. Codon usage patterns can be found in the literature (Nakamura et al., 2000, Nuc Acids Res. 28:292). Representative examples of appropriate hosts include bacterial cells, such as streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The expression vector can be transferred into a host cell by physical, biological or chemical means, discussed in detail elsewhere herein.

Examples of biological methods to prepare the peptides of the present invention may utilize methods provided in published US Patent application number US 2009/0069241, which is incorporated herein in its entirety.

To ensure that the peptide obtained from either chemical or biological synthetic techniques is the desired peptide, analysis of the peptide composition can be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

In one embodiment, the present invention provides a composition comprising an isolated nucleic acid encoding a PEDF derived peptide, or a fragment thereof. In one embodiment, the isolated nucleic acid encodes a peptide comprising an amino acid sequence selected from SEQ ID NO: 44 and SEQ ID NOs: 1-20. Further, the invention encompasses an isolated nucleic acid encoding a peptide having substantial homology to a peptide disclosed herein. In certain embodiments, the isolated nucleic acid sequence encodes a peptide having at least 75%, 80%, 85%, 90%, 95%, 96%, 97%, 98%, or 99% sequence homology with an amino acid sequence selected from SEQ ID NO: 44 and SEQ ID NOs: 1-20.

The nucleic acid sequence encoding the SpxA1 peptide is provided SEQ ID NO: 45. Nucleic acid sequences encoding peptides 81-1 to 81-20, or portions thereof, are provided by SEQ ID NOs 21-41. The nucleic acid sequence encoding peptide 81-1 is provided SEQ ID NO: 21. The nucleic acid sequence encoding peptide 81-2 is provided SEQ ID NO: 22. The nucleic acid sequence encoding peptide 81-3 is provided SEQ ID NO: 23. The nucleic acid sequence encoding peptide 81-4 is provided SEQ ID NO: 24. The nucleic acid sequence encoding peptide 81-5 is provided SEQ ID NO: 25. The nucleic acid sequence encoding peptide 81-6 is provided SEQ ID NO: 26. The nucleic acid sequence encoding peptide 81-7 is provided SEQ ID NO: 27. The nucleic acid sequence encoding peptide 81-8 is provided SEQ ID NO: 28. The nucleic acid sequence encoding peptide 81-9 is provided SEQ ID NO: 29. The nucleic acid sequence encoding peptide 81-10 is provided SEQ ID NO: 30. The nucleic acid sequence encoding peptide 81-11 is provided SEQ ID NO: 31. The nucleic acid sequence encoding peptide 81-12 is provided SEQ ID NO: 32. The nucleic acid sequence encoding peptide 81-13 is provided SEQ ID NO: 13. The nucleic acid sequence encoding peptide 81-14 is provided SEQ ID NO: 34. The nucleic acid sequence encoding peptide 81-15 is provided SEQ ID NO: 35. The nucleic acid sequence encoding peptide 81-16 is provided SEQ ID NO: 36. The nucleic acid sequence encoding peptide 81-17 is provided SEQ ID NO: 37. The nucleic acid sequences encoding peptide 81-18 is provided SEQ ID NO: 38 and SEQ ID NO: 39. The nucleic acid sequence encoding peptide 81-19 is provided SEQ ID NO: 40. The nucleic acid sequence encoding peptide 81-20 is provided SEQ ID NO: 41.

For example, in one embodiment, the isolated nucleic acid comprises a nucleotide sequence selected from SEQ ID NOs: 21-41. Further, the invention encompasses an isolated nucleic acid having substantial homology to a nucleic acid disclosed herein. In certain embodiments, the isolated nucleic acid has at least 75%, 80%, 85%, 90%, 95%, 96%, 97%, 98%, or 99% sequence homology with a nucleotide sequence selected from SEQ ID NO: 45 and SEQ ID NOs: 21-41.

The isolated nucleic acid may comprise any type of nucleic acid, including, but not limited to DNA and RNA. For example, in one embodiment, the composition comprises an isolated DNA molecule, including for example, an isolated cDNA molecule, encoding a peptide of the invention, or functional fragment thereof. In one embodiment, the composition comprises an isolated RNA molecule encoding a peptide of the invention, or a functional fragment thereof. The isolated nucleic acids may be synthesized using any method known in the art.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-β-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (*Nucleic Acids Res.,* 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

Vectors

The present invention also includes a vector in which the isolated nucleic acid of the present invention is inserted. The art is replete with suitable vectors that are useful in the present invention.

In brief summary, the expression of natural or synthetic nucleic acids encoding a peptide is typically achieved by operably linking a nucleic acid encoding the peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of the peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention includes a composition comprising a cell which comprises a peptide of the invention, a nucleic acid encoding a peptide of the invention, or a combination thereof. In one embodiment, the cell is genetically modified to comprise a peptide and/or nucleic acid of the invention. In certain embodiments, genetically modified cell is autologous to a subject being treated with the composition of the invention. Alternatively, the cells can be allogeneic, syngeneic, or xenogeneic with respect to the subject. In certain embodiment, the cell is able to secrete or release the expressed peptide of the invention into extracellular space in order to deliver the peptide to one or more other cells.

The genetically modified cell may be modified in vivo or ex vivo, using techniques standard in the art. Genetic modification of the cell may be carried out using an expression vector or using a naked isolated nucleic acid construct.

In one embodiment, the cell is obtained and modified ex vivo, using an isolated nucleic acid encoding a peptide. In one embodiment, the cell is obtained from a subject, genetically modified to express the peptide and/or nucleic acid, and is re-administered to the subject. In certain embodiments, the cell is expanded ex vivo or in vitro to produce a population of cells, wherein at least a portion of the population is administered to a subject in need.

In one embodiment, the cell is genetically modified to stably express the peptide. In another embodiment, the cell is genetically modified to transiently express the peptide.

The present invention provides a scaffold or substrate composition comprising a peptide of the invention, an isolated nucleic acid of the invention, a cell comprising the peptide of the invention, or a combination thereof. For example, in one embodiment, a peptide of the invention, an isolated nucleic acid of the invention, a cell producing the peptide of the invention, or a combination thereof is incorporated within a scaffold. In another embodiment, a peptide of the invention, an isolated nucleic acid of the invention, a cell producing the peptide of the invention, or a combination thereof is applied to the surface of a scaffold. The scaffold of the invention may be of any type known in the art. Non-limiting examples of such a scaffold includes a, hydrogel, electrospun scaffold, foam, mesh, sheet, patch, and sponge.

Methods

The peptides disclosed herein are useful in any method known in the art, or subsequently discovered, where PEDF protein is useful. For example, the peptides of the invention and nucleic acids encoding the peptides may be used in biological assays, screening assays, therapeutic treatments, prophylactic treatments, culture media supplements, and the like.

Assays

In one embodiment, the peptides of the invention are used in a biological assay. For example, the one or more of the peptides of the invention may be used to screen for tumor growth, apoptosis, cytoskeletal function, function of mitochondrial and other organelles, oxidative stress, inflammation, angiogenesis, neurogenesis, cell growth, immune function, cell differentiation, adipogenesis, and bone deposition. In certain embodiments, the peptides are used to evaluate the level of expression or activity of one or more members of the PEDF signaling pathway in a cell or sample.

In certain embodiments, the present invention comprises an assay comprising contacting a cell with one or more peptides disclosed herein. For example, the method may comprise administering the one or more peptides or administering one or more isolated nucleic acids encoding the one or more peptides. In certain embodiments, the method comprises contacting the cell with a culture medium, buffer, or the like comprising one or more peptides. In one embodiment, the method comprises genetically modifying a cell to express, and in certain instances secrete, one or more of the peptides disclosed herein by contacting the cell with one or more isolated nucleic acids encoding the one or more peptides. In one embodiment, the genetically modified cell is the cell being assayed. In one embodiment, the genetically modified cell is another cell (i.e., a second cell). For example, in one embodiment, the genetically modified cell may be a cell co-cultured with the cell being assayed.

The present invention also includes assays for inflammation, cell death or vascular leakage, comprising incubating cells with a peptide of the present invention and determining the effect of said peptide on said cells. Such assays are useful to determine which peptide is the optimal choice for use in treating a given disease state. Examples of such assays are presented below in the Examples section.

In one aspect, the present invention is directed to a screening assay to identify compounds that promote or inhibit PEDF signaling activity. For example, the screening assay can be used to identify compounds that increase or decrease the expression or activity of one or more members of the PEDF signaling pathway, thereby altering PEDF signaling. For example, the screening assay may be used to identify compounds that influence tumor growth, apoptosis, cytoskeletal function, function of mitochondrial and other organelles, oxidative stress, inflammation, angiogenesis, neurogenesis, cell growth, immune function, cell differentiation, adipogenesis, or bone deposition.

In one embodiment, the method comprises contacting a cell or biological sample with a peptide of the invention in the presence or absence of a test agent. The test agents can be obtained using any of the numerous approaches in combinatorial-library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223, 409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical that new chemical entities with useful properties are generated by identifying a chemical compound (called a "lead compound") with some desirable property or activity, creating variants of the lead compound, and evaluating the property and activity of those variant compounds. The current trend is to shorten the time scale for all aspects of drug discovery.

In one embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Antibodies

In one embodiment, the peptides of the present invention may be used for the generation of an antibody. For example, one or more peptides of the invention may be used to generate an antibody that specifically binds to the peptide and therefore also to a region of PEDF.

Methods of making and using antibodies are well known in the art. For example, polyclonal antibodies are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. In the present invention, the peptides of the invention may serve as the antigen. The chimeric proteins are produced by cloning the appropriate nucleic acids encoding the marker protein into a plasmid vector suitable for this purpose, such as but not limited to, pMAL-2 or pCMX.

The present invention should be construed to encompass antibodies which bind to the specific antigens of interest (i.e. peptide analogs of PEDF), and are able to bind the antigen present on Western blots, in solution in enzyme linked immunoassays, in fluorescence activated cells sorting (FACS) assays, in magenetic-actived cell sorting (MACS) assays, immunocytochemistry, immunoprecipitation, and in immunofluorescence microscopy of a cell transiently transfected with a nucleic acid encoding at least a portion of the antigenic protein, for example.

The antibodies of the invention may be used to neutralize the activity or to inhibit the activity of PEDF. For example, an antibody generated with the use of the peptides of the invention may be used as a therapeutic composition in order to inhibit the activity of PEDF, in conditions where excessive PEDF expression or activity is deleterious or associated with a particular disease or disorder.

The antibodies can be produced by immunizing an animal such as, but not limited to, a rabbit, a mouse or a camel, with an antigenic peptide of the invention, or a portion thereof, by immunizing an animal using a protein comprising at least a portion of the peptide, or a fusion protein including a tag polypeptide portion comprising, for example, a maltose binding protein tag polypeptide portion, covalently linked with a portion comprising the appropriate amino acid residues. One skilled in the art would appreciate, based upon the disclosure provided herein, that smaller fragments of these peptide can also be used to produce antibodies that specifically bind the antigen of interest.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

Further, the skilled artisan, based upon the disclosure provided herein, would appreciate that using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of an antigen of interest can be used to produce antibodies that are specific only for that antigenic peptide and do not cross-react non-specifically with other proteins or peptides, including other types of PEDF peptide fragments.

The invention encompasses monoclonal, synthetic antibodies, and the like. One skilled in the art would understand, based upon the disclosure provided herein, that the crucial feature of the antibody of the invention is that the antibody bind specifically with an antigen of interest. That is, the antibody of the invention recognizes an antigen of interest or a fragment thereof (e.g., an immunogenic portion or antigenic determinant thereof), on Western blots, in immunostaining of cells, and immunoprecipitates the antigen using standard methods well-known in the art.

One skilled in the art would appreciate, based upon the disclosure provided herein, that the antibodies can be used to immunoprecipitate and/or immuno-affinity purify their cognate antigen as described in detail elsewhere herein, and additionally, by using methods well-known in the art.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

In one embodiment of the invention, a phage antibody library may be generated, as described in detail elsewhere herein. To generate a phage antibody library, a cDNA library is first obtained from mRNA which is isolated from cells, e.g., peripheral blood lymphocytes, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding to its corresponding binding peptide, e.g., the antigen against which the antibody is directed, such as an antigen of interest (i.e. the PEDF peptide fragments of the invention). Thus, when bacteriophage which express a specific antibody are incubated in the presence of the corresponding antigen, the bacteriophage will bind to the antigen. Bacteriophage which do not express the antibody will not bind to the antigen. Such panning techniques are well known in the art and are described for example, in Wright et al. (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105). In another embodiment of the invention, phage-cloned antibodies derived from immunized animals can be humanized by known techniques.

Stem Cells

The peptides of the present invention are useful as a niche factor for maintaining stem cell populations. In certain embodiments, the present invention comprises a method of maintaining a stem cell comprising contacting the stem cell with one or more peptides disclosed herein. For example, the method may comprise administering the one or more peptides or administering one or more isolated nucleic acids encoding the one or more peptides. In certain embodiments, the method comprises contacting the stem cell with a culture medium, buffer, or the like comprising one or more peptides. In one embodiment, the method comprises genetically modifying a cell to express, and in certain instances secrete, one or more of the peptides disclosed herein by contacting the cell with one or more isolated nucleic acids encoding the one or more peptides. In certain embodiments, the genetically modified cell may be the stem cell or another cell. For example, in one embodiment, the genetically modified cell may be a cell co-cultured with the stem cell.

The method may be used to maintain one or more of any type of stem cell, including, but not limited to, pluripotent stem cell, multipotent stem cells, embryonic stem cells, somatic stem cells, cord blood-derived stem cells, induced pluripotent stem cells, hematopoietic stem cells, mesenchymal stem cells, neural stem cells, and the like.

In certain embodiments, the method comprises culturing a stem cell in a suitable culture medium, wherein the culture medium is supplemented with one or more peptides of the present invention.

In one embodiment, the stem cell is genetically modified to express, and in certain instances secrete, one or more of the peptides described herein.

In certain embodiments, the presence of one or more peptides of the present invention in a stem cell niche or in a culture medium promotes the self-renewal, differentiation, de-differentiation, proliferation, and/or expansion of a stem cell or stem cell population.

Therapeutic Methods

The peptides disclosed herein are useful in any therapeutic or prophylactic treatment known in the art, or subsequently discovered, for PEDF protein. Such therapeutic applications are disclosed in detail in, for instance, U.S. Pat. Nos. 6,451,763; 6,288,024; 6,391,850; 6,670,333; 6,797,691; 6,919,309 and US Patent Publication 20060008900, each of which is enclosed herein in its entirety. Methods of treatment may be therapeutic or prophylactic.

In one embodiment, the peptides of the invention are useful in treating a variety of pathologies including but not limited to inflammation, cell death, vascular leakage/neovascularization, and the like.

The peptides of the invention may be administered to a treatment site using any method known in the art. Exemplary pharmaceutical compositions and routes of administration are detailed elsewhere herein. In certain embodiments, the administration of one or more peptides of the invention comprises administering one or more peptides along with a drug delivery vehicle. The drug delivery vehicle may be a microparticle, nanoparticle, liposome, micelle, or other vehicle known in the art. The drug delivery vehicle may be administered locally into one or more regions of the eye or systemically.

In certain embodiments, administration of one or more peptides comprises administration of a cell comprising the one or more peptides or a nucleic acid encoding the one or more peptides. For example, in one embodiment, the method comprises administering to a subject a stem cell comprising a nucleic acid encoding one or more stem cells of the invention.

In certain embodiments, the method comprises a gene therapy method e.g., administration of an isolated nucleic acid encoding a peptide of the present invention. Engineering of such isolated nucleic acids by recombinant DNA or RNA methods is well within the ability of one skilled in the art. Codon optimization, for purposes of maximizing recombinant protein yields in particular cell backgrounds, is also well within the ability of one skilled in the art. Administration of an isolated nucleic acid encoding the peptide is encompassed by the expression "administering a therapeutically effective amount of a peptide of the invention". Gene therapy methods are well known in the art. See, e.g., WO96/07321 which discloses the use of gene therapy methods to generate intracellular antibodies. Gene therapy methods have also been successfully demonstrated in human patients. See, e.g., Baumgartner et al., Circulation 97: 12, 1114-1123 (1998), and more recently, Fatham, C. G. '*A gene therapy approach to treatment of autoimmune diseases*', Immun. Res. 18:15-26 (2007); and U.S. Pat. No. 7,378,089, both incorporated herein by reference. See also Bainbridge J W B et al. "*Effect of gene therapy on visual function in Leber's congenital Amaurosis*". N Engl J Med 358:2231-2239, 2008; and Maguire A M et al. "*Safety and efficacy of gene transfer for Leber's Congenital Amaurosis*". N Engl J Med 358:2240-8, 2008.

There are two major approaches for introducing a nucleic acid encoding the peptide (optionally contained in a vector) into a patients cells; in vivo and ex vivo. For in vivo delivery the nucleic acid is injected directly into the patient, usually at the site where the peptide is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Preferred in vivo nucleic acid transfer techniques include transfection with viral vectors such as adenovirus, Herpes simplex I virus, adeno-associated virus), lipid-based systems (useful lipids for lipid-mediated transfer of the gene are DOTMA, DOPE and DC-Chol, for example), naked DNA, and transposon-based expression systems. For review of the currently known gene marking and gene therapy protocols see Anderson et al., Science 256:808-813 (1992). See also WO 93/25673 and the references cited therein.

"Gene therapy" includes both conventional gene therapy where a lasting effect is achieved by a single treatment, and the administration of gene therapeutic agents, which involves the one time or repeated administration of a therapeutically effective DNA or mRNA. Oligonucleotides can be modified to enhance their uptake, e.g. by substituting their negatively charged phosphodiester groups by uncharged groups. Peptides of the present invention can be delivered using gene therapy methods, for example locally in a region of the eye, or systemically (e.g., via vectors that selectively target specific tissue types, for example, tissue-specific adeno-associated viral vectors). In some embodiments, primary cells (such as lymphocytes or stem cells) from the individual can be transfected ex vivo with a gene encoding any of the peptides of the present invention, and then returning the transfected cells to the individual's body.

Diabetic Retinopathy

Over 350 million individuals world-wide suffer from diabetes with hiking rates expected in the next 10 years due to the current obesity pandemic. As many as 10% of these individuals suffer from mild to severe loss of vision in a condition known as diabetic retinopathy which is caused by damage to neurons in the retina and hemorrhaging in the eye. Currently they are not effective treatments for diabetic retinopathy and there is an urgent need to develop biotherapeutics. Laser surgery is used in severe cases to reduce hemorrhaging but often results in more damage to visual neurons. Drugs currently under investigation for diabetic retinopathy are of the "anti-VEGF" class including Lucentis, Avastin, and the VEGF Trap, which are too large to deliver as eye drops and have limited efficacy. These are costly (>$1000/treatment), must be injected intraocularly-8-12 times/year, and only reduce vascular pathology. They do not prevent damage to visual neurons, which degenerate long before vascular leakage is detected in diabetic retinopathy. While controlling vascular leakage can prevent partial loss of vision, diabetic retinopathy begins in neurons that are degenerating much earlier in the retina.

The peptides of the present invention may be used in methods of treating diabetic retinopathy. In particular, a therapeutic amount of a peptide of the present invention is administered to a patient with diabetic retinopathy. Without being held to any particular theory, it is believed that the peptides of the present invention are able to help treat a variety of the pathological conditions relating to diabetic retinopathy including inflammation, cell death vascular leakage and macular edema. In certain embodiments, the peptides of the invention target three hallmark pathologies of diabetic retinopathy—inflammation, cell death, and vascular leakage. There is currently no known product that can target all three features of diabetic retinopathy. While any of the peptides of the present invention may be used to treat diabetic retinopathy and the related pathologies of diabetic retinopathy (including inflammation, cell death, vascular leakage and macular edema) in preferred embodiments the peptide is SpxA1, 81-2, 81-5, 81-12, 81-13 or 81-20 or combinations of these peptides. The peptide can be administered using any techniques known in the art and in a preferred embodiment the peptide is administered in the form of an eye drop.

Retinopathy of Prematurity

Retinopathy of prematurity (ROP) is a blinding disease seen in children. ROP has two phases. The first phase begins with delayed retinal vascular growth after birth and partial regression of existing vessels. The second phase is associated with hypoxia-induced pathological vessel growth. It is thought that excessive oxygen contributes to ROP through regulation of vascular endothelial growth factor (VEGF). Suppression of VEGF by oxygen in phase I of ROP inhibits normal vessel growth, whereas elevated levels of VEGF induced by hypoxia in phase II of ROP precipitate pathological vessel proliferation The peptides of the present invention may be used in methods of treating ROP in particular a therapeutic amount of a peptide of the present invention is administered to the patient with ROP. In certain embodiments, the peptides of the invention reduce the levels of VEGF in the retina, a key factor in the growth of endothelial cells and blood vessels. While any of the peptides of the present invention may be used, in preferred embodiments, the peptide is SpxA1, 81-2, 81-5, 81-12, 81-13 or 81-20 or combinations of these peptides. The peptide can be administered using any techniques known in the art and in a preferred embodiment the peptide is administered in the form of an eye drop.

Age-Related Macular Degeneration

Individuals over the age of forty are susceptible to Age-Related Macular Degeneration ("AMD"), a condition where neuronal cells of the retina die and in the wet form of the disease, neovasularization is prominent. AMD affects more than 9.1 million individuals in the USA (2010 data). Current Anti-VEGF drugs used to treat AMD are only initially effective in about 70% of all patients with the wet form of the disease, with decreasing efficacy over time, and there are no treatments for the dry form of AMD.

The peptides of the present invention may be used in methods of treating AMD in particular a therapeutic amount of a peptide of the present invention is administered to the patient with AMD. In certain embodiments, as in diabetic retinopathy, the peptides of the invention reduce vascular leakage, inflammation, and cell death—which, like diabetic retinopathy, are predominant features in. While any of the peptides of the present invention may be used, in preferred embodiments, the peptide is SpxA1, 81-2, 81-5, 81-10, 81-12, 81-13, 81-19 or 81-20 or combinations of these peptides. The peptide can be administered using any techniques known in the art and in a preferred embodiment the peptide is administered in the form of an eye drop.

Retinitis Pigmentosa

Retinitis pigmentosa is a group of inherited disorders in which abnormalities of the photoreceptors (rods or cones) or the retinal pigment epithelium of the retina lead to progressive visual loss. Some forms of retinitis pigmentosa are dominant, requiring only one gene from either parent; others are X-linked, requiring only one gene from the mother. In some people, mostly males, an inherited form of hearing loss also develops.

The retinal pigment epithelium provides nutrients and support to the photoreceptor cells of the retina, in particular, inhibitors of oxidative stress and apoptosis. For example, neurotrophins of the retinal pigment epithelium activate the release of anti-inflammatory and anti-oxidative factors.

In retinitis pigmentosa, there is chronic death of photoreceptor cells (rods and cones) of the retina. These photoreceptor cells, which are responsible for vision when light is low, gradually degenerate, so that vision becomes poor in the dark. The first symptoms of retinitis pigmentosa often begin in early childhood. Over time, a progressive loss of peripheral vision occurs. In the late stages of the disease, a person has a small area of central vision and a little peripheral vision remaining (tunnel vision). A need exists in the art for methods of treating retinitis pigmentosa.

The peptides of the present invention may be used in methods of treat retinitis pigmentosa. In particular a therapeutic amount of a peptide of the present invention is administered to the patient with retinitis pigmentosa. In certain embodiments, the neuroprotective action of the peptides of the invention reduces neuronal cell death and thus delays or prevents vision loss in the disease. While any of the peptides of the present invention may be used, in preferred embodiments, the peptide is SpxA1, 81-2, 81-5, 81-12, 81-13 or 81-20 or combinations of these peptides. The peptide can be administered using any techniques known in the art and in a preferred embodiment the peptide is administered in the form of an eye drop.

Glaucoma

Glaucoma is one of the three leading causes of blindness in the United States and it is a leading cause of blindness in the world. Over 2.2 million people in the United States have glaucoma, and several million more are at risk of developing the disease. As the population ages, the number of individuals with glaucoma will continue to grow since glaucoma affects the oldest individuals disproportionately. Glaucoma is not just one disease, rather, it is a spectrum of conditions that share a final common pathway of acquired, progressive deterioration of the neuronal components of the optic nerve. Neuronal death results in loss of vision once a sufficient number of individual nerves are destroyed.

Factors associated with the development of glaucoma and its progression have been identified and are in the process of being clarified. Elevated intraocular pressure (IOP) is the leading cause of glaucoma. Pressure is elevated because drainage of aqueous fluid from within the eye is impaired. Current treatments for glaucoma center on reducing pressure in the eye by reducing the amount of aqueous fluid being produced or by enhancing the flow of fluid out of the eye by mechanical or other means. Currently available drugs do not enhance or restore functioning of the natural drainage pathway.

Glaucoma patients may also suffer reduced blood flow to the optic nerve and neuronal tissue, diminished resistance of the nerve tissue to damage, and compliance of connective tissue surrounding and supporting the optic nerve. Current treatments do not address any such factors.

The peptides of the present invention may be used in methods of treat glaucoma in particular a therapeutic amount of a peptide of the present invention is administered to the patient with glaucoma. Much of the cell death seen in glaucoma is believed to be the result of oxidative stress. In certain embodiments, the peptides of the invention protects against oxidative stress and are thus reduces the ganglion cell loss. While any of the peptides of the present invention may be used, in preferred embodiments the peptide is SpxA1, 81-2, 81-5, 81-12, 81-13 or 81-20 or combinations of these peptides. The peptide can be administered using any techniques known in the art and in a preferred embodiment the peptide is administered in the form of an eye drop.

Uveitis

Uveitis refers to inflammation of the uvea, which is the middle, pigmented vascular structures of the eye, including the iris ciliary body and choroid. While uveitis is usually an isolated disorder, it is sometimes associated with one or more systemic or ophthalmic conditions. In some instances uveitis has infectious causes, where the presence of an infection results in an immune response which causes the inflammation of the uvea. In other instances, uveitis is caused by an autoimmune response, sometimes associated with systemic autoimmune disorders. Thus, increased levels of inflammatory markers are often observed both in the eye as well as in the serum of affected subjects.

Any of the peptides of the present invention may be used to treat uveitis. The peptide can be administered using any techniques known in the art and in a preferred embodiment the peptide is administered in the form of an eye drop.

Corneal Inflammation and Angiogenesis

Inflammation of the cornea may have numerous causes, including autoimmune mediated inflammation, infectious keratitis, or a heightened immune response to non-pathologic disturbances. Infectious keratitis may be caused by bacterial, fungal, viral, or parasitic invasion. If not treated adequately, corneal inflammation may lead to fibrinization secondary to inflammatory cells, granulomatous formation, deposition of fibroblasts, tissue hardening and destruction, neovascularization and pannus.

Any of the peptides of the present invention may be used to treat uveitis. The peptide can be administered using any techniques known in the art and in a preferred embodiment the peptide is administered in the form of an eye drop.

Other Diseases

The peptides of the invention can be used to treat a variety of diseases and disorders. In one embodiment, the peptides of the invention are useful in treating a variety of pathologies including but not limited to inflammation, cell death, vascular leakage/neovascularization, and the like.

Diabetes is associated with a high incidence of complications including retinopathy, nephropathy and peripheral neuropathy. It is also a major risk factor for cardiovascular diseases including stroke, and coronary artery disease. Diabetes is known to be associated with a state of general chronic, low-level inflammation, which precedes, and is believed to promote, insulin resistance and increase risk for cardiovascular disease. Obesity and other metabolic syndrome disorders that frequently lead to diabetes, including arterial hypertension, insulin resistance, dyslipidemia, and abdominal obesity, are also linked to chronic inflammatory response caused by elevated levels of proinflammatory cytokines such as TNF$\alpha$. As well as inflammation these diseases are associated with abnormal regulation of VEGF, neovascularization and vascular leakage. For example, in diabetic nephropathy there are increased levels of VEGF and angiogenesis as well as increased inflammatory cytokines including TNF$\alpha$.

The compositions of the invention reduce levels of the proangiogenic and vascular leakage factor VEGF, and the inflammatory molecules, TNF$\alpha$, and IFN$\gamma$. Such actions make these peptides important agents in the management of a wide range of diabetic complications and metabolic diseases where chronic inflammation and dysregulation of VEGF are considered key factors in the disease onset and progression.

The peptides disclosed herein may be used to treat or prevent diseases or disorders involving neuronal degeneration, including, but not limited to, nerve injuries, neurodegenerative diseases, and ocular diseases and disorders, including, but not limited to, transient or chronic ischemic injury. In particular, nerve injuries and neurodegenerative diseases of neurons in the retina, brain and spinal cord are beneficially treated using a peptide of the invention. Non-limiting examples of such diseases and disorders include Parkinson's disease, Huntington's disease, Alzheimer's disease, amyotrophic lateral sclerosis, multiple sclerosis, diabetic retinopathy, retinopathy of prematurity, macular degeneration, glaucoma, venous stasis retinopathy, ischemic oculopathy and ocular ischemic syndrome.

Neural transplantation can be used to treat nerve injuries and neurodegenerative diseases. Treatment of neuronal cells with compositions of the invention to enhance nerve cell survival is also embraced by the invention. Treatment may occur before, during or after neural transplantation. Similarly, transfection of either neurons or astroglia with an expression vector comprising a coding sequence for a peptide of the invention before implantation can provide a long-term source of a peptide at the transplantation site. Transplantation of neural retina and photoreceptor cells is contemplated to benefit from the treatment with a composition of the invention of the invention before, during or after transplantation. Alternatively, an expression vector comprising a coding sequence for a peptide of the invention can be transfected at high levels into adjacent retinal pigment epithelial (RPE) cells where they can serve as a source of the peptide.

In one embodiment, the peptides of the invention are useful in treating a condition including but is not limited sepsis, acute respiratory distress syndrome, nephrotic syndrome, diabetic neuropathy, preproliferative diabetic retinopathy, cancer, or proliferative diabetic retinopathy.

In one embodiment, the peptides of the invention can inhibit the growth of blood vessels within and to the tumor, and in some cases, induce tumor cells to differentiate and thus divide slowly. Inhibiting the growth of blood vessels within tumors prevents sufficient nutrients and oxygen from being supplied to the tumor to support growth beyond a given size. Thus, the inventive method can prevent the nucleation of tumors from cancerous cells already present due to genetic predisposition or the presence of external carcinogens (e.g., tobacco, alcohol, industrial solvents, etc.). Aside from preventing tumorigenesis, the inventive method can retard the growth of existing tumors, thus rendering them more easily contained and excised and may cause them to regress. This application is highly advantageous for treating tumors that are difficult to operate on (e.g., brain or prostate tumors). In addition, the method is useful for treatment of childhood tumors, including, but not limited to, neuroblastoma. Moreover, minimizing the number of blood vessels within existing tumors lessens the probability that the tumor will metastasize. In treating tumors, the method can be used alone or in conjunction with other treatments, to control the growth of tumors. Indeed, employing the inventive method can potentiate the response of some tumors to other therapies. For example, the inventive method optionally can be employed as a pretreatment for (e.g., for about a week in advance of), and continued during, a chemotherapeutic or radiation regimen. The method of the invention may also be used in conjunction with the use of biological response modifiers, such as for example, interferon, or other anti-angiogenic agents, and also is useful in conjunction with the use of agents which induce the production of anti-angiogenic agents in vivo. Further, the method of the invention may be used in conjunction with agents which promote the differentiation of cells, particularly, but not limited to agents which promote the differentiation of brain tumor cells.

In one embodiment, the peptides of the invention are useful for the prevention of neovascularization. Thus, for example, the inventive method can be used as part of a treatment for disorders of blood vessels (e.g., hemangiomas and capillary proliferation within atherosclerotic plaques), muscle (e.g., myocardial angiogenesis or angiogenesis within smooth muscles), joints (e.g., arthritis, hemophiliac joints, etc.), and other disorders associated with angiogenesis (e.g., Osler-Webber Syndrome, plaque neovascularization, telangiectasia, angiofibroma, wound granularization, etc.). In addition, the invention is useful for treatment of nasal polyps, especially in cystic fibrosis patients, leukemia which stems from bone marrow cell abnormal growth, and prostate cancer. The invention can be construed in general to be useful for treatment of benign neoplasias.

The inventive method is also useful as a means of preventing the occurrence of a disease or disorder associated with vascular permeability or angiogenesis, i.e., the methods are useful as prophylactic methods for the prevention of disease in patients at risk for the disease. For example, and without limitation, the peptides of the invention can be used to prevent the onset of diabetic retinopathy in a patient having diabetes, to prevent the onset of cancer in persons known to be at risk for certain cancers, and the like. Thus, the methods of the invention should not be construed as being limited to treatment of overt disease, but rather, should be construed as being useful for the prevention of disease in patients who are at risk.

The invention should also be construed to include treatment of precancerous lesions, for example, but without limitation, nasal polyps, particularly in patients having cystic fibrosis. Nasal polyps in these patients are angiogenic, and further, the cerebral spinal fluid of cystic fibrosis patients contains an excess of the angiogenic factor VEGF. Alleviation of these conditions, especially in cystic fibrosis patients, wherein the alleviation comprises administration of the peptides of the invention is therefore included in the present invention.

Within the context of the inventive method, peptides of the invention can be supplied alone or in conjunction with other known antiangiogenic factors. For example, the peptides of the invention can be used in conjunction with antibodies and peptides that block integrin engagement, proteins and small molecules that inhibit metalloproteinases (e.g., marmistat), agents that block phosphorylation cascades within endothelial cells (e.g., herbamycin), dominant negative receptors for known inducers of angiogenesis, antibodies against inducers of angiogenesis or other compounds that block their activity (e.g., suramin), or other compounds (e.g., retinoids, IL-4, interferons, etc.) acting by other means. Indeed, as such factors modulate angiogenesis by different mechanisms, employing peptides of the invention in combination with other antiangiogenic agents can potentiate a more potent (and potentially synergistic) inhibition of angiogenesis within the desired tissue.

Pharmaceutical Compositions and Formulations

The invention also encompasses the use of pharmaceutical compositions of the invention or salts thereof to practice the methods of the invention. Such a pharmaceutical composition may consist of at least one compound or conjugate of the invention or a salt thereof in a form suitable for administration to a subject, or the pharmaceutical composition may comprise at least one compound or conjugate of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

The peptides of the invention may be administered by a variety of methods including administration as an eye drop, administration by intraocular injection, administration as a gel to the eye, administration as an implant in the eye that releases the peptide over time, administration as a virus that expresses the peptide, and administration using a cell-based expression system. Each of these methods are known in the art and are discussed in more detail below.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a “unit dose” is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington’s Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, ophthalmic, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount of a therapeutic composition of the invention. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

In certain embodiments, administration of the composition of the invention is non-invasive. For example, in certain embodiments administration comprises ophthalmic delivery, for example by way of an eye drop or other ophthalmic formulation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, and the type and age of the animal.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Peptide Metabolism, Bioavailability, and Bioactivity of the Small Peptides Derived from P78

Experiments were designed to identify metabolic sites within the P78 fragment. Experiments were designed to determine whether shorter analogs have better bioavailability and maintain the same bioactivity compared to P78 or PEDF. Experiments were also performed to assess the effect of site-specific mutations on peptide metabolism, bioavailability, and bioactivity of the small peptides derived from P78.

Briefly, analogs of P78 were designed and synthesized (Table 1). As a non-limiting example, the analogs can be synthesized by GenScript (GenScript USA Inc., Piscataway, N.J. 08854). Some of the analogs included peptide modifications including but not limited to altering the charge of the peptides, altering peptide stability, generating shorter fragments (e.g., 29 mer, 17 mer molecules), changing two residues in a 17-mer fragment to Isoleucine, changing two residues in a 17-mer fragment to Alanine, changing four residues in a 17-mer fragment (2 Ile; 2 Ala), addition of fatty acid modifications at the N-terminus and Pegylation at the C-terminus of a 29 mer and a 17-mer fragment).

TABLE 1

Peptide analogs of P78

| Peptide | SEQUENCE | Length #AA | Modified residues | Theoretical MW |
|---|---|---|---|---|
| P-78 | VLLSPLSVATALSALSLGADERTESIIHRALYYD LISSPDIHGT (SEQ ID NO: 42) | 44 | N | 4667.30 |
| SpxA1 | VLLSPLSVATALSALSLGADERTESIIHR (SEQ ID NO: 44) | 29 | N | 3020.48 |
| 81-1 | SALSLGADERTESIIHR (SEQ ID NO: 1) | 17 | N | 1855.04 |
| 81-2 | SAISIGADERTESIIHR (SEQ ID NO: 2) | 17 | L → I | 1855.04 |
| 81-3 | SAISIGADARTASIIHR (SEQ ID NO: 3) | 17 | (L→ I)$_2$; (E→ A)$_2$ | 1738.97 |
| 81-4 | {BA*}VLLSPLSVATALSAISIGADARTASIIHR {PEG*}(SEQ ID NO: 4) | 29 | (L→I)$_2$; (E →A)$_2$* | 3119.50 |
| 81-5 | {BA*}SAISIGADARTASIIHR{PEG*} (SEQ ID NO: 5) | 17 | (L→ I)$_2$; (E→ A)$_2^{\#}$ | 1954.24 |
| 81-6 | ALYYDLISSPDIHGT (COOH) (SEQ ID NO: 6) | 15 | N | 1664.82 |
| 81-7 | VLLSPLSVATAL (NH2) (SEQ ID NO: 7) | 12 | N | 1183.44 |
| 81-8 | SALSLGADERTES (SEQ ID NO: 8) | 13 | N | 1335.38 |
| 81-9 | SAISIGADARTAS (SEQ ID NO: 9) | 13 | (L →I)$_2$; (E→ A)$_2$ | 1219.31 |
| 81-10 | VLLSPLSVATALSAISIGADARTASIIHR (SEQ ID NO: 10) | 29 | (L→ I)$_2$; (E→ A)$_2$ | 2904.38 |
| 81-11 | {BA*}SAISIGADERTESIIHR{PEG*} (SEQ ID NO: 11) | 17 | (L→ I)$_2$* | |
| 81-12 | {BA*}NFGYDLYRVRSSMSPTTNSALSLGADER TESIIHR{PEG*} (SEQ ID NO: 12) | 35 | P60 + 81-1; BA (NH2); PEG-COOH | |
| 81-13 | SALSLGAAERTESIIHR (SEQ ID NO: 13) | 17 | D→ A | 1811.01 |
| 81-14 | SALSLGANERTESIIHR (SEQ ID NO: 14) | 17 | D→ N | 1854.04 |

TABLE 1-continued

| Peptide analogs of P78 | | | | |
|---|---|---|---|---|
| Peptide | SEQUENCE | Length #AA | Modified residues | Theoretical MW |
| 81-15 | SALSLGADE**A**TESIIHR (SEQ ID NO: 15) | 17 | R →A | 1769.92 |
| 81-16 | **S**ADERTESIIHR (SEQ ID NO: 16) | 12 | G →S | 1413.50 |
| 81-17 | SALSL**F**ADERTESIIHR (SEQ ID NO: 17) | 17 | G→ F | 1945.15 |
| 81-18 | SALSL (L-1-NAL)ADERTESIIHR (SEQ ID NO: 18) | 17 | G→ L-1-NAL | 1995.21 |
| 81-19 | **F**GADERTESIIHR (SEQ ID NO: 19) | 13 | L →F | 1530.65 |
| 81-20 | **L-1-NAL**GADERTESIIHR (SEQ ID NO: 20) | 13 | L→ L-1-NAL | |

*81-4: CH3-CH2-CH2-(CO-NH)-VLLSPLSVATALSAISIGADARTASIIHR-(CO-NH)-PEG2-CH2COOH
#81-5:CH3-CH2-CH2-(CO-NH)-SAISIGADARTASIIHR-(CO-NH)-PEG2-CH2COOH;
{BA*}: Butyric acid on N-terminus;
{PEG*} = Fmoc-NH-PEG2-CH2COOH The analogs were tested for their efficacy in reducing levels of TNFα, IFNγ, VEGF-A and increasing cell viability in in vitro assays. Efficacy was compared to both non-treated oxidative stressed controls and the control standard P78.

In addition, bioavailability studies of the peptides in rodent eyes were conducted and the results were compared to the control standard P78 peptide. For example, the peptides were tested in bioavailability studies in rodents at 1, 2, 4, 8 hrs (n=4 each peptide/time pt). The animals were given a single eye drop containing 2 μg of each peptide. At each time point the animals were sacrificed, vitreous harvested, and bioavailability assessed by Maldi TOF.

The results indicate that peptide 81-5 has the highest level of activity in all three in vitro tests—inflammation, angiogenesis, and cell viability with efficacy ranging between 15-41% greater than P78 and 18-65% improvement to the control stressed samples.

Two of the truncated (17 mer) peptides demonstrated biological activity that is better than that observed with P78. Peptide 81-2 shows good efficacy and bioavailability profiles of all the peptides tested. It is ~8-18% better than P78 and the control in the inflammatory and angiogenesis assays and 8-26% better than P78 and control in the viability assay. 81-5 is a strong candidate from the in vitro studies. The results of these experiments are summarized in Table 2.

Example 2

The Effects of the Peptides to Increase Cell Viability

The analogs disclosed in Table 1 were assayed for improved stability and efficacy in in vitro assays for inflammation, angiogenesis, and cell death, which are the three leading pathological features of diabetic retinopathy.

Briefly, to test efficacy of the compounds in preventing cell death, experiments were performed to screen for the ability of each analog to: 1) increase cellular bioenergetic levels in an ATP assay and 2) reduce cell death in an LDH assay. To test the action of each analog on inflammatory processes, Luminex bead arrays were used to examine the ability of each analog to decrease production of inflammatory cytokines. To test for the potential of each analog to reduce vascular leakage, qPCR was used to examine the ability of each analog to increase mRNA levels of ZO1 and occludin, two junction proteins essential to vascular integrity. To test peptide stability in the vitreous, the analogs were incubated with dissected vitreous humor and the samples were analyzed at various time points using Maldi-TOF. These tests allowed for the systematic selection of analogs having the least toxicity and the strongest potential to reduce pathology in vivo.

TABLE 2

| Summary of biological activity | | | | | | | | | | | |
|---|---|---|---|---|---|---|---|---|---|---|---|
| Analogs | residues | SEQ changes | *TNFα % to C | *TNFα % to P78 | *IFNγ % to C | *IFNγ % to P78 | *VEGF % to C | *VEGF % to P78 | *ATP % to C | *ATP % to P78 | ^ after 4 hr |
| P-78 | 44 | N | +2% | 0% | −5% | 0% | −5% | 0% | +17% | 0% | 1200 ng/ml |
| SpxA1 | 29 | N | −3% | −5% | −9% | −5% | −5% | 0% | +5% | −11% | 920 ng/ml |
| 81-1 | 12 | N | −3% | −5% | −4% | +1% | −8% | −3% | +9% | −11% | 1800 ng/ml |
| 81-2 | 17 | M(2) | −13% | −15% | −12% | −8% | −18% | −14% | +25% | −8% | 2000 ng/ml |
| 81-3 | 17 | M(4) | −7% | −8% | −9% | −4% | −12% | −7% | +11% | 5% | 2280 ng/ml |
| 81-4 | 29 | M(4) | −2% | −8% | −15% | −11% | −11% | −0% | +7% | 9% | |
| 81-5 | 27 | M(4) | −18% | −19% | −20% | −15% | −20% | −16% | +65% | −41% | |
| 81-6 | 25 | N | | | | | | | | | |
| 81-7 | 12 | N | | | | | | | | | |
| 81-8 | 13 | N | | | | | | | | | |
| 81-9 | 13 | M | | | | | | | | | |
| 81-10 | 29 | M | | | | | | | | | |

Twenty P78 peptide analogs were generated. The size of the analogs ranged from 35 to 12 amino acids in length (Table 1). These peptides had internal amino acid substitutions of the sequence and/or helix stabilization and hydrophobic cap changes to improve peptide stability and efficacy. The peptides were all tested and compared to P78 and spxA1 for efficacy in cell viability and release of TNFα, IFNγ, and VEGFA—three of the most potent inflammatory, vascular leakage, and angiogenesis markers in the retina. Several of the peptides showed activity differences ranging between ~5-20% when compared to P78. Several of the peptides were significantly less active than P78.

Figure 2A:
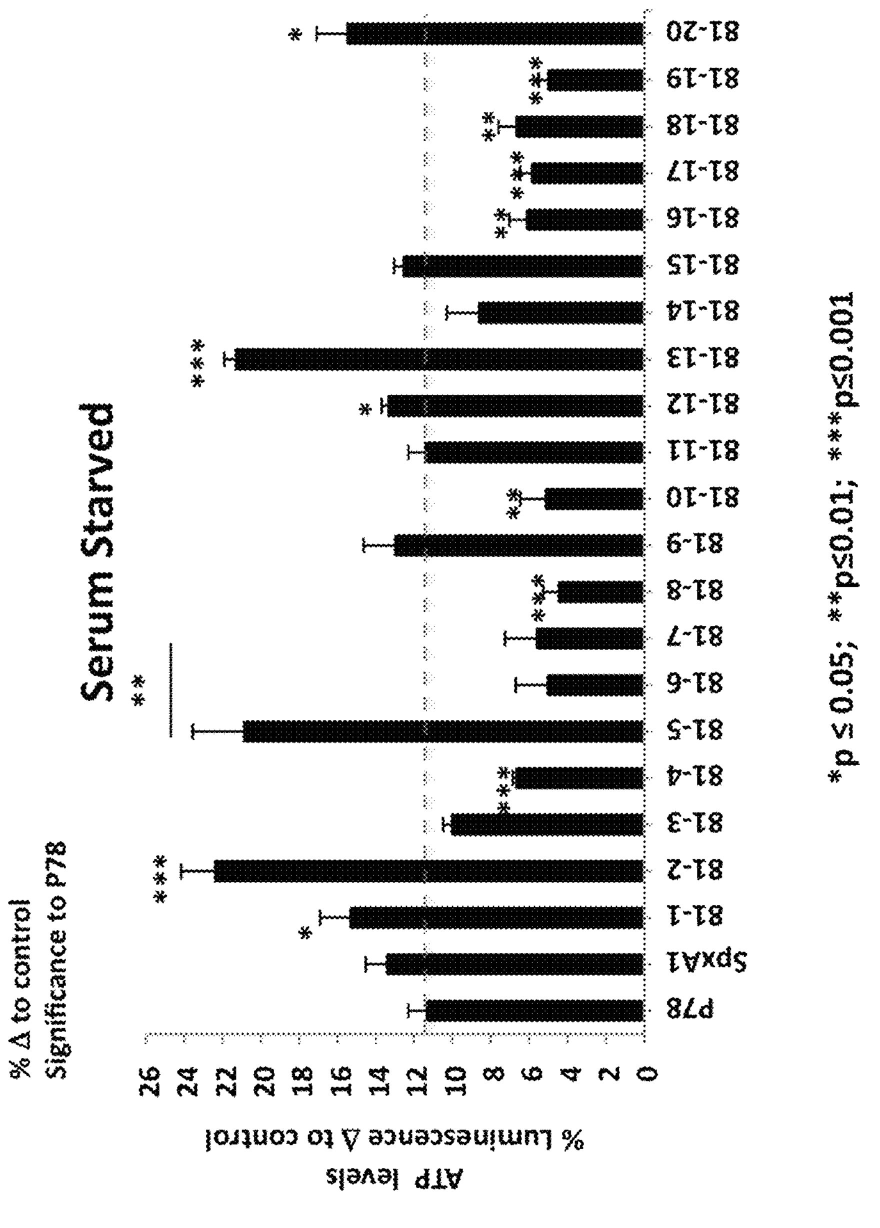
FIG. 2A and FIG. 2B, is a series of graphs demonstrating the effects of the peptides to increase cell viability by increasing levels of ATP were tested in two models of cell death.
Figure 2B:
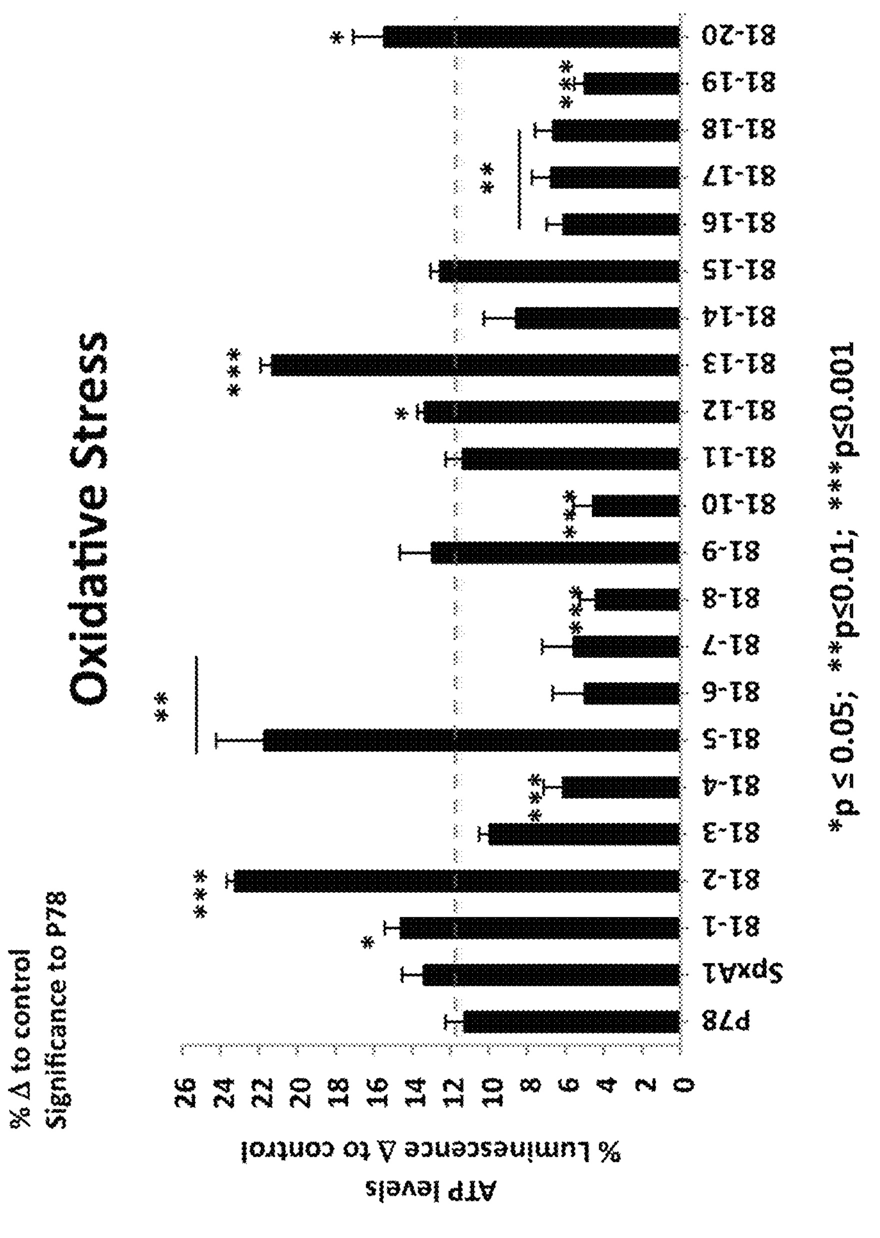

The effects of the peptides to increase cell viability by increasing levels of ATP were tested in two models of cell death: (i) serum starvation; (ii) oxidative stress caused by hydrogen peroxide toxicity (300 uM). With respect to serum starvation, human ARPE19 cells were grown to ~85% confluency in 10% serum containing medium after which the cells were placed in serum-free medium for 48 hr in the presence or absence (control) of 25 nM of each peptide. For ATP assay, CellTiter-Glo® reagents were used and luminescence was determined after 12 min spectrophotometrically (n=4) (FIG. 2A). With respect to oxidative stress, human ARPE19 cells were grown to ~85% confluency in 10% serum containing medium. The cells were then treated with 300 uM $H_2O_2$ for 48 hours in the presence or absence (control) of 25 nM of each peptide. Levels of ATP were measured and % luminescence to controls and P78 was quantitated (n=4). Changes to ATP levels are plotted against control values and p values are given to P78 (FIG. 2B). The results demonstrate that peptides 81-2, 81-5, 81-12, 81-13, 81-20 are considered good candidates for the in vivo studies.

Example 3

Figure 3A:
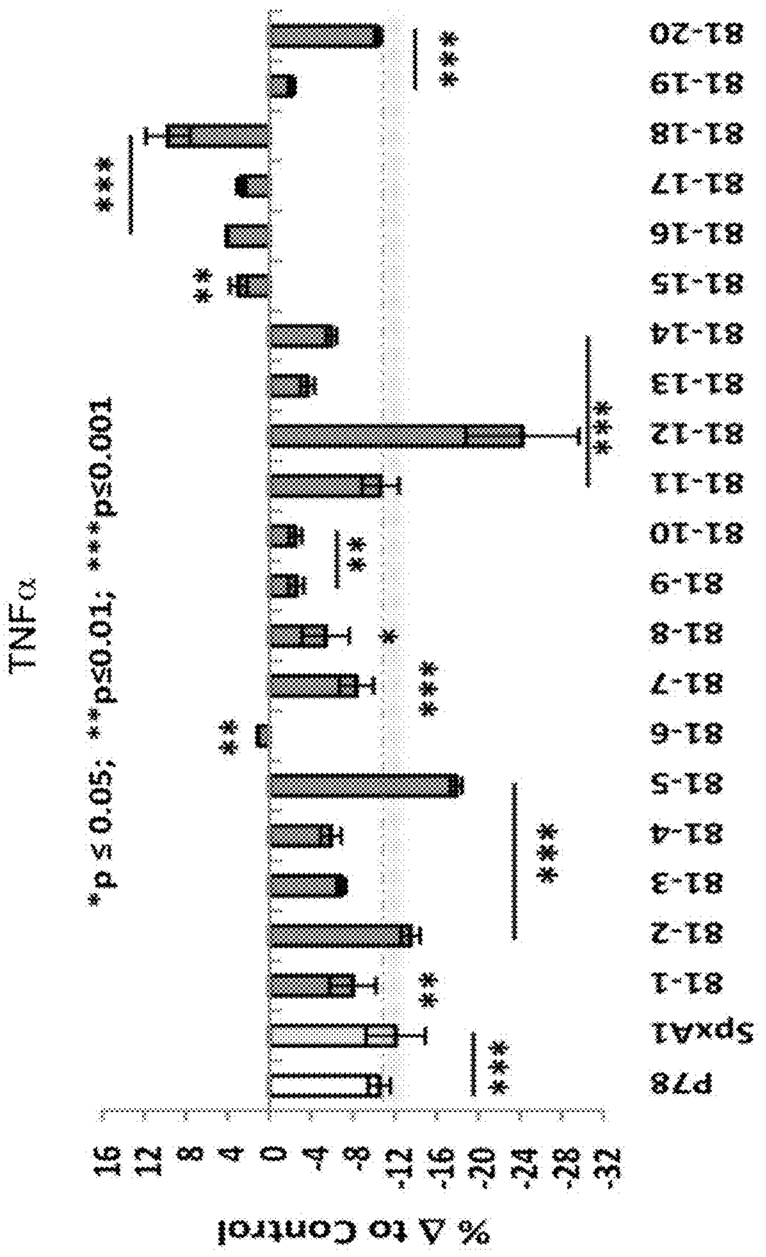
FIG. 3A through FIG. 3C, is a series of graphs depicting the results of in vitro experiments in RPE cultures. The graphs demonstrate the effects of each peptide on the inflammatory and vascular permeability/angiogenesis cytokines TNFα (FIG. 3A), IFNγ (FIG. 3B), and VEGFA (FIG. 3C) compared to P78.
Figure 3B:
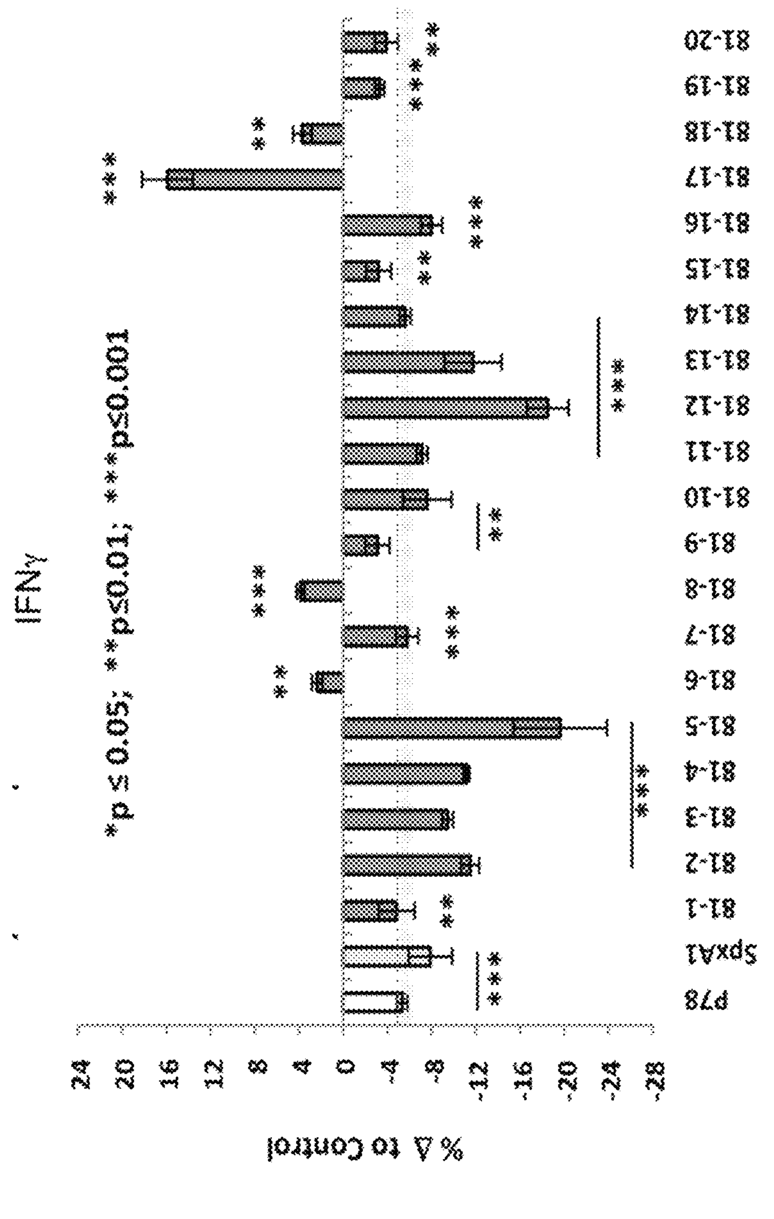
Figure 3C:
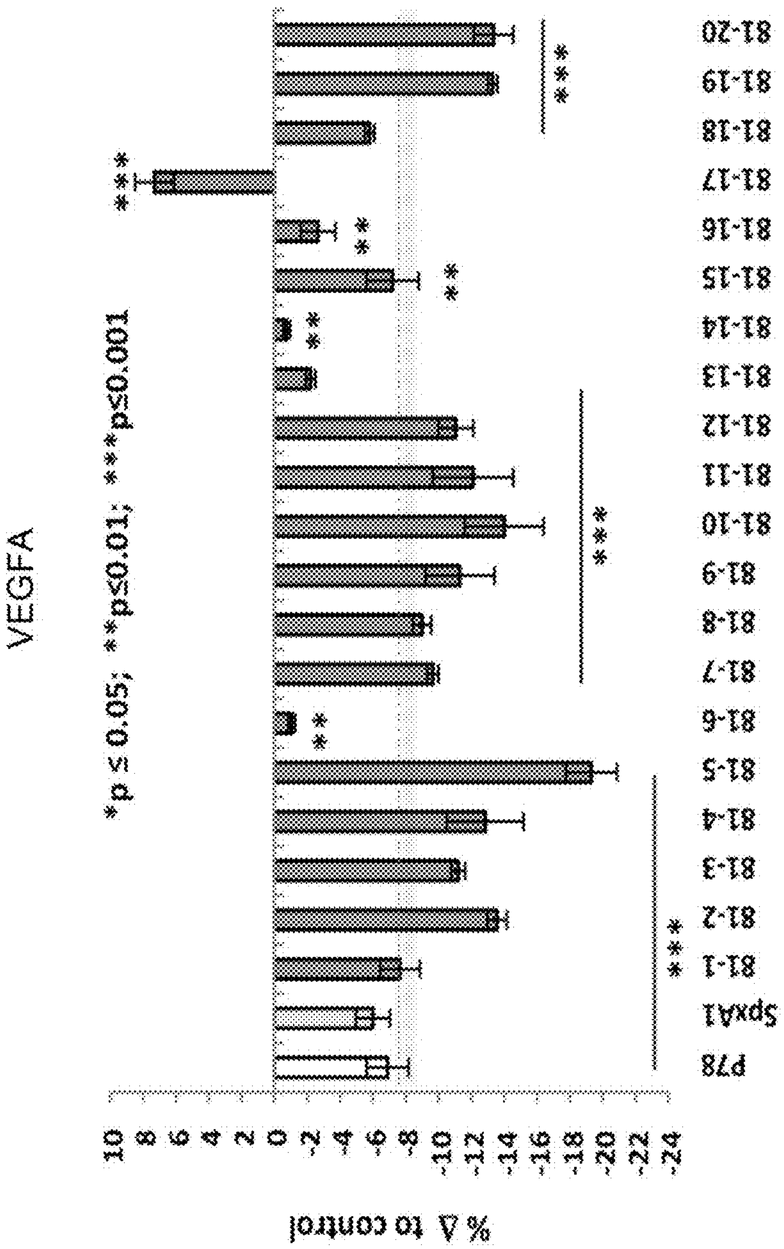

The Effects of the Peptides on the Inflammatory and Vascular Permeability/Angiogenesis Cytokines Experiments were designed to assess the effects of each peptide compared to P78 on the inflammatory and vascular permeability/angiogenesis cytokines TNFα, IFNγ, and VEGFA. Briefly, human retinal RPE cells were grown to ~75% confluency in 10% serum containing medium. The cells were then exposed to serum starvation in the presence or absence (control) of 25 nM of each peptide including the prototype P78 and the active fragment of P78, SpxA1. The supernatant from each treatment was tested for effects on the secretion of TNFα, IFNγ, and VEGFA. The data represent the percent change to the control samples and p values are given for each peptide in relationship to the P78 treatment (FIGS. 3A through 3B).

The results presented herein also demonstrate that peptides 81-10 and 81-19 have significantly better effects in reducing VEGFA levels but were less effective than P78 on the other assays. These peptides may be considered specific anti-VEGF drugs.

Example 4

Ability to Reduce Vascular Leakage

Figure 4A:
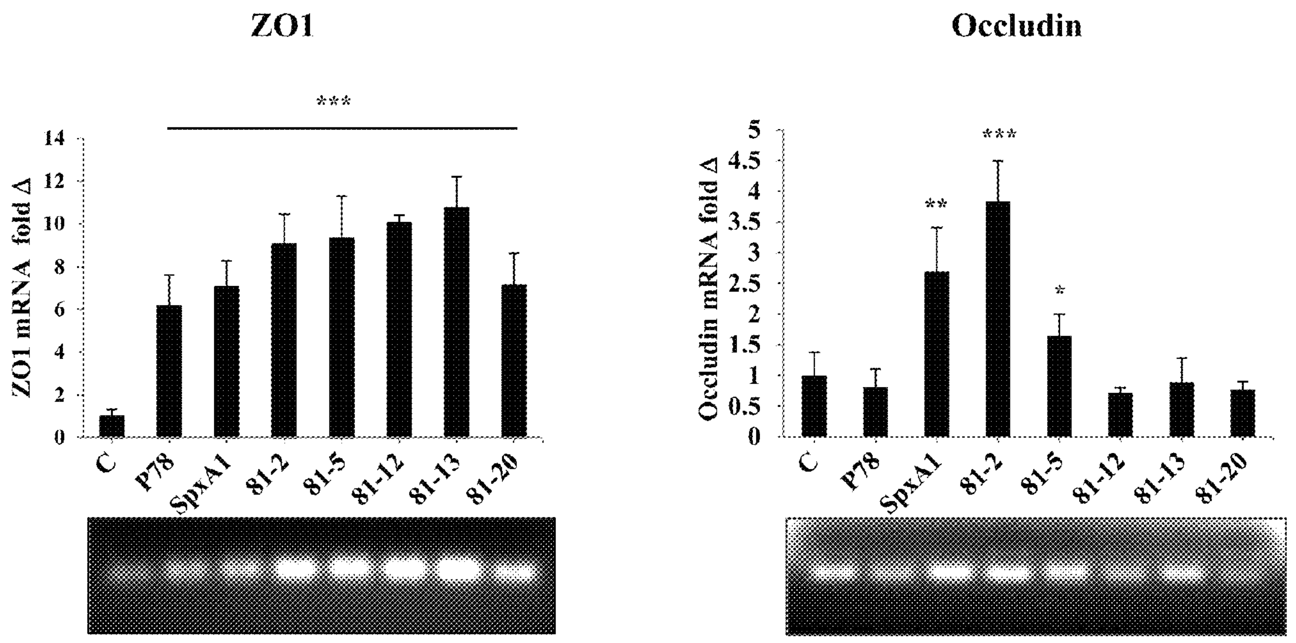
FIG. 4A and FIG. 4B, is a series of images depicting the ability of the peptides to reduce vascular leakage and stability of the peptides. The peptides resulted in increase in the tight junction proteins ZO1 and occludin (FIG. 4A). The results demonstrate that the peptides were more stable compared to P78 and SpxA1 (FIG. 4B).

To test for the potential of each peptide (81-2, 81-5, 81-12, 81-13 and 81-20) to reduce vascular leakage, qPCR was used to examine the ability of each analog to increase mRNA levels of Z01, a junction protein essential to vascular integrity (FIG. 4A). The results demonstrate that the peptides resulted in a higher expression of ZO1 compared to P78 and SpxA1.

Example 5

Peptide Stability

Figure 4B:
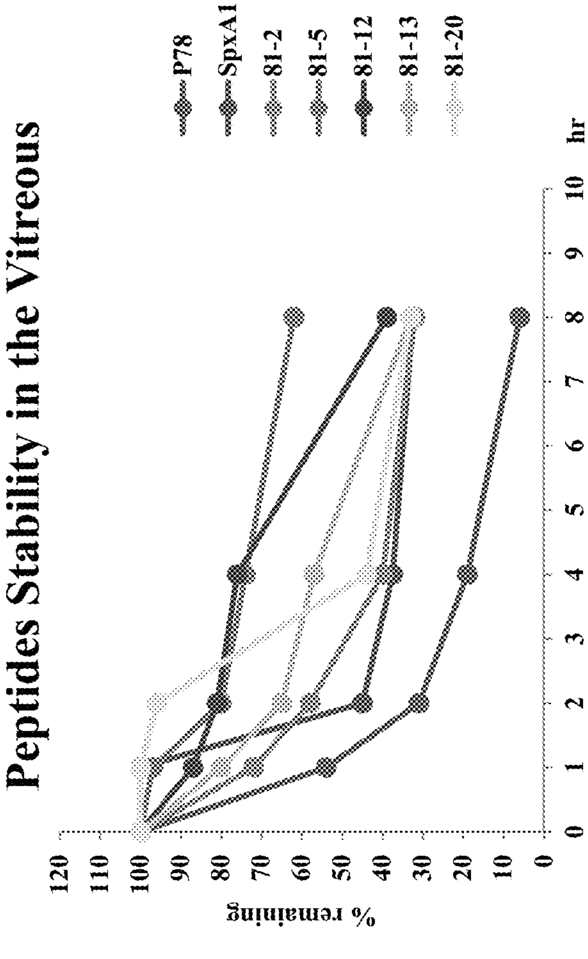
Figure 5A:
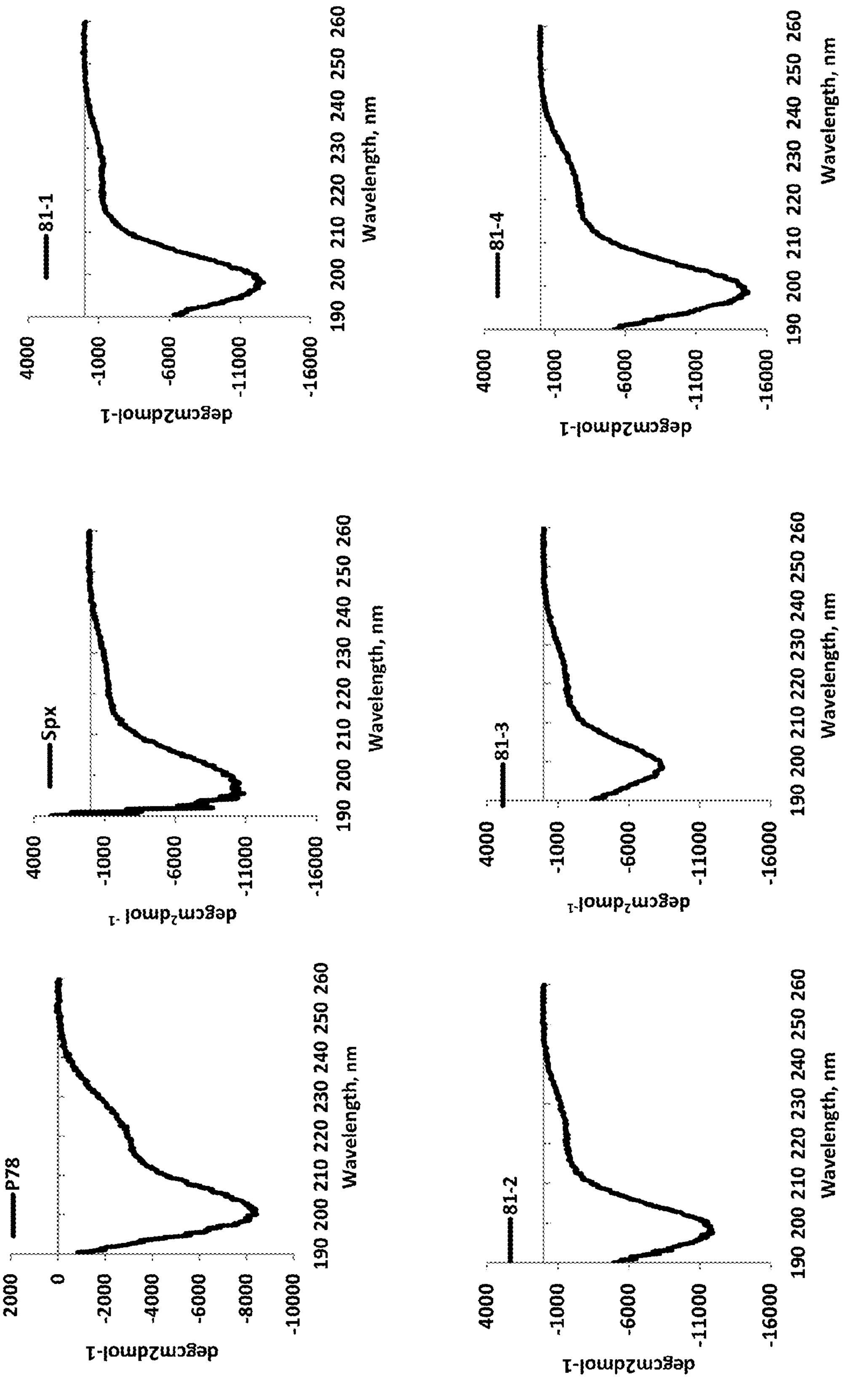
FIG. 5, comprising FIG. 5A through FIG. 5D is a series of graphs depicting the CD spectra for various peptides, demonstrating the helical structure of the peptides.
Figure 5B:
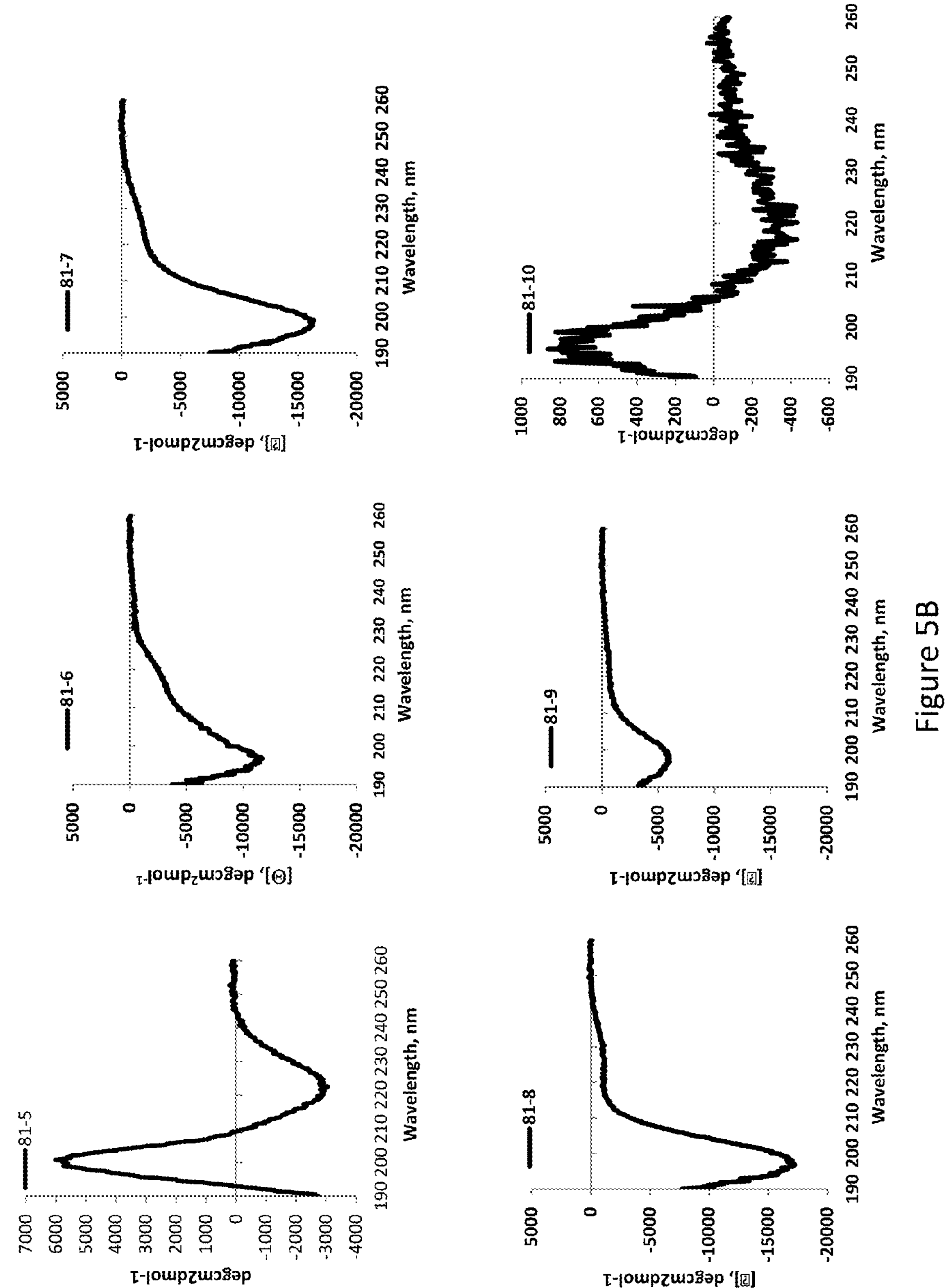
Figure 5C:
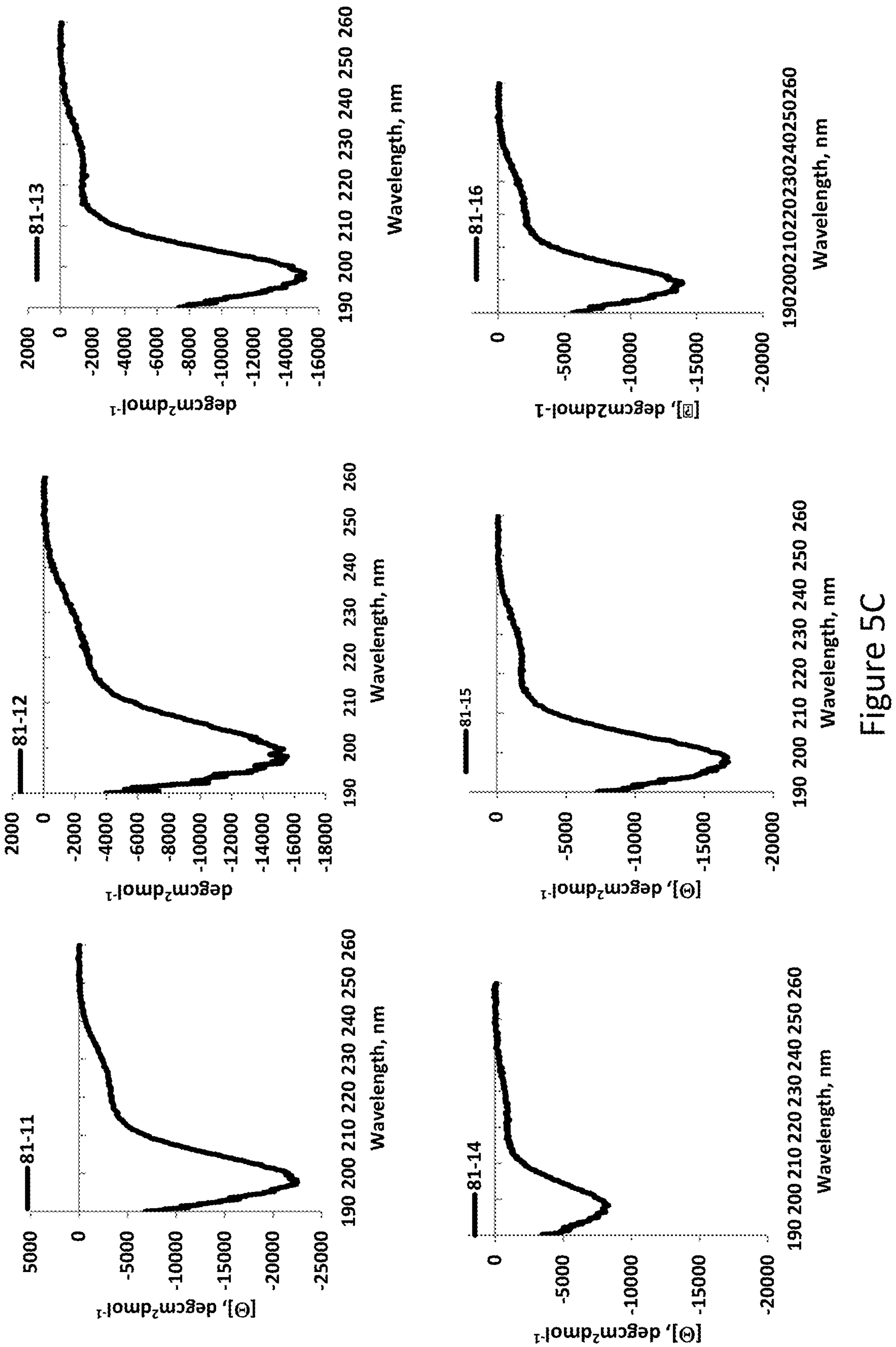
Figure 5D:
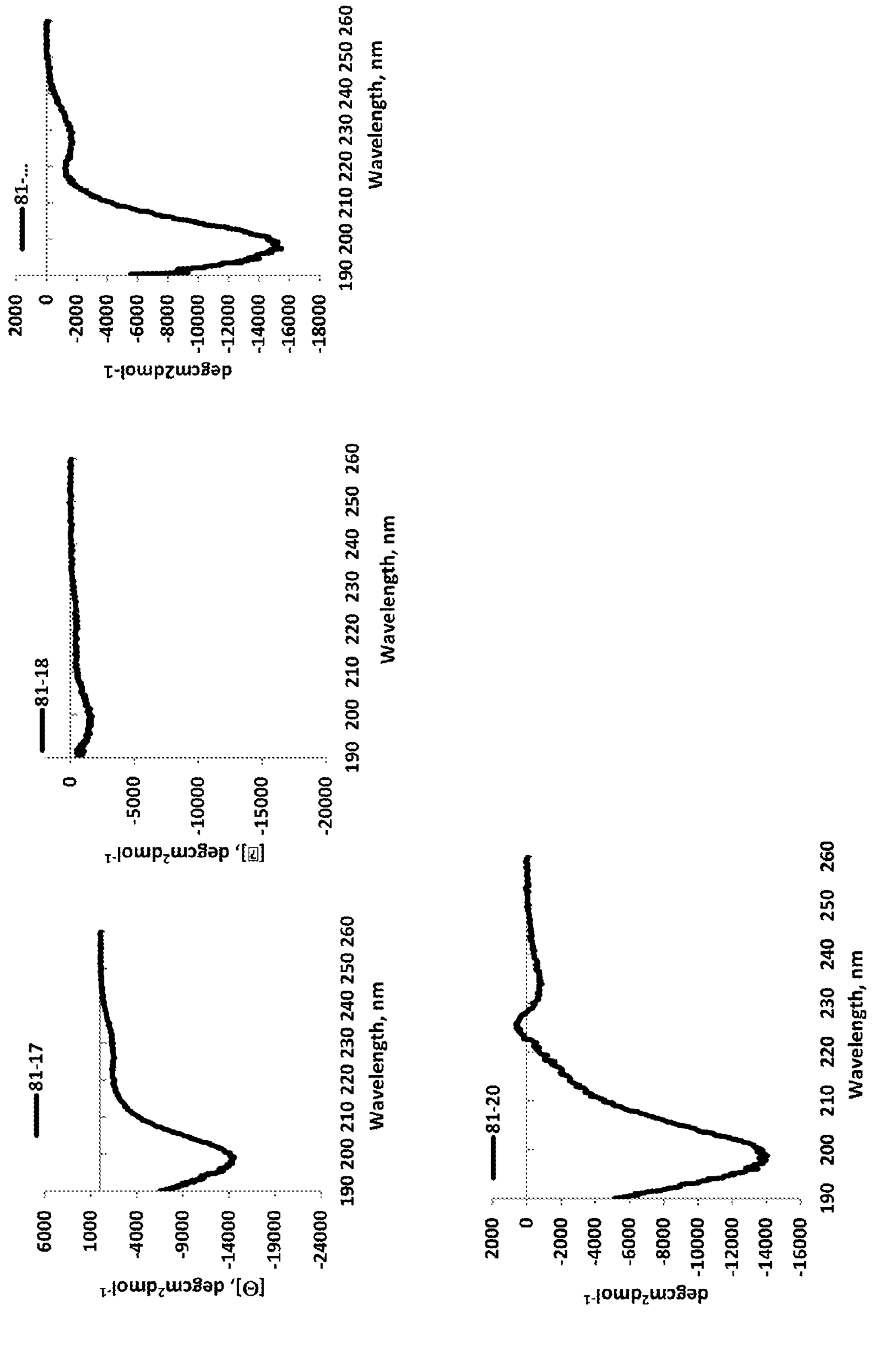

To test peptide stability in the vitreous, the analogs were incubated with dissected vitreous humor and the samples were analyzed at various time points using Maldi TOF (FIG. 4B). The results demonstrate that the peptides were more stable compared to P78 and SpxA1.

Example 6

Structure of Peptides

CD spectroscopy was used to evaluate the structure of the peptides (FIG. 5A-FIG. 5D). The CD spectra for the peptides demonstrate the helical structure of the peptides. It was observed that while all of the peptides have some helical structure, 81-5 is almost a perfect for alpha helix.

Example 7

In Vivo Testing

The peptides of the invention can be tested in vivo in any animal model. An exemplary animal model is the $Ins2^{Akita}$ mouse described by Liu et al. (2012, Mol Med 18: 1387-1401), which is hereby incorporated by reference in its entirety. This animal model has been used to assess the activity of PEDF in reducing diabetic retinopathy complications.

Eye Drop Formulation

Briefly, an eye drop formula containing 1 mg/mL labeled dialyzed peptide diluted in artificial tears (Prestige Brands International) is prepared for each sample. Eye drops are administered in 5 μL (5 μg) volume onto the ocular surface of rats or diabetic mice to test distribution of the labeled peptides in the eye and to quantify levels reaching the vitreous compartment.

Eye Drop Treatments: $Ins2^{Akita}$ Diabetic Mice

Hyperglycemic heterozygote C57BL/6J Ins2Akita mice (The Jackson Laboratory, Bar Harbor, Me., USA) have a mutation in the Ins2 gene that results in hyperglycemia at ~4.5 wks of age and detectable vascular complications at ~16-17 wks of age (12-13 wks of hyperglycemia). These animals are kept on a 12-h light-dark cycle, and food and water are provided ad libitum. Insulin is not supplemented to the diet. Heterozygote Ins2Akita males are crossed with C57/B16/J females and diabetic offspring are confirmed by genotyping and blood glucose levels >250 mg/dL at 4.5 wks of age. Only male hyperglycemic mice are used, since diabetic retinopathy in females displays inconsistent pathological features. Glucose levels are measured in blood samples obtained from tail punctures by using the One-Touch LifeScan meter (LifeScan, Milpitas, Calif., USA). Animals with 300-400 mg/dL serum glucose levels are used in this study.

One group of diabetic Ins2Akita mice are treated with eye drops containing labeled peptides for 2-4 h to examine distribution of the molecules in the eye. The animals are anesthetized at specific time points by using ketamine (100 mg/kg) and xylazine (10 mg/kg) intraperitoneally, and eyes are enucleated and washed extensively in ice-cold PBS.

Whole eyes or dissected retinas and corneas are fixed with 4% paraformaldehyde, embedded in O.C.T. (Tissue-Tek; Sakura, Alphen aan den Rijn, the Netherlands) and are cryosectioned.

A second group of mice is used to determine effects of the peptides on diabetes-induced pathologies in the retina over a period of 15 wks of hyperglycemia. This time point was chosen because vascular pathology is easier to detect by the present methods (beginning at ~12.5 wks). Diabetic male Ins2Akita mice will receive one peptide eye drop per week for 13-15 wks immediately at the onset of hyperglycemia (4.5 wks old). Mice are manually restrained or lightly anesthetized when necessary, and 5-μL unlabeled peptides in ATs are applied to the corneal surface. This group is subdivided into four treatment groups, each receiving one of the following eye drops: P60, P78, P78+P60 or ATs. Both eyes will receive the same treatment to avoid drug cross-contamination between the eyes by the animal. Animals are given 200 μL saline intraperitoneally to prevent dehydration and are placed in warmed cages to recover.

Presented herein are experiments to evaluate the effects of the peptides of the invention on cell death, vascular leakage, and inflammation. These assays may be used to evaluate the peptides in treating diabetic retinopathy, glaucoma, retinitis pigmentosa, AMD, and ROP.

Inflammation

The effects of the peptides on inflammation is evaluated by measuring the reduction of levels of inflammatory cytokines TNFα and Interferon gamma in the vitreous using the Affymetric Biolplex Luminex bead assay and reduction of microglia activation as determined by IBA 1 immunolabeling of microglia in the retina Cell Death The effects of the peptides on cell death is evaluated by estimating number of cells undergoing apoptosis by TUNEL assay and cell dropout using staining by propidium iodide or DAPI. For evaluation of the peptides in the treatment of diabetic retinopathy, glaucoma, or ROP, cell death is measured in retinal ganglion cells. For evaluation of Retinitis pigmentosa, cell death is measured for photoreceptors. For evaluation of AMD, cell death is measured for photoreceptors and RPE cells.

Vascular Leakage (Macular Edema)

Leakage is measured by live imaging of the retina. Mice are anesthetized using Ketamine 100 mg/Kg, Xylazine 10 mg/Kg, ocular surface lubricated with Optive Lubricant (Allergan), pupils dilated with 0.5% Tropicamide Ophthalmic Solution (Alcon), and animals injected with 100 ul AK-FLUOR solution (10%). Fluorescein images of the retina are acquired using the Phoenix Micron III retinal imager and extent of vascular leakage in the retina is estimated by counts of fluorescent areas. Fluorescent intensity is measured using the NIH Image J software.

Paraffin sections of the retina is also immunolabeled with antibodies for two tight junction proteins in the vasculature—ZO1 and Occludin, which are important to maintaining vessel integrity.

Vitreous levels of VEGF in the diseased retina are measured using the Affymetrix Luminex bead assay and compared to untreated controls and wild type animals. VEGF levels are also be measured by western blot analysis to confirm the luminex bead assays Vascular leakage is also evaluated by estimating pericyte drop out.

To evaluate the peptides for treatment of diabetic retinopathy or ROP, vascular leakage is examined in the inner retina. To evaluate the peptides for treatment of AMD, vascular leakage is examined in the choroidal vasculature and outer retina.

Example 8

Bioavailability and Efficacy of Peptide Analogs in In Vivo Models

From the in vitro P78 peptide analog screening studies, five structurally diverse analogs with best biological activity were selected to test their efficacy in the diabetic mouse eye. In vivo effects of these peptides were tested in the Ins2Akita mouse model of DR, a well-characterized DR model that has a mutation in the insulin gene. Heterozygote Ins2Akita mice (Jackson Lab) become hyperglycemic (HG) at ~4.5 wks of age. RGC death and inflammation occur within the first 4-6 wks of DR and vascular pathology is first noticed ~13 wks after the onset of diabetes. The studies were designed to identify peptide candidates with pleotrophic effects on cell death, inflammation, and vascular leakage in the diabetic retina.

Male hyperglycemic mice with blood glucose levels >300 mg/dL were used and treatments carried as previously described for P78 (Liu et al., 2012, Mol. Med., 18(1): 1387-1401). Diabetic mice were treated 2×/wk for 15 wks at the onset of HG using a single dose of 5 μg/5 μl artificial tears for each drug, a dose at which P78 is effective. Both eyes received the same treatment to avoid drug cross contamination between the eyes of an individual animal. At the end of the longitudinal studies, eyes were enucleated from anesthesized animals, vitreous collected, and retina dissected and embedded in paraffin for morphometric analysis of RGC survival and vascular leakage.

Before the longitudinal efficacy studies were carried out in vivo, the bioavailability of the five analogs was examined in comparison to the parent compound P78 and its active 29-mer derivative, SpxA1.

Peptide Bioavailability in the Retina

Figure 6:
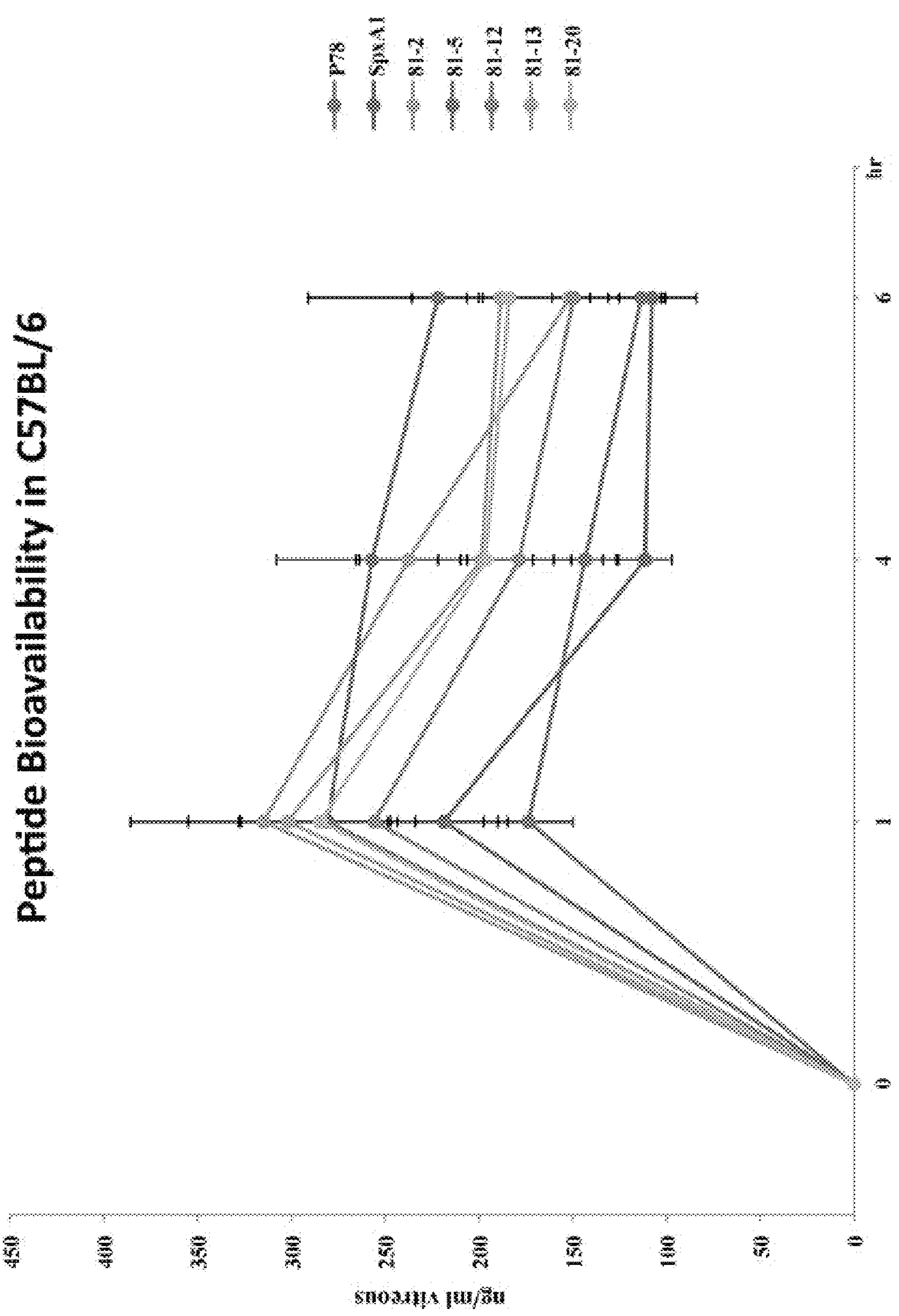
FIG. 6 is a graph depicting the peptide bioavailability of selected peptides in C57BL/6 mice vitreous.

Bioavailability of each peptide was determined in vitreous samples obtained at various time points after eye drops were given. Vitreous samples were harvested from enucleated eyes and immediately analyzed by mass spectrometry. Spectral intensities were compared to spectra of known concentrations of each analog to calculate amounts of peptides reaching the vitreous. The eye drops administered to normal mouse eyes contained 5 μg of the test compound. Bioavailability was studied at three time points: 1, 4, 6 hr using four animals/time point (n=8 eyes). The vitreous was rapidly dissected from each group after the drops were given and immediately analyzed by MALDI TOF. Several of the analogs showed significantly better access to the retina compared to P78 and SpxA1 but all showed peak levels at approximately 1 hr after the drops were administered. Analog 81-5 showed the best stability profile in the vitreous after 6 hr compared to the parent compound and its truncated 29-mer SpxA1. The quantitative bioavailability data obtained by Mass Spectrometry are shown in FIG. 6.

The amount of peptides reaching the retina 1 hr after eye drop administration was also visualized by confocal microscopy. In this experiment, eye drops containing the peptides were given to the diabetic Ins2Akita mice for 1 hr. The animals were then euthanized, eyes dissected, fixed in 4% paraformaldehyde overnight, and whole globes were sectioned in OCT. Sections were then immunolabeled with an antibody again the P78 peptide, which also recognizes the full length PEDF and the analogs. As controls, C57BL/6

Figure 7:
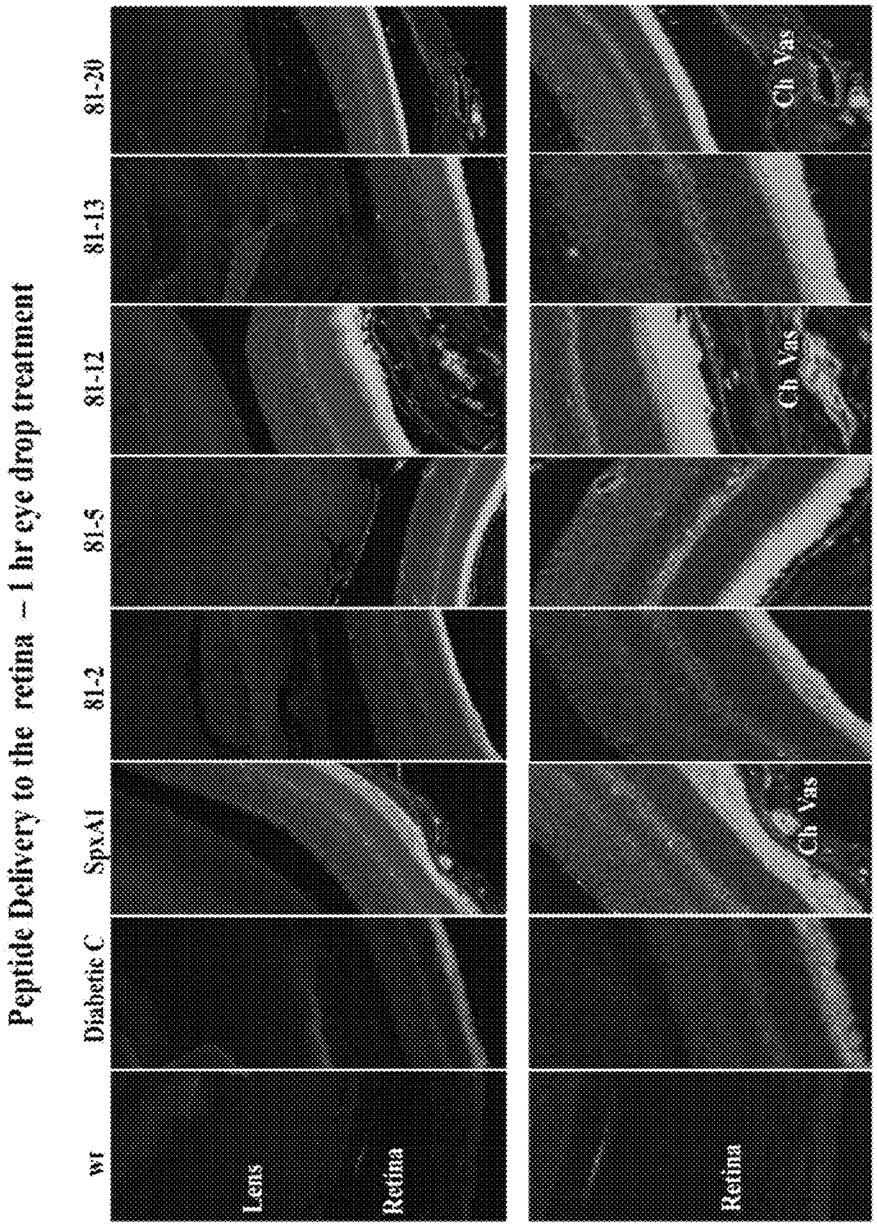
FIG. 7 is a set of images depicting the presence of delivered peptide analogs in the retina layers 1 hour following administrating of peptide eye drops in diabetic Ins2Akita mice.

(wt) and diabetic Ins2Akita mice treated with vehicle (Diabetic Control) were immunolabeled to compare with the peptide treated groups. The data in FIG. 7 shows weak endogenous PEDF staining in the wt retina and an upregulation of endogeneous PEDF in the diabetic control retinas suggesting that in diabetes, PEDF is upregulated, possibly as an endogeneous therapeutic approach by the eye. The intense labeling after the peptide eye drops were given largely represents the peptide analogs present in the retina and indicates that a significant amount of the peptides is delivered to the retina by topical routes. Staining is visible throughout the retina, but is more strongly seen in the choroid and RPE-Photoreceptor layers of the retina. The intense labeling seen in the choroidal vasculature suggests that these vessels may be a route of delivery of these peptides (FIG. 7). Thus, both the mass spectrometry and immunolabeling studies provide strong evidence that these small therapeutic peptides can be delivered to the back of the eye when administered topically and is represents a non-invasive approach to treating retinal diseases.

Reduction of Inflammation

Figure 8:
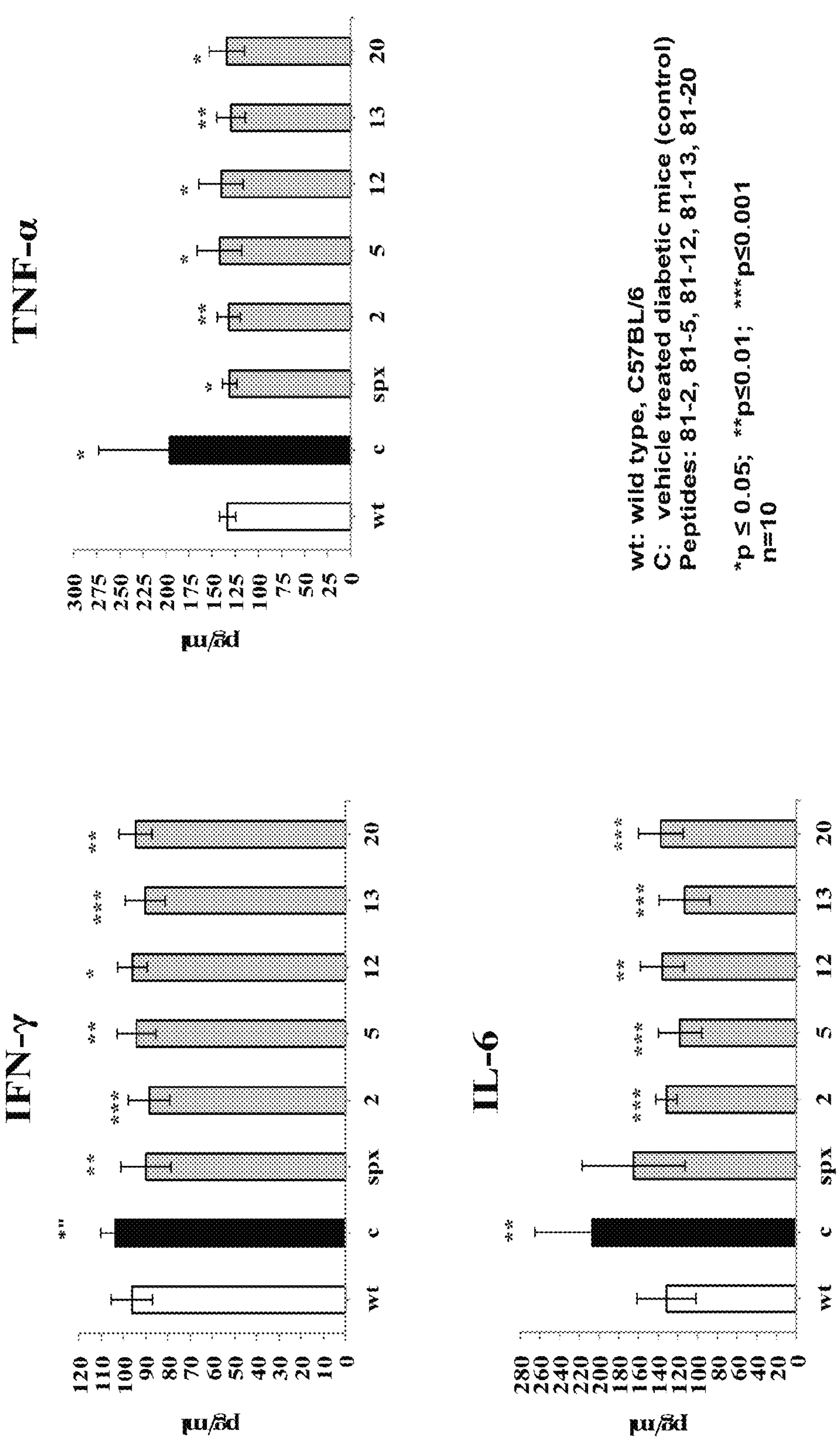
FIG. 8 is a set of graphs demonstrating the reduction of proinflammatory cytokines (IFN-γ, TNF-α, and IL-6) in diabetic mice, mediated by administration of selected peptides.

Vitreous samples harvested at the termination of the 15 weeks efficacy study were analyzed to detect levels of proinflammatory cytokines using the Bioplex multiplex platform. This system utilizes polystyrene luminex bead arrays and the xMAP technology. Target inflammatory markers examined were TNFα, IFNγ, and IL-6, and the major proangiogenesis cytokine, VEGFA. FIG. 8 depicts the expected rise of the proinflammatory cytokines in the diabetic retina compared to wt samples and a marked reduction in all three by the P78 peptide analogs, mimicking the results of the in vitro studies. While the peptides showed similar effects in reducing TNFα and IFNγ, 81-5 and 81-13 showed slightly but significantly better effects in reducing IL-6 (FIG. 8).

VEGF Levels

Figure 9:
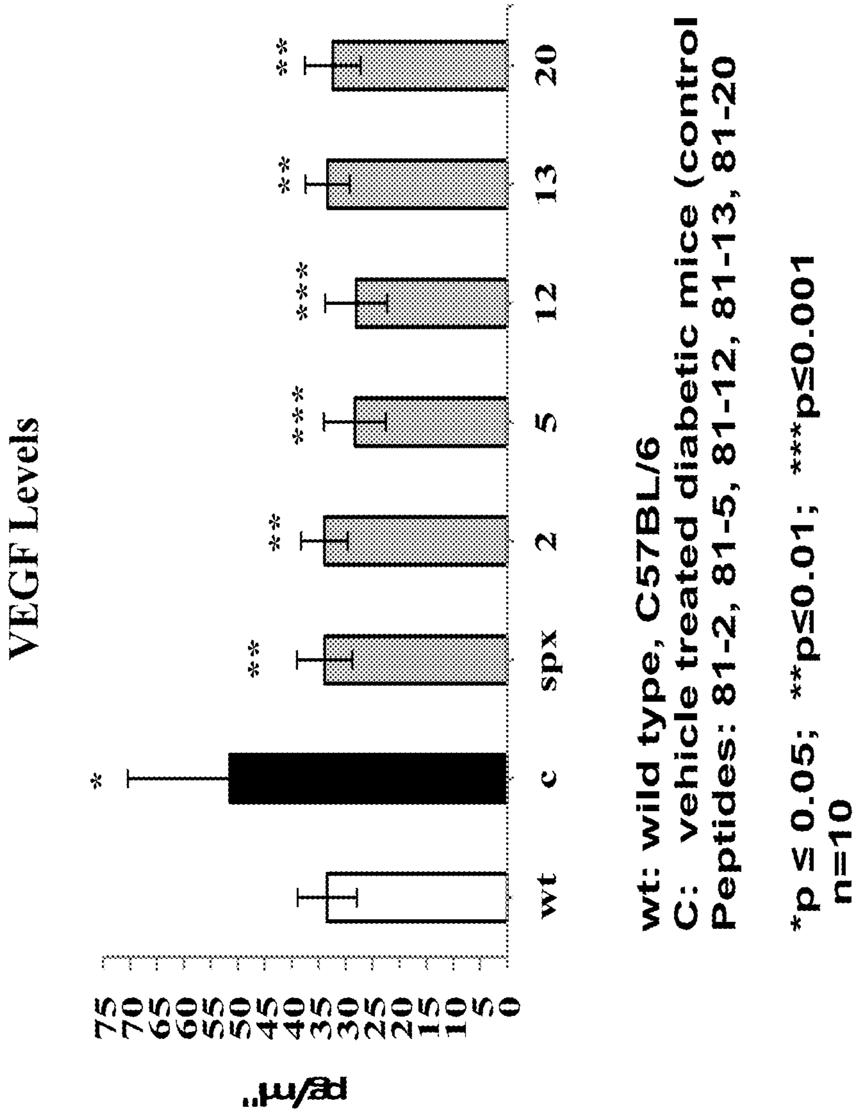
FIG. 9 is a graph demonstrating the reduction in VEGF levels in diabetic mice, mediated by administration of selected peptides.

Levels of VEGF were also quantitated in the vitreous of the 15 wks peptide treated and control groups using the Luminex bead technology. From this experiment, a significant increase in VEGF levels was observed, as shown before (Liu et al., 2012, Mol Med, 18(1): 1387-1401) in the vehicle treated diabetic controls compared to the age and weight matched wild type C57BL/6. All peptide treatments resulted in reduced levels of VEGF in the vitreous relative to the diabetic controls with analogs 81-5 and 81-12 slightly but significantly more effective (FIG. 9).

Reduction in Vascular Leakage

Figure 10:
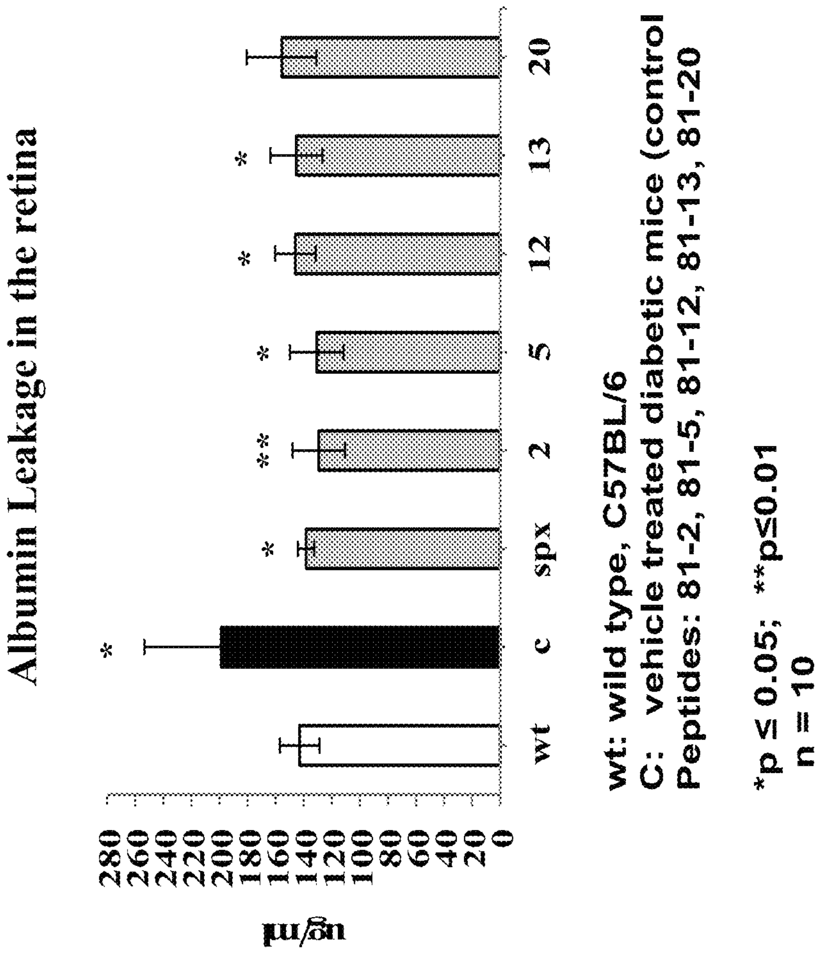
FIG. 10 is a graph demonstrating the reduction in albumin leakage in the retina of diabetic mice, mediated by administration of selected peptides.
Figure 11:
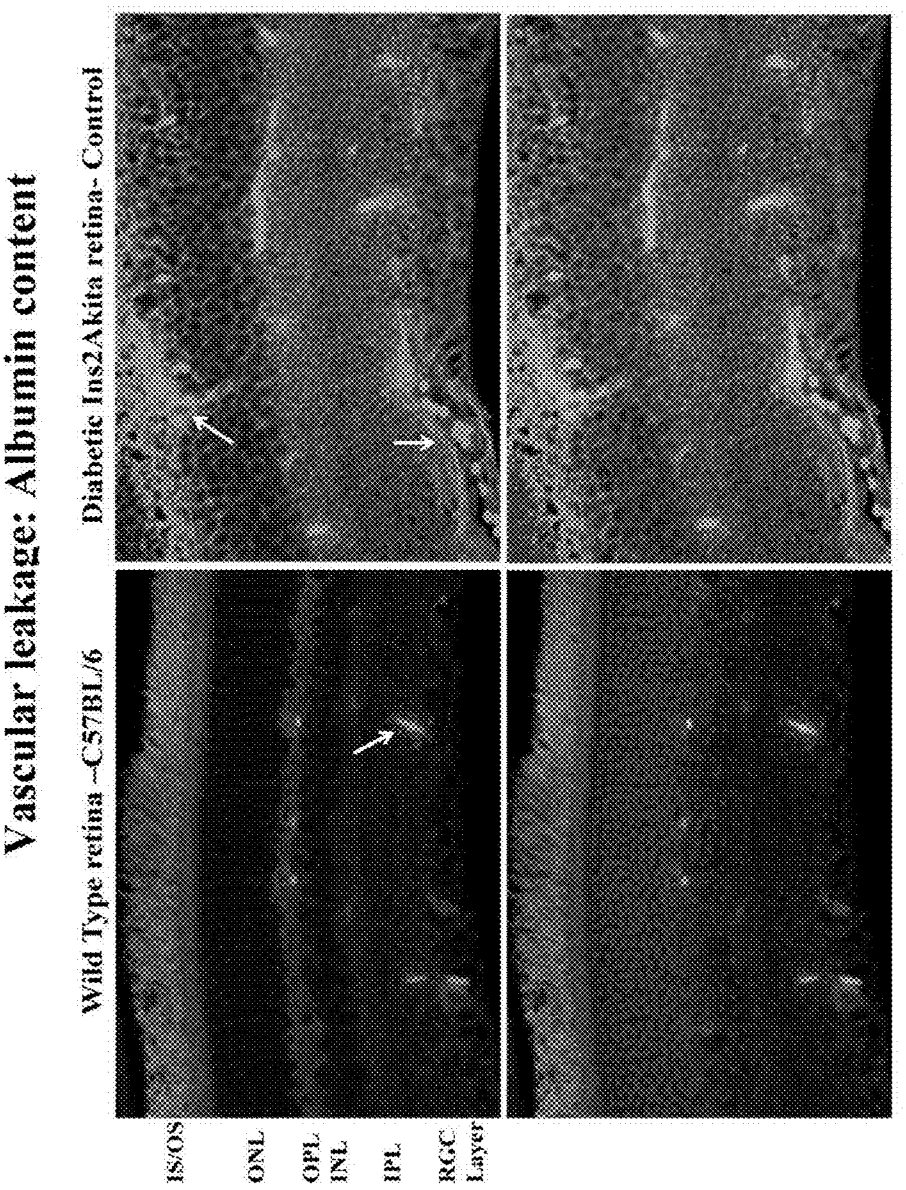
FIG. 11 is a set of images (obtained at 20× magnification) depicting retinal sections labeled for albumin, demonstrating that diabetic retinas contained higher levels of albumin throughout the retinal parenchyma and in blood vessels.
Figure 12:
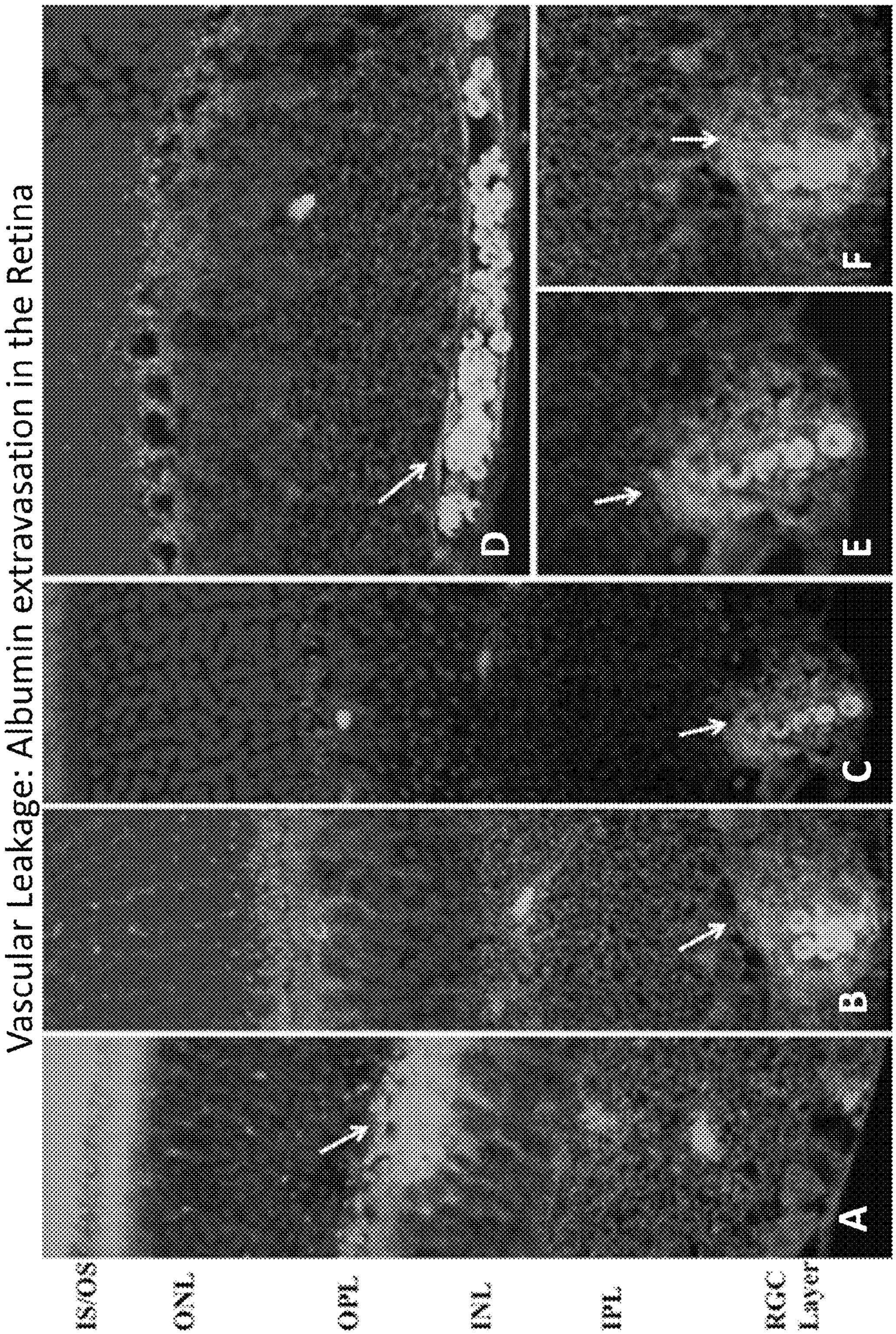
FIG. 12, comprising
Figure 13:
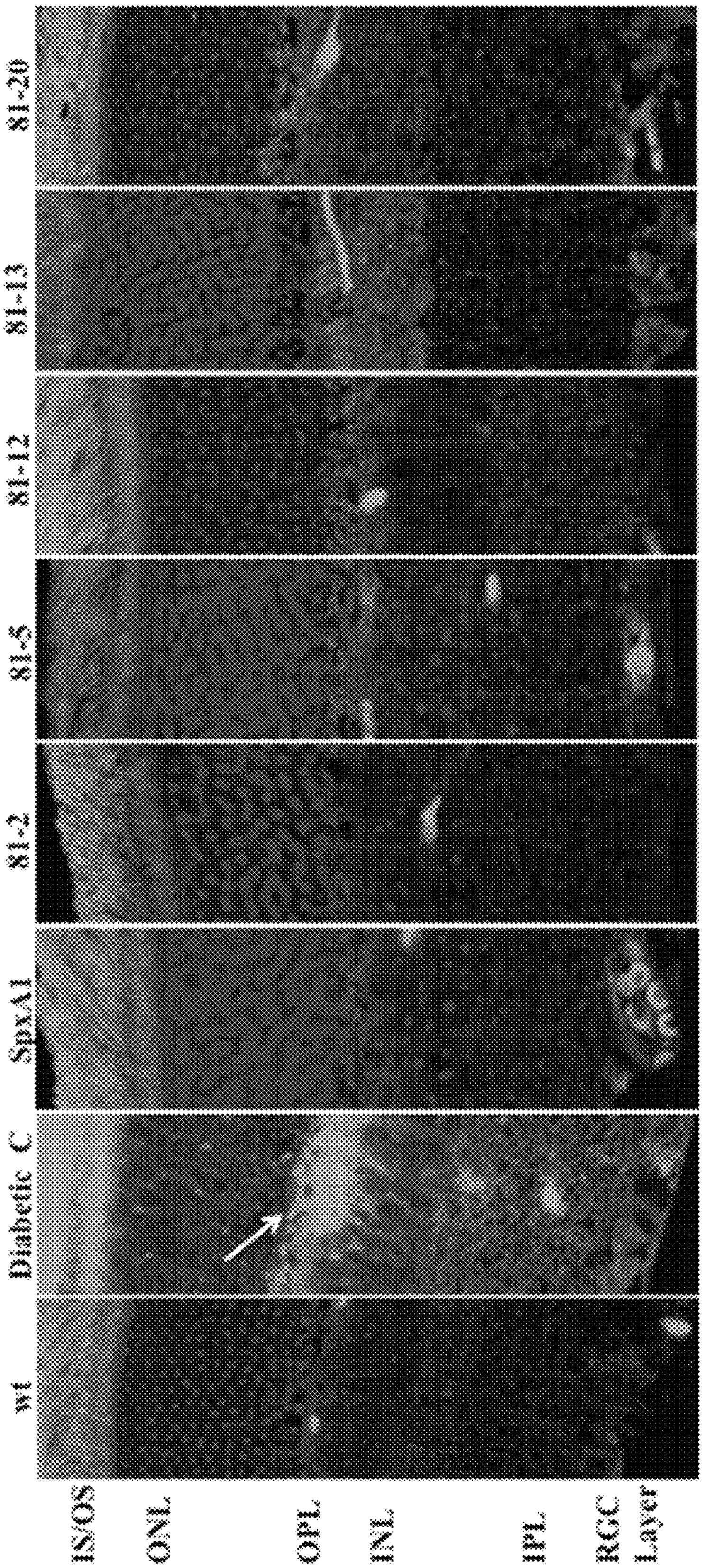
FIG. 13 is a set of images depicting the effects of the selected peptides on vascular leakage as measured by albumin extravasation into the retina.

Vascular hemorrhaging was quantitated by measuring extent of albumin extravasation in the retina by leaky retinal vessels. An ELISA approach (FIG. 10) was used to quantitate extent of albumin leakage from blood vessels into the retina parenchyma, and confocal microscopy was performed using an antibody to mouse albumin to detect changes in albumin levels in the controls and treatment groups (FIG. 11). FIG. 10 demonstrates that there was a significant increase in vascular leakage in the diabetic control retinas compared to the wild type animals at 15 weeks of diabetes. The selected panel of analogs was also effective in reducing albumin content in the retina with Spx, 81-2 and 81-5 having a small but significant advantage over the other analogs. This analysis was confirmed by microscopic evidence on retinal sections immunolabeled for albumin. From this study, it was evident that the diabetic retinas contained higher levels of albumin throughout the retinal parenchyma and in blood vessels (arrows) as show in FIG. 11 (20×). Higher magnification (FIG. 12) of these retinal images (40×) shows increased albumin levels in the photoreceptor inner and outer segment areas, vascular leakage into the retinal parenchyma in the outer plexiform layers (OPL; FIG. 12A, arrow) and the retinal ganglion cell layer (RGC; FIG. 12B-FIG. 12C, FIG. 12E-FIG. 12F; arrows), and a large blood vessel in the RGC layer (FIG. 12D). The data suggest that not only is there leakage from the microvessels in the inner retina but that the RPE-Choroidal vasculature adjacent to the photoreceptor layer maybe compromised in diabetic retinopathy. In FIG. 13, the effects of the peptides on vascular leakage as measured by albumin extravasation into the retina are shown. All peptide-treated retinas immunolabeled with the albumin antibody showed less fluorescence intensity throughout the retina including the photoreceptor IS/OS compared to the diabetic controls. Albumin levels were comparable to the wild type retinas although inner retinal microvessels appeared larger than the wt. The microscopy data thus confirms the ELISA quantitative measurements (FIG. 10) which argued for increased vascular leakage in the diabetic retina and a reduction after peptide treatments.

RGC Survival.

Figure 14:
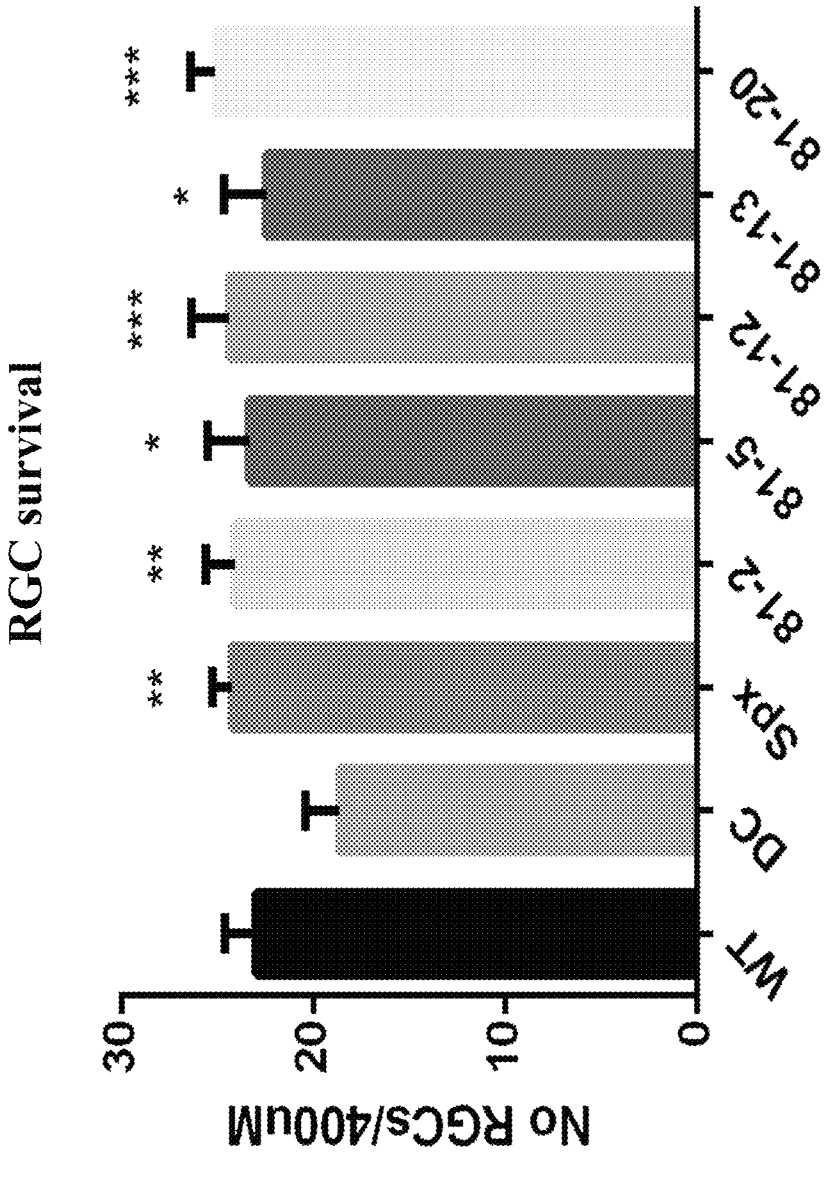
FIG. 14 is a graph depicting an increase in the survival of retinal ganglion cells in peptide treated diabetic mice.

RGC loss occurs early in diabetic retinopathy in both humans and rodents. In this study retinal sections from peptide treated and control groups were stained with DAPI to manually count the nuclei of surviving RGCs. Six non-serial sections from each eye in the peripheral and central retinas were used for morphometric analysis. Stained nuclei in the RGC layer were counted in all retinal eccentricities using high-resolution confocal optical slices of DAPI stained retinas. Cell counts were taken from 6×250 mm zones along the length of the retina from centrally located fields adjacent to the optic nerve to the periphery. 6 fields/retina were analyzed and data presented as the avg # cells/400 μM. (n=6). The results of this experiment are presented in FIG. 14-FIG. 15. The morphometrics data in FIG. 14 show a decrease in the number of surviving retinal ganglion cells (RGCs) in untreated diabetic control retinas (DC) as previously demonstrated. The extent of the neuroprotective actions of the peptide treatments on these cells was also significant for each treatment and comparable RGC counts in the wild type retina. The efficacy profiles of this group of peptides for RGC survival are comparable and suggest that this set of P78 analogs are clearly potent in preventing diabetes-induced degeneration of RGC cells. Whether the neuroprotective effect of the analogs is a direct action on RGCs themselves or is indirectly mediated through the reduction of proinflammatory cytokines is worthy of further investigation. Although the peptide analogs are structurally diverse, the modifications were conservative. Although they are much shorter fragments that P78, each contain the same core group of peptides. These peptides were selected because of their in vitro activity was superior to P78. Without a doubt, the in vitro and in vivo efficacy profiles indicate that these peptides contain the active core sequence of P78 and constitute a panel of therapeutic analogs for DR.

Figure 15:
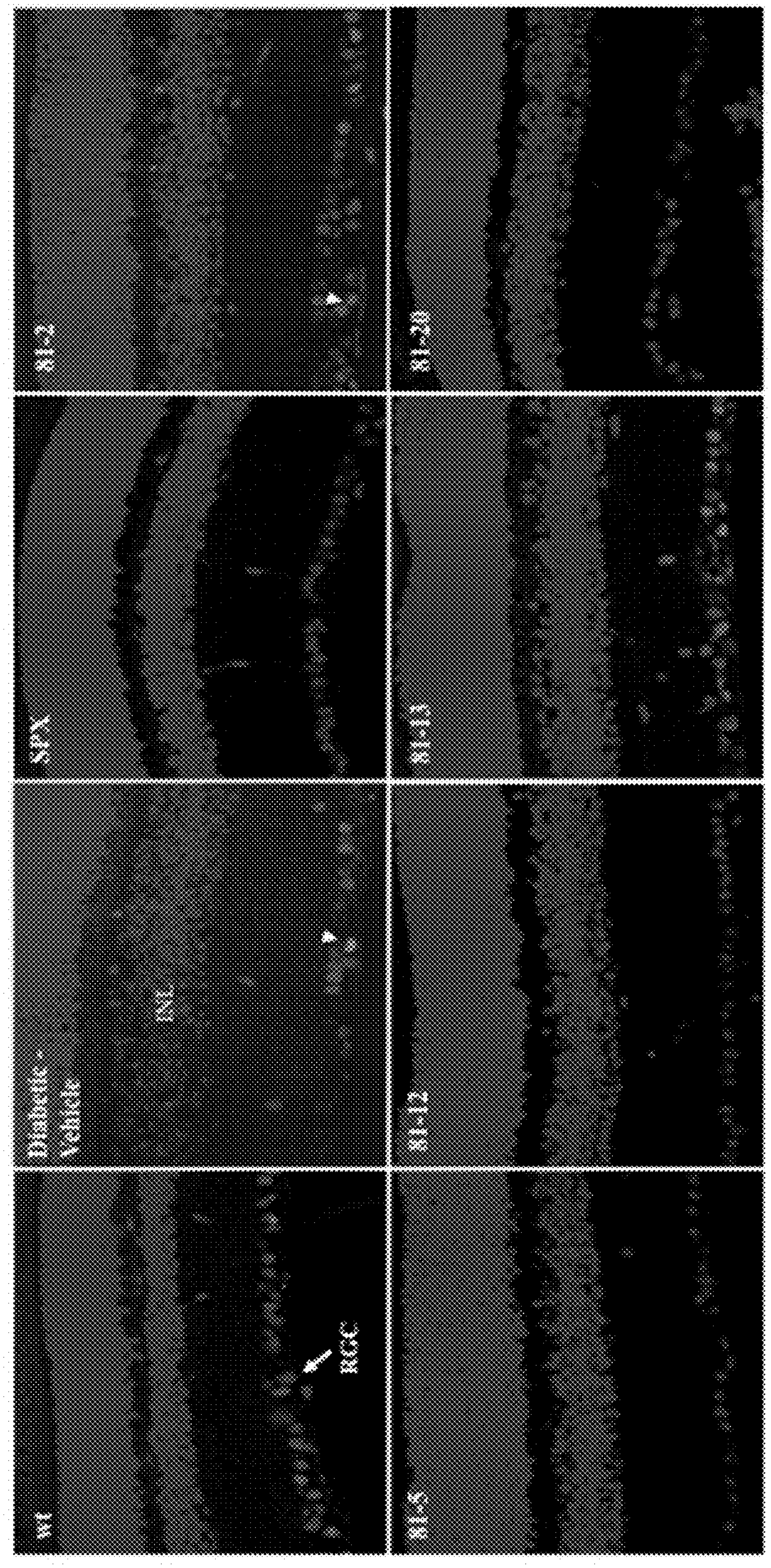
FIG. 15 is a set of images depicting DAPI and TUNEL stained retinas of peptide treated diabetic mice and controls.

The micrographs in FIG. 15, are representative images of DAPI and TUNEL stained retinas of peptide treated diabetic mice and control groups. The RGC layer is indicated as the single cell layer in the inner retina. DAPI staining was used to count the nuclei in the RGC layer and TUNEL assay (green fluorescence) was used to detect ongoing cell death after treatment. Several of the peptides showed little ongoing cell death in the RGC layer and increased numbers of surviving RGCs compared to the vehicle treated diabetic animals. Of interest is the abnormal morphology and disorganization of the nuclei comprising the inner nuclear layer (INL) in the untreated diabetic group. The INL also appears to be affected by the peptide treatments and is shown to be more like the wt after treatment.

Bioavailability of Peptides in Primate Eyes

From the studies using the DR mouse model, two active, structurally diverse peptides 81-5 and 81-13 were selected to test their availability in the primate eye when given topically. There are substantial differences between the eyes of rodents, primates, and humans. The most obvious is size of the aqueous and vitreous fluid compartments. Fluid flow forward from the ciliary body in primates/humans is countercurrent to drug movement to the back of the eye and may influence drug concentrations in the vitreous. In this study, it was examined whether the selected compounds had access to the retina when given topically to primate eyes as they do in rodents. Peptide doses used were scaled up by 8-20 fold as an estimate to account for differences in eye volume between rodents and primates.

Adult males and females were equally distributed into 3 treatment groups (Table 3) and randomized by weight criteria. Animals were fasted overnight then sedated with ketamine (8 mg/kg, I.M) and xylazine (1.6 mg/kg, I.M) prior to all procedures. Two monkeys received a topical dose of 40 μg (40 μl) of 81-5 OU (both eyes) and underwent vitreocentesis at ~1 hr (Group 1) after dosing. Four monkeys received a topical dose of 100 μg (50 μl) of 81-13 OU and underwent vitreocentesis at ~1 hr (Group 2; 2 animals) or ~2 hr (group 3; 2 animals) after dosing (Table 3). Animals remained under continuous sedation prior to vitreous humor collection. Eyes were manually blinked (4 blinks/min) for 2 minutes after dosing to mimic ocular delivery in a non-sedated animal. Prior to vitreous humor collection, topical local anesthesia was administered (0.5% proparacaine) and eyes disinfected with 5% Betadine. A 25-gauge, 0.5 inch needle was placed 2 mm posterior to the limbus in the inferior temporal quadrant, targeting the central vitreous. A volume of 100 μL of vitreous humor was aspirated gently from the right (OD) and left (OS) eyes and transferred to labeled pre-tared cryovials. A larger volume of vitreous humor (200 μl) was withdrawn into the syringe from animal X429 because the operator had to pull harder to overcome the viscosity of vitreous. The cryovials were flash frozen in liquid nitrogen. Vitreous humor collection was followed by topical administration of a triple antibiotic ointment (neomycin/polymyxin B sulfates/bacitracin zinc). Animals were returned to the colony after vitreocentesis. Since both eyes were used for the same peptide, the n value was 4 for each peptide/dose/time.

Samples were analyzed by mass spectrometry and concentrations calculated using a standard curve that plotted intensity vs known concentration. Although the levels of the peptides reaching the vitreous compartment in the primate eye reached therapeutic levels (bioactivity=20-50 ng/ml), peptide concentrations were lowered by ~2 fold than that seen in the rodent eyes possibly because of the drug:volume ratio and the countercurrent fluid flow forward in the anterior chamber of the eye. However, the study suggested that increasing dosage may result in increased concentrations of the drugs in the vitreous compartment as observed with peptide 81-13 which showed comparable bioavailability profiles with 81-5 in rodents. The peptide concentration in the vitreous was not significantly different between the 1 and 2 hr treatment and was even a bit lower at 2 hr, suggesting that peak concentrations were similar to the rodent at 1 hr after topical administration.

In summary, the in vivo data in diabetic mice indicate that the selected set of P78 analogs that showed the best activity in vitro were also active in vivo in reducing hallmark pathologies of diabetic retinopathy, namely inflammation, vascular leakage, and cell degeneration. While the minor differences in efficacy in vivo was unexpected, these structurally diverse molecules represent a therapeutic panel of active compounds for diabetic retinopathy and have advantages for the development of more effective next generation compounds. The primate ocular bioavailability study is very encouraging and holds promise for delivery of these small therapeutic peptides to the human eye to treat ocular diseases.

Example 9

Regulation of Endothelial Tube Formation—An Angiogenesis Assay

Human dermal fibroblasts were cultured at $1\times10^5$/well in IncuCyte seeding medium (Essen Bioscience) in 96 wells plates for 1 hr. Medium was removed and replaced with complete IncuCyte growth medium (Essen Bioscience). Human umbilical vein endothelial cells (HUVEC) containing a green fluorescent marker (HUVEC CytoLight green) cells at 2000 cells/well were/well to attached dermal fibroblasts cultures and placed in the IncuCyte Zoom fluorescent and phase contrast multiplex imaging incubator (Essen BioScience). Twenty four hours later 4 ng/ml VEGF was added to all wells and 100 nM/ml PEDF peptides added to test wells. Cultures containing VEGF alone were used as

TABLE 3

Peptide bioavailability in primate (Vervets) eyes

| Group | Animal ID | Sex | Body weight (Kg) | Eye | Test article | Dose/ Topical | Vitreous humor collected after dosing | Volume collected | Mass Spec Avg Conc ng/ml |
|---|---|---|---|---|---|---|---|---|---|
| 1 | Z998 | Male | 6.54 | OU | 81-5 | 40 μg/40 μL/eye | OD: 67 min<br>OS: 69 min | OD: 100 μL<br>OS: 100 μL | |
| 1 | K099 | Female | 3.78 | OU | 81-5 | 40 μg/40 μL/eye | OD: 65 min<br>OS: 66 min | OD: 100 μL<br>OS: 100 μL | Group 1 (n = 4)<br>158.5 ± 15.5 |
| 2 | V715 | Female | 4.68 | OU | 81-13 | 100 μg/50 μL/eye | OD: 59 min<br>OS: 60 min | OD: 100 μL<br>OS: 100 μL | |
| 2 | K146 | Male | 5.92 | OU | 81-13 | 100 μg/50 μL/eye | OD: 58 min<br>OS: 64 min | OD: 100 μL<br>OS: 100 μL | Group 2 (n = 4)<br>237.5 ± 32.5 |
| 3 | X429 | Female | 4.68 | OU | 81-13 | 100 μg/50 μL/eye | OD: 120 min<br>OS: 118 min | OD: 100 μL<br>OS: 200 μL | |
| 3 | K169 | Male | 8.28 | OU | 81-13 | 100 μg/50 μL/eye | OD: 125 min<br>OS: 128 mi | OD: 100 μL<br>OS: 100 μL | Group 3 (n = 4)<br>212.5 ± 15.0 |

positive controls and those containing 100 μM Suramin (VEGF inhibitor) used as negative controls. The cultures were placed at 37° C. in the Incucyte Zoom and HUVEC tube length networks measured over a 12 day incubation period using the Incucyte CellPlayer Angiogenesis software module and interface systems. Media was refreshed every 3-4 days.

Figure 16A:
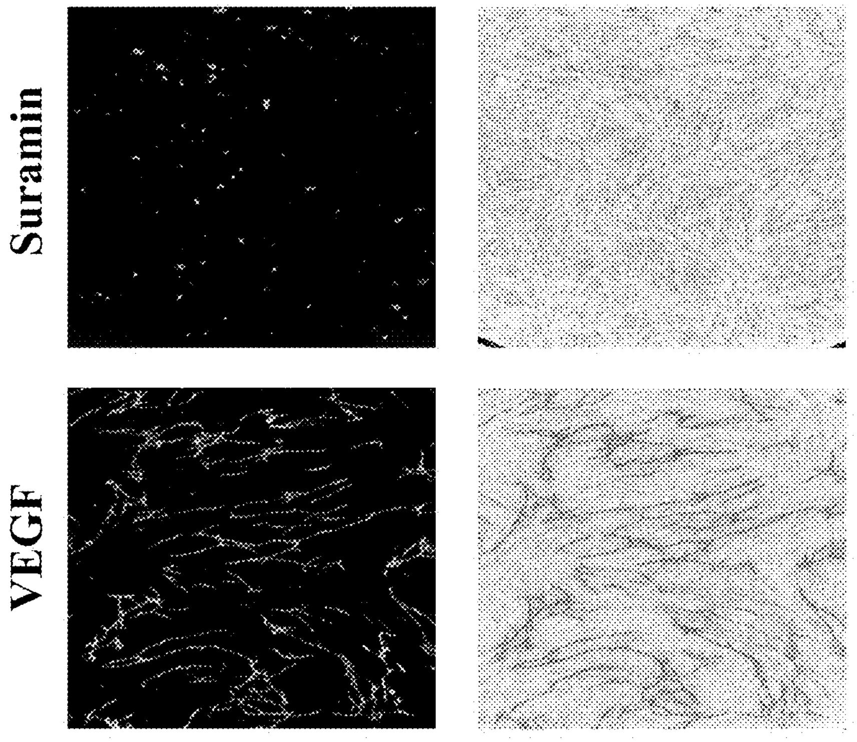
FIG. 16A through FIG. 16C, depicts the results of experiments investigating the activity of the PEDF-derived peptides on HUVEC tube formation. Representative images of VEGF-mediated HUVEC tube formation are show (blue) on layers of human dermal fibroblast (grey). Effects of VEGF alone (4 ng/mL), and Suramin (100 μM) are shown in FIG. 16A, while the effects of PEDF peptides P78, 81-2, 81-5, 81-12, 81-13, 81-20 (100 nM) are shown in FIG. 16B. Results depict HUVEC tube formation over 12 days. HUVEC CytoLight green (green) represent endothelial cells not forming tubes. The data in triplicate cultures is quantified in the graphs of FIG. 16C, showing the average HUVEC network length over 12 days.
Figure 16B:
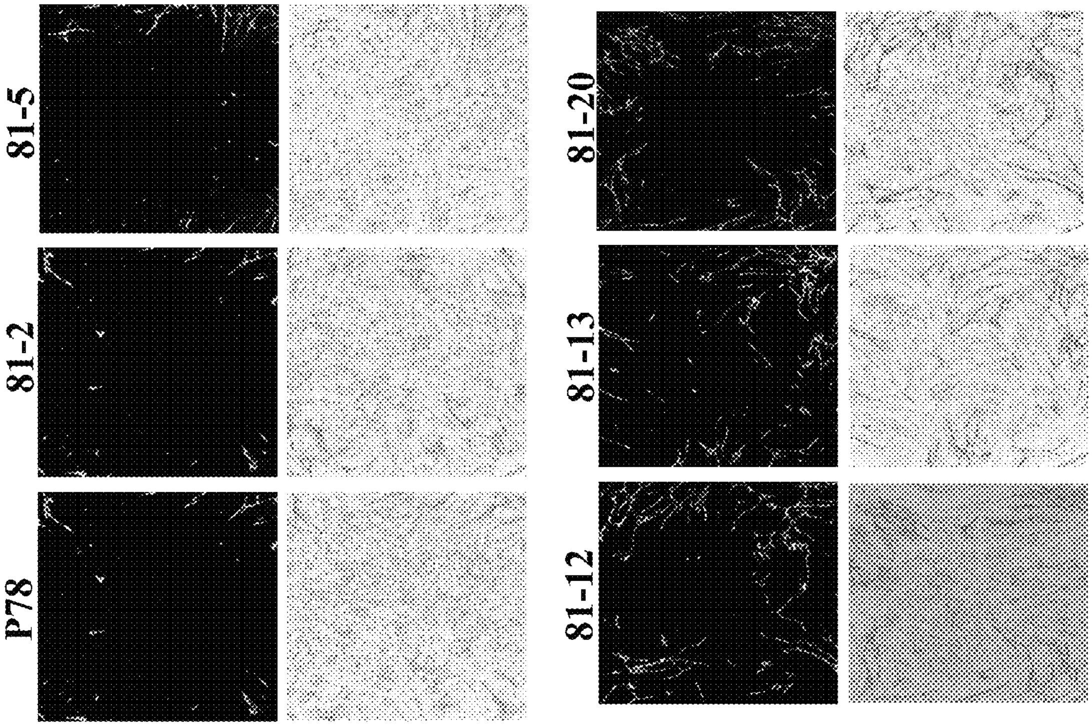
Figure 16C:
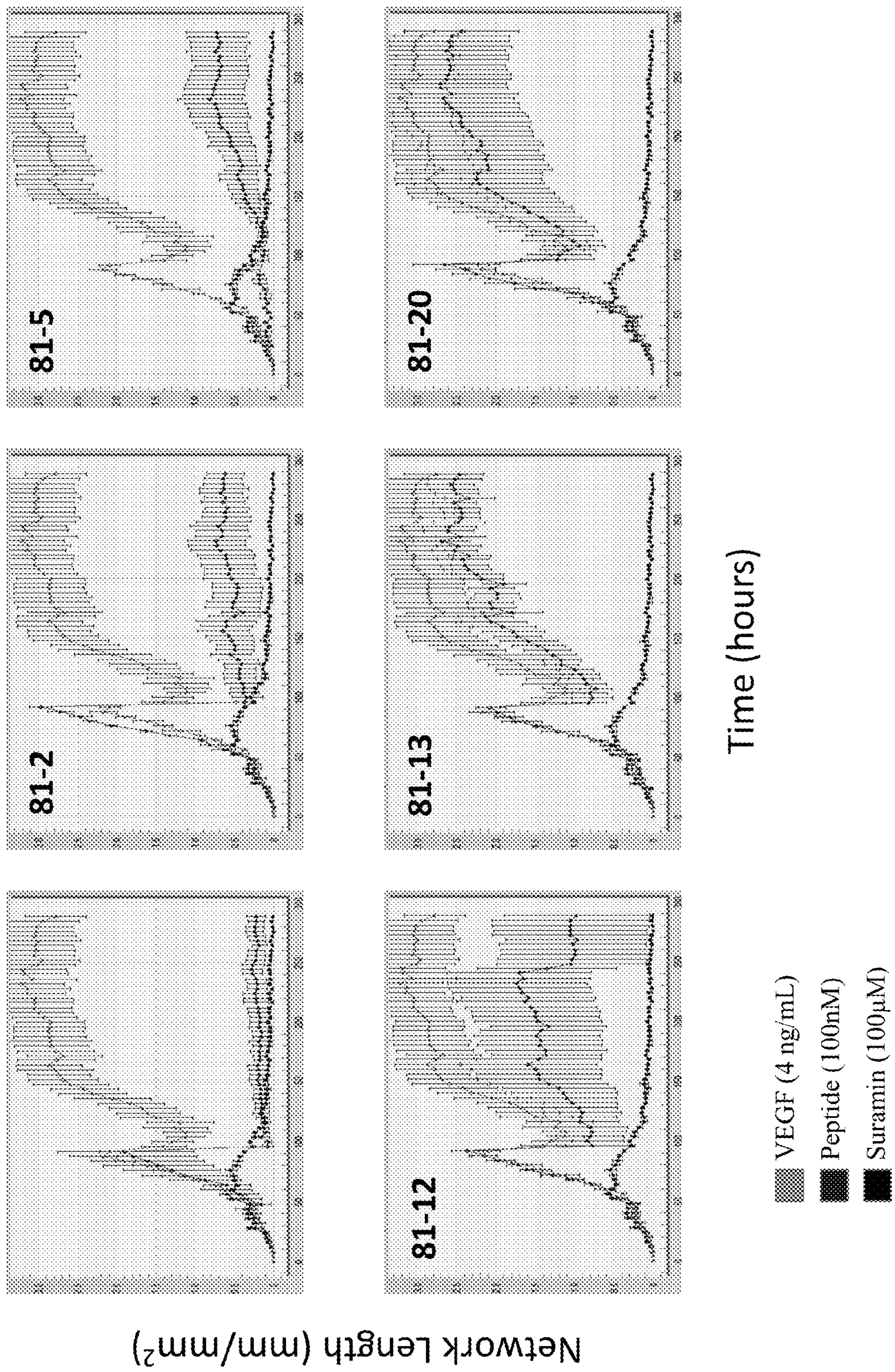

Formation of tubes by HUVEC was inhibited by the selected peptides compared to VEGF. The most potent were P78, the parent PEDF active peptide, 81-2, and 81-5. The other three peptides: 81-12, 81-13, and 81-20 prevented tube formation compared to VEGF but less effective. Representative micrographs of HUVEC tube induction for VEGF alone and 100 μM Suramin treatment are shown in FIG. 16A, while micrographs of HUVEC tube formation induction for peptide treatments are shown in FIG. 16B. Quantitative data of triplicate experiments is shown in FIG. 16C.

Example 10

Transcription Factor Targets of PEDF-Derived Peptides

Activation of transcription factors by P78, spx or 81-5 was measured in human RPE cells. The Affymetrix Procarta Multiplex Transcription factor panel (Affymetrix, Inc. Santa Clara, Calif.) was used to obtain quantitative measurement of DNA binding activity of 44 transcription factors. Cells were seeded at $1\times10^5$ cells/ml in 6 well plates. Cells were treated with 50 nM peptides in 2% FBS medium for 48 hr, peptides were supplied twice after 24 hr. Cells were harvested using Buffer A working reagent (250 μl well)(1 ml Buffer A: 10 μl DTT, 10 μl protease inhibitor, 10 μl phosphatase inhibitor I, 10 μl phosphatase inhibitor II) and centrifuged at 14,000×g for 3 min at 4° C. Supernatant containing cytoplasmic proteins was collected and protein concentration estimated using the BioRad DC protein assay. To the nuclear pellets, 30 μl/well buffer B (1 ml Buffer B: 10 μl DTT, 10 μl protease inhibitor, 10 μl phosphatase inhibitor I) was added and the samples incubated for 2 hours at 200 rpm. Supernatant containing nuclear proteins was collected by centrifugation at 14,000×g for 5 min at 4° C. and protein concentration measured using Bio-Rad DC protein assay. To form transcription factor (TF) protein/DNA complexes, 2 μg (5 μl) nuclear or cytoplasmic proteins, 10 μl biotin-labeled DNA binding probes (C is elements; Detection probes, TF panel 2) and 5 μl of nuclease-free distilled water were added to each well of a PCR plate and incubated at 15° C. for 30 min using a PCR machine. 20 μl ice-cold binding buffer was added to each well containing the TF-DNA complexes and 30 μl sample from each well transferred to a prewashed separation plate and incubated on ice for 30 min. The TF-DNA complexes were bound to a semi-porous filter using a separation plate. Unbound biotin-labeled DNA binding probes and proteins were removed by washing and the DNA complexes were collected by centrifugation using 563×g for 3 min at 4° C. DNA complexes were denatured at 95° C. for 5 min using a PCR machine, then added to prewashed TF-specific antisense conjugated beads (capture beads, TF panel 2, Affymetrix), and incubated for 10 min at RT with constant shaking at 500 rpm. Samples were then transferred to a 50° C. incubator for 30 min without shaking. Beads were subsequently washed by vacuum filtration and incubated with streptavidin-PE (Affymetrix) for 30 min at room temperature with shaking at 500 rpm. The beads were washed again, resuspended with reading buffer, and incubated for 5 min at room temperature. DNA binding activity of the transcription factors was measured using the Bio-Plex 200 system (bio-Rad) and the xMAP technology.

P78 regulated transcription factors were also identified in the mouse retina. Diabetic Ins2Akita mice were infused with 0.5 mg/kg/day P78 for 6 weeks constant infusion using Alzet pumps. Controls were given PBS alone. Retinas of age-matched normal C57BL/6, diabetic mice treated with vehicle alone, and P78 treated animals were dissected and nuclear extracts collected.

Figure 17:
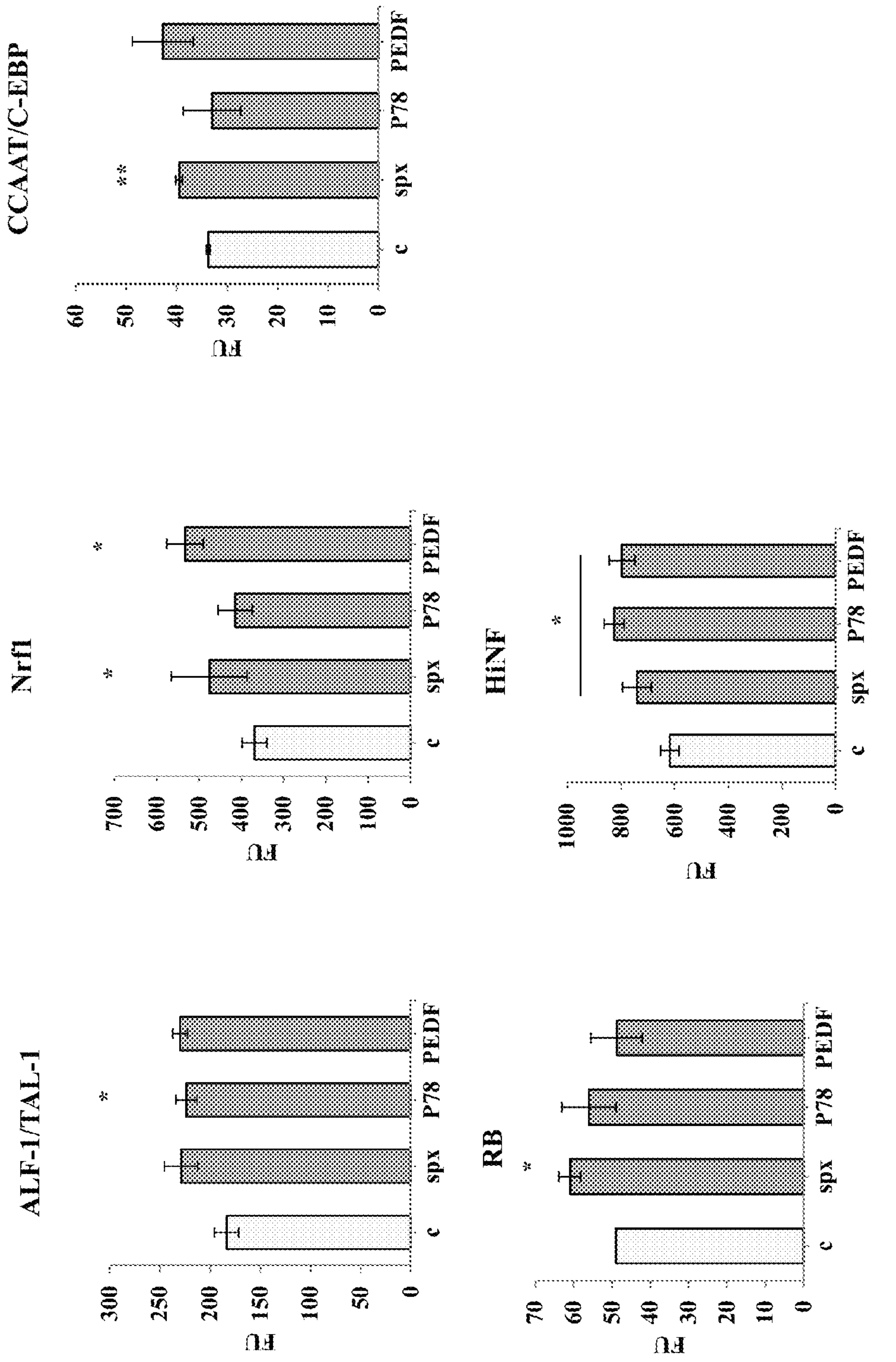
FIG. 17 is set of graphs depicting the regulation of transcription factors by PEDF-derived peptides. The demonstrates suggests that PEDF and the active peptide region (P78) or a truncated sequence of this region (Spx) regulates transcription factors (TFs) that control expression of a wide range of genes that are involved in varied and complementary processes. These include TFs regulating genotoxic stress, environmental stress, and apoptosis (HiNF, Nrfl), cell cycle progression and cell differentiation (RB), and TFs controlling ER stress and inflammatory response (CCAAT/C-EBP).

It was observed that PEDF and the active peptide region (P78) or a truncated sequence of this region (spx) regulates transcription factors (TFs) that control expression of a wide range of genes that are involved in varied and complementary processes (FIG. 17). These include TFs regulating genotoxic stress, environmental stress, and apoptosis (HiNF, Nrfl), cell cycle progression and cell differentiation (RB), and TFs controlling ER stress and inflammatory response (CCAAT/C-EBP).

Example 11

Regulation of Inflammatory Cytokines by PEDF-Derived Peptides

Human Muller glia cells (MIO-M1) were seeded out at a density of $1\times10^5$ in DMEM growth medium. Cultures were treated with 25 nM peptides at the time of seeding for 48 hours. Conditioned medium was harvested by centrifugation and 50 μL, was analyzed using a focused proteomics approach of a multiplex panel of 44 inflammatory Luminex cytokine (Affymetrix Procarta cytokine profiling panel). Analysis was carried out using the xMAP technology and BioRad Manager 4.1 software.

The analysis (FIG. 18A and FIG. 18B) confirms the effects of the selected panel of active PEDF peptides on the regulation of pro-inflammatory cytokines in human RPE cells and the diabetic retina. These results are consistent with previous findings in human RPE cells and in vivo work, and suggest that Muller glia cells are a key target of the peptides.

Figure 18A:
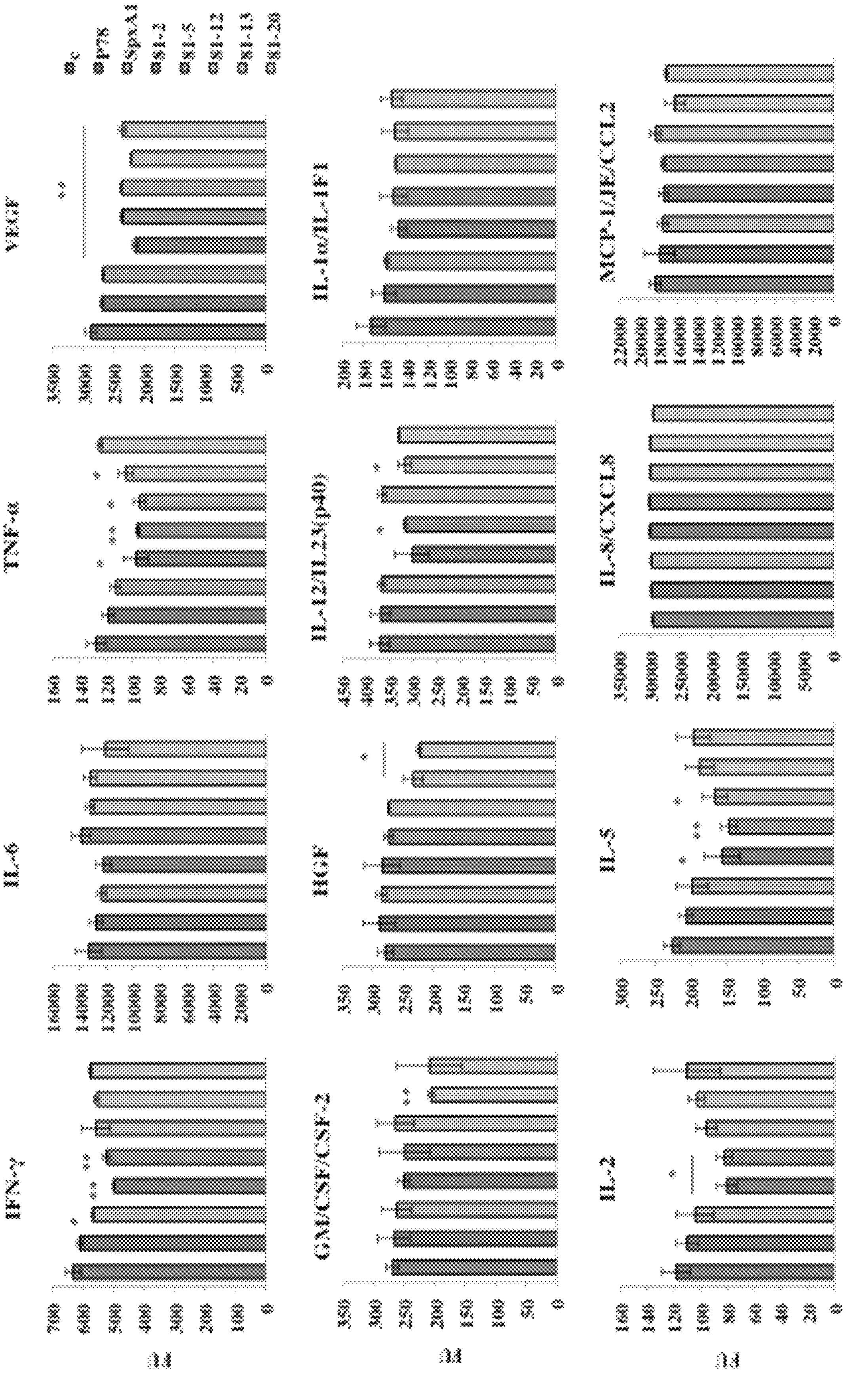
FIG. 18A and FIG. 18B, depicts the results of experiments investigating the regulation of inflammatory cytokines by PEDF-derived peptides. Each graph depicts the regulation of a particular cytokine for the various treatments (from left to right—control, P78, SpxA1, 81-2, 81-5, 81-12, 81-13, and 81-20).
Figure 18B:
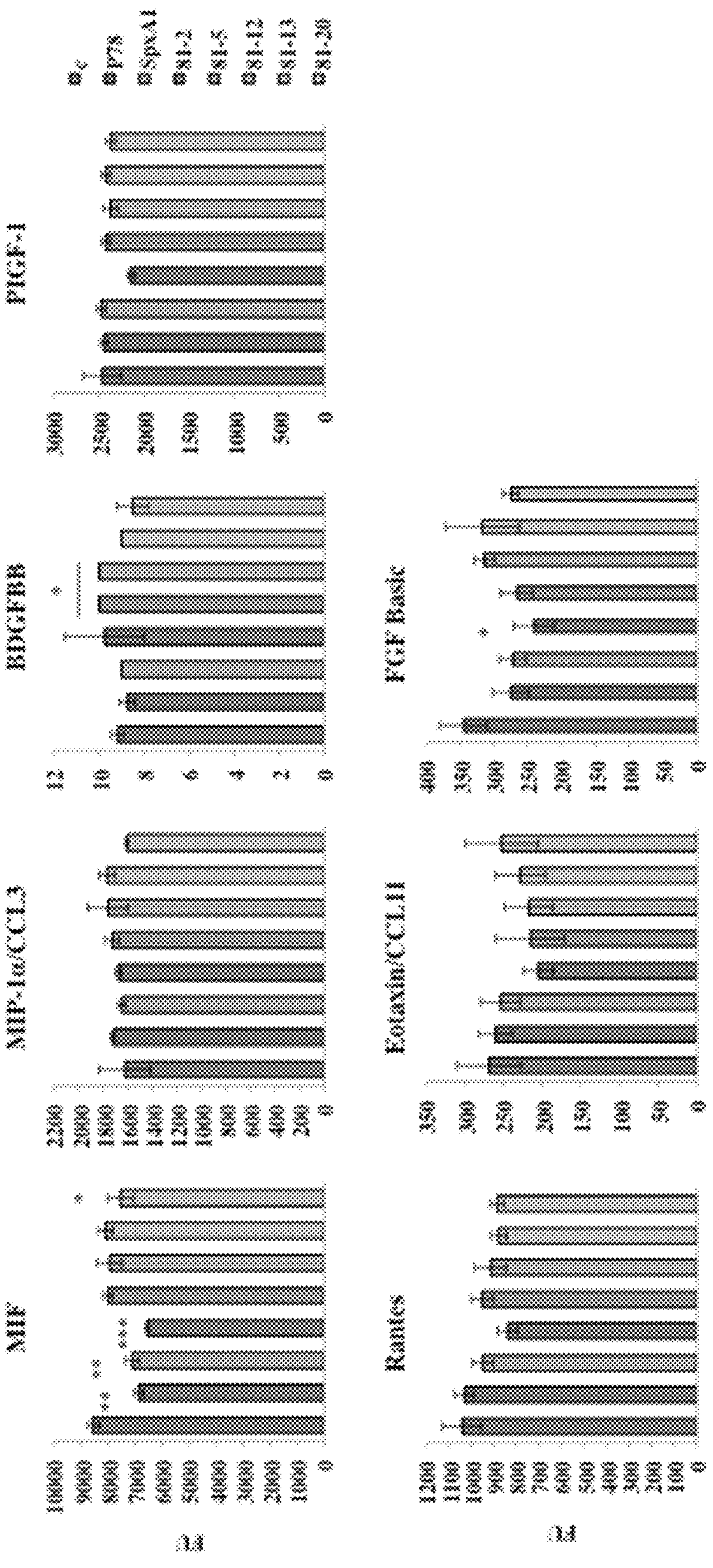

In the retina, Muller Glia cells are highly reactive to retinal injury including those caused by rises in glucose levels. Their reactivity is used as a molecular index of pathological occurrences in the retina. The major proinflammatory cytokines regulated include IFN-γ, TNF-α, IL-2, IL-5 (FIG. 18A) with the peptides showing varied effects on these cytokines but several were more effective than the parent P78 peptide fragment. In addition, these cells are a major producer of VEGF in the retina and these peptides show better effects than P78 in reducing its production levels by these cells (FIG. 18A). This data again suggests that a major target of the PEDF peptide analogs is towards inflammatory molecules and VEGF in the retina.

Example 12

Peptide and Nucleic acid Sequences

Presented herein are the peptide sequences and the calculated nucleic acid sequences for the peptides. The amino acid sequences were calculated using EMBOSS Backtranambig—a program that reads a protein sequence and writes the nucleic acid sequence it could have come from. It does this by using nucleotide ambiguity codes that represent all possible codons for each amino acid (Table 4).

SpxA1 (Spx)

amino acid sequence:

(SEQ ID NO: 44)

VLLSPLSVATALSALSLGADERTESIIHR nucleic acid sequence:

(SEQ ID NO: 45)

GTNYTNYTNWSNCCNYTNWSNGTNGCNACNGCNYTNWSNGCNYTNWSNYTNGGNGCNGAYGARMGNACNGARWSNATHATHCAYMGN 81-1 peptide -

(SEQ ID NO: 1)

SALSLGADERTESIIHR nucleic acid -

(SEQ ID NO: 21)

WSNGCNYTNWSNYTNGGNGCNGAYGARMGNACNGARWSNATHATHCAYMGN 81-2 peptide -

(SEQ ID NO: 2)

SAISIGADERTESIIHR nucleic acid -

(SEQ ID NO: 22)

WSNGCNATHWSNATHGGNGCNGAYGARMGNACNGARWSNATHATHCAYMGNTH 81-3 peptide -

(SEQ ID NO: 3)

SAISIGADARTASIIHR nucleic acid -

(SEQ ID NO: 23)

WSNGCNATHWSNATHGGNGCNGAYGCNMGNACNGCNWSNATHATHCAYMGNN 81-4 peptide -

(SEQ ID NO: 4)

{BA*}VLLSPLSVATALSAISIGADARTASIIHR{PEG*} nucleic acid -

(SEQ ID NO: 24)

GTNYTNYTNWSNCCNYTNWSNGTNGCNACNGCNYTNWSNGCNATHWSNATHGGNGCNGAYGCNMGNACNGCNWSNATHATHCAYMGN 81-5 peptide -

(SEQ ID NO: 5)

{BA*}SAISIGADARTASIIHR{PEG*} nucleic acid -

(SEQ ID NO: 25)

WSNGCNATHWSNATHGGNGCNGAYGCNMGNACNGCNWSNATHATHCAYMGN 81-6 peptide -

(SEQ ID NO: 6)

ALYYDLISSPDIHGT nucleic acid -

(SEQ ID NO: 26)

GCNYTNTAYTAYGAYYTNATHWSNWSNCCNGAYATHCAYGGNACN 81-7 peptide -

(SEQ ID NO: 7)

VLLSPLSVATAL nucleic acid -

(SEQ ID NO: 27)

GTNYTNYTNWSNCCNYTNWSNGTNGCNACNGCNYTN 81-8 peptide -

(SEQ ID NO: 8)

SALSLGADERTES nucleic acid -

(SEQ ID NO: 28)

WSNGCNYTNWSNYTNGGNGCNGAYGARMGNACNGARWSN 81-9 peptide -

(SEQ ID NO: 9)

SAISIGADARTAS nucleic acid -

(SEQ ID NO: 29)

WSNGCNATHWSNATHGGNGCNGAYGCNMGNACNGCNWSN 81-10 peptide -

(SEQ ID NO: 10)

VLLSPLSVATALSAISIGADARTASIIHR nucleic acid -

(SEQ ID NO: 30)

GTNYTNYTNWSNCCNYTNWSNGTNGCNACNGCNYTNWSNGCNATHWSNATHGGNGCNGAYGCNMGNACNGCNWSNATHATHCAYMGN 81-11 peptide -

(SEQ ID NO: 11)

{BA*}SAISIGADERTESIIHR{PEG*} nucleic acid -

(SEQ ID NO: 31)

WSNGCNATHWSNATHGGNGCNGAYGARMGNACNGARWSNATHATHCAYMGN 81-12 peptide -

(SEQ ID NO: 12)

{BA*}NFGYDLYRVRSSMSPTTNSALSLGADERTESIIHR{PEG*}

-continued nucleic acid -

(SEQ ID NO: 32)

AAYTTYGGNTAYGAYYTNTAYMGNGTNMGNWSNWSNATGWSNCCNACNAC
NAAYWSNGCNYTNWSNYTNGGNGCNGAYGARMGNACNGARWSNATHATHC
AYMGN 81-13 peptide -

(SEQ ID NO: 13)

SALSLGAAERTESIIHR nucleic acid -

(SEQ ID NO: 33)

WSNGCNYTNWSNYTNGGNGCNGCNGARMGNACNGARWSNATHATHCAYMG
N 81-14 peptide -

(SEQ ID NO: 14)

SALSLGANERTESIIHR nucleic acid -

(SEQ ID NO: 34)

WSNGCNYTNWSNYTNGGNGCNAAYGARMGNACNGARWSNATHATHCAYMG
N 81-15 peptide -

(SEQ ID NO: 15)

SALSLGADEATESIIHR nucleic acid -

(SEQ ID NO: 35)

WSNGCNYTNWSNYTNGGNGCNGAYGARGCNACNGARWSNATHATHCAYMG
N 81-16 peptide -

(SEQ ID NO: 16)

SADERTESIIHR nucleic acid -

(SEQ ID NO: 36)

WSNGCNGAYGARMGNACNGARWSNATHATHCAYMGN 81-17 peptide -

(SEQ ID NO: 17)

SALSLFADERTESIIHR nucleic acid -

(SEQ ID NO: 37)

WSNGCNYTNWSNYTNTTYGCNGAYGARMGNACNGARWSNATHAT
HCAYMGN 81-18 peptide -

(SEQ ID NO: 18)

SALSL (L-1-NAL)ADERTESIIHR nucleic acid -

(SEQ ID NO: 38)

WSNGCNYTNWSNYTN---

-continued (SEQ ID NO: 39)

GCNGAYGARMGNACNGARWSNATHATHCAYMGN 81-19 peptide -

(SEQ ID NO: 19)

FGADERTESIIHR nucleic acid -

(SEQ ID NO: 40)

TTYGGNGCNGAYGARMGNACNGARWSNATHATHCAYMGN 81-20 peptide -

(SEQ ID NO: 20)

L-1-NALGADERTESIIHR nucleic acid - ---

(SEQ ID NO: 41)

GCNYTNGGNGCNGAYGARMGNACNGARWSNATHATHCAYMGN

P78 amino acid sequence:

(SEQ ID NO: 42)

VLLSPLSVATALSALSLGADERTESIIHRALYYDLISSPDIHGT nucleic acid sequence:

(SEQ ID NO: 43)

GTGCTGCTGAGCCCGCTGTCGGTGGCAACCGCGCTGAGCGCTCT
GTCACTGGGCGCAGATGAACGTACTGAATCCATTATTCATCGCG
CGCTGTATTATGACCTGATTAGCTCTCCAGACATTCATGGCACC

TABLE 4

Nucleic acid code to generate computed sequences of peptide 81-1 to 81-20

| Code | Meaning | Etymology | Complement | Opposite |
|---|---|---|---|---|
| A | A | Adenosine | T | B |
| T/U | T or U | Thymidine/Uridine | A | V |
| G | G | Guanine | C | H |
| C | C | Cytidine | G | D |
| K | G or T | Keto | M | M |
| M | A or C | Amino | K | K |
| R | A or G | Purine | Y | Y |
| Y | C or T | Pyrimidine | R | R |
| S | C or G | Strong | S | W |
| W | A or T | Weak | W | S |
| B | C or G or T | not A (B comes after A) | V | A |
| V | A or C or G | not T/U (V comes after U) | B | T/U |
| H | A or C or T | not G (H comes after G) | D | G |
| D | A or G or T | not C (D comes after C) | H | C |
| X/N | G or A or T or C | any | N | . |
| . | not G or A or T or C | | . | N |
| — | gap of indeterminate length | | | |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising at least one peptide analog of pigment epithelium derived factor (PEDF), wherein the at least one peptide analog comprises at least one selected from the group consisting of 81-3 (SEQ ID NO: 3), 81-4 (SEQ ID NO: 4), 81-5 (SEQ ID NO: 5), and 81-10 (SEQ ID NO: 10).

2. The composition of claim 1, wherein the composition further comprises a pharmaceutical carrier.

3. The composition of claim 1, wherein the at least one peptide analog comprises 81-5 (SEQ ID NO: 5).

4. The composition of claim 1, wherein the composition is configured for delivery to the eye of a subject.

5. The composition of claim 1, wherein the composition is formulated as an eye drop, a gel, a foam or an injectate.

6. A method for reducing inflammation in a subject in need thereof, the method comprising administering to the subject a therapeutically effective amount of a composition comprising a peptide analog comprising 81-5 (SEQ ID NO:5).

7. The method of claim 6, wherein the composition is formulated as an eye drop, a gel, a foam or an injectate.

8. The method of claim 6, wherein the subject has a disease or disorder associated with angiogenesis.

9. The method of claim 6, wherein the subject has a disease or disorder selected from the group consisting of diabetic retinopathy, retinopathy of prematurity, age-related macular degeneration, retinitis pigmentosis, glaucoma, uveitis, corneal inflammation, diabetes, a neurodegenerative disease, nerve injury, sepsis, acute respiratory distress syndrome, nephrotic syndrome, diabetic neuropathy, preproliferative diabetic retinopathy, proliferative diabetic retinopathy, cancer and cystic fibrosis.

10. The method of claim 6, wherein the subject is a mammal.

11. The method of claim 10, wherein the mammal is a human.

12. The method of claim 6, wherein the composition is formulated as an implant wherein the implant releases the peptide analog.

13. A method of reducing the level of VEGF in a subject, the method comprising administering to a subject a composition comprising at least one peptide analog of PEDF, wherein the at least one peptide analog of PEDF is selected from the group consisting of 81-5 (SEQ ID NO: 5) and 81-10 (SEQ ID NO: 10).

14. A method of culturing a stem cell comprising contacting the stem cell with at least one peptide analog of PEDF, wherein the at least peptide analog comprises at least one selected from the group consisting of 81-3 (SEQ ID NO: 3), 81-4 (SEQ ID NO: 4), 81-5 (SEQ ID NO: 5), and 81-10 (SEQ ID NO: 10).

15. The method of claim 14, wherein the method comprises contacting the stem cell with a liquid medium comprising the at least one peptide analog.

* * * * *